(12) United States Patent
Mowat et al.

(10) Patent No.: US 10,023,539 B2
(45) Date of Patent: Jul. 17, 2018

(54) ARYL-CYANOGUANIDINE COMPOUNDS

(71) Applicant: Bayer Pharma Aktiengesellschaft, Berlin (DE)

(72) Inventors: Jeffrey Stuart Mowat, Berlin (DE); Timo Stellfeld, Berlin (DE); Carlo Stresemann, Berlin (DE); Roman Hillig, Berlin (DE); Silke Köhr, Teltow (DE); Detlef Stöckigt, Potsdam (DE); Jörg Weiske, Berlin (DE); Thomas Brumby, Berlin (DE); Naomi Barak, Berlin (DE); Clara Christ, Berlin (DE); Antonius Ter Laak, Berlin (DE); Volker Badock, Berlin (DE); Rosemary Helen Crampton, Bollington (GB); Ian Stefanuti, High Peak (GB)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/534,404

(22) PCT Filed: Dec. 8, 2015

(86) PCT No.: PCT/EP2015/078912
§ 371 (c)(1),
(2) Date: Jun. 8, 2017

(87) PCT Pub. No.: WO2016/091845
PCT Pub. Date: Jun. 16, 2016

(65) Prior Publication Data
US 2017/0342034 A1 Nov. 30, 2017

(30) Foreign Application Priority Data

Dec. 8, 2014 (EP) ..................................... 14196766
Apr. 17, 2015 (EP) ..................................... 15163993

(51) Int. Cl.
| C07D 231/06 | (2006.01) |
| C07D 401/12 | (2006.01) |
| C07D 403/12 | (2006.01) |
| C07D 413/12 | (2006.01) |

(52) U.S. Cl.
CPC ......... *C07D 231/06* (2013.01); *C07D 401/12* (2013.01); *C07D 403/12* (2013.01); *C07D 413/12* (2013.01)

(58) Field of Classification Search
CPC ............................ C07D 231/06; C07D 401/12
See application file for complete search history.

(56) References Cited

FOREIGN PATENT DOCUMENTS

| CA | 2532316 A1 | 1/2005 |
| WO | WO-1991011438 A1 | 8/1991 |
| WO | WO-2005007157 A1 | 1/2005 |
| WO | WO-2006/072350 A1 * | 7/2006 |

OTHER PUBLICATIONS

A machine English translation of WO 2006/072350 A1, Jul. 6, 2006.*
Golub et al., Science, vol. 286, Oct. 15, 1999, pp. 531-537.*
Ferguson, A.D. et. al. (2011) "Structural Basis of Substrate Methylation and Inhibition of SMYD2" *Structure* 19: 1262-1273.

(Continued)

*Primary Examiner* — Laura L Stockton
(74) *Attorney, Agent, or Firm* — Morrison & Foerster LLP

(57) ABSTRACT

The present invention relates to protein-lysine N-methyltransferase SMYD2 (SET and MYND domain-containing protein 2) inhibitors, in particular SMYD2-inhibitory substituted cyanoguanidine-pyrazolines of general formula (I) wherein $R^1$, $R^2$, $R^3$, $R^4$, $R^5$, X and r have the meaning as described and defined herein, as well as to pharmaceutical compositions comprising compounds according to the invention and to their prophylactic and therapeutic use for hyper-proliferative disorders, in particular for cancer, respectively tumor disorders. The present invention furthermore relates to the use of SMYD2 inhibitors for benign hyperplasias, atherosclerotic disorders, sepsis, autoimmune disorders, vascular disorders, viral infections, neurodegenerative disorders, inflammatory disorders, atherosclerotic disorders and the control of male fertility.

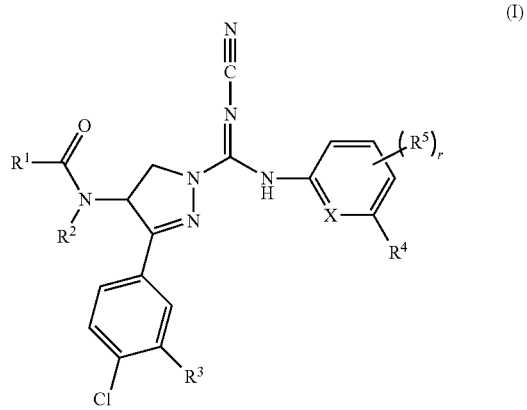

14 Claims, 2 Drawing Sheets

(56) References Cited

OTHER PUBLICATIONS

SGC homepage (Date Unknown) "LLY-507 A chemical probe for SMYD2 protein lysine methyltransferase," located at <http://www.thesgc.org/chemical-probes/LLY-507>, last visited on Jan. 30, 2018, two pages.

International Search Report dated Feb. 15, 2016, for PCT Application No. PCT/EP2015/078912, filed on Dec. 8, 2015, three pages.

* cited by examiner

SEQ ID NO: 1

```
MTSHHHHHHS SMGSRTSLYK KAGSDYDIPT TENLYFQGRA EGLGGLERFC SPGKGRGLRA
LQPFQVGDLL FSCPAYAYVL TVNERGNHCE YCFTRKEGLS KCGRCKQAFY CNVECQKEDW
PMHKLECSPM VVFGENWNPS ETVRLTARIL AKQKIHPERT PSEKLLAVKE FESHLDKLDN
EKKDLIQSDI AALHHFYSKH LGFPDNDSLV VLFAQVNCNG FTIEDEELSH LGSAIFPDVA
LMNESCCPNV IVTYKGTLAE VRAVQEIKPG EEVFTSYIDL LYPTEDRNDR LRDSYFFTCE
CQECTTKDKD KAKVEIRKLS DPPKAEAIRD MVRYARNVIE EFRRAKHYKS PSELLEICEL
SQEKMSSVFE DSNVYMLHMM YQAMGVCLYM QDWEGALQYG QKIIKPYSKH YPLYSLNVAS
MWLKLGRLYM GLEHKAAGEK ALKKAIAIME VAHGKDHPYI SEIKQEIESH
```

*FIG. 1*

SEQ ID NO: 2

```
        GRA EGLGGLERFC SPGKGRGLRA
LQPFQVGDLL FSCPAYAYVL TVNERGNHCE YCFTRKEGLS KCGRCKQAFY CNVECQKEDW
PMHKLECSPM VVFGENWNPS ETVRLTARIL AKQKIHPERT PSEKLLAVKE FESHLDKLDN
EKKDLIQSDI AALHHFYSKH LGFPDNDSLV VLFAQVNCNG FTIEDEELSH LGSAIFPDVA
LMNESCCPNV IVTYKGTLAE VRAVQEIKPG EEVFTSYIDL LYPTEDRNDR LRDSYFFTCE
CQECTTKDKD KAKVEIRKLS DPPKAEAIRD MVRYARNVIE EFRRAKHYKS PSELLEICEL
SQEKMSSVFE DSNVYMLHMM YQAMGVCLYM QDWEGALQYG QKIIKPYSKH YPLYSLNVAS
MWLKLGRLYM GLEHKAAGEK ALKKAIAIME VAHGKDHPYI SEIKQEIESH
```

*FIG. 2*

SEQUENCE LISTING

<160> NUMBER OF SEQ ID NOS: 3

<210> SEQ ID NO 1
<211> LENGTH: 470
<212> TYPE: PRT
<213> ORGANISM: Artificial Sequence
<220> FEATURE:
<223> OTHER INFORMATION: human SMYD2 with N-terminal His tag before cleavage by TEV protease

<400> SEQUENCE: 1

```
Met Thr Ser His His His His His His Ser Ser Met Gly Ser Arg Thr
1               5                   10                  15

Ser Leu Tyr Lys Lys Ala Gly Ser Asp Tyr Asp Ile Pro Thr Thr Glu
            20                  25                  30

Asn Leu Tyr Phe Gln Gly Arg Ala Glu Gly Leu Gly Gly Leu Glu Arg
        35                  40                  45

Phe Cys Ser Pro Gly Lys Gly Arg Gly Leu Arg Ala Leu Gln Pro Phe
    50                  55                  60

Gln Val Gly Asp Leu Leu Phe Ser Cys Pro Ala Tyr Ala Tyr Val Leu
65                  70                  75                  80

Thr Val Asn Glu Arg Gly Asn His Cys Glu Tyr Cys Phe Thr Arg Lys
                85                  90                  95

Glu Gly Leu Ser Lys Cys Gly Arg Cys Lys Gln Ala Phe Tyr Cys Asn
            100                 105                 110

Val Glu Cys Gln Lys Glu Asp Trp Pro Met His Lys Leu Glu Cys Ser
        115                 120                 125

Pro Met Val Val Phe Gly Glu Asn Trp Asn Pro Ser Glu Thr Val Arg
130                 135                 140

Leu Thr Ala Arg Ile Leu Ala Lys Gln Lys Ile His Pro Glu Arg Thr
145                 150                 155                 160

Pro Ser Glu Lys Leu Leu Ala Val Lys Glu Phe Glu Ser His Leu Asp
                165                 170                 175

Lys Leu Asp Asn Glu Lys Lys Asp Leu Ile Gln Ser Asp Ile Ala Ala
            180                 185                 190

Leu His His Phe Tyr Ser Lys His Leu Gly Phe Pro Asp Asn Asp Ser
        195                 200                 205

Leu Val Val Leu Phe Ala Gln Val Asn Cys Asn Gly Phe Thr Ile Glu
    210                 215                 220

Asp Glu Glu Leu Ser His Leu Gly Ser Ala Ile Phe Pro Asp Val Ala
225                 230                 235                 240

Leu Met Asn His Ser Cys Cys Pro Asn Val Ile Val Thr Tyr Lys Gly
                245                 250                 255

Thr Leu Ala Glu Val Arg Ala Val Gln Glu Ile Lys Pro Gly Glu Glu
            260                 265                 270

Val Phe Thr Ser Tyr Ile Asp Leu Leu Tyr Pro Thr Glu Asp Arg Asn
        275                 280                 285

Asp Arg Leu Arg Asp Ser Tyr Phe Phe Thr Cys Glu Cys Gln Glu Cys
    290                 295                 300
```

```
Thr Thr Lys Asp Lys Asp Lys Ala Lys Val Glu Ile Arg Lys Leu Ser
305                 310                 315                 320

Asp Pro Pro Lys Ala Glu Ala Ile Arg Asp Met Val Arg Tyr Ala Arg
                325                 330                 335

Asn Val Ile Glu Glu Phe Arg Arg Ala Lys His Tyr Lys Ser Pro Ser
            340                 345                 350

Glu Leu Leu Glu Ile Cys Glu Leu Ser Gln Glu Lys Met Ser Ser Val
        355                 360                 365

Phe Glu Asp Ser Asn Val Tyr Met Leu His Met Tyr Gln Ala Met
370                 375                 380

Gly Val Cys Leu Tyr Met Gln Asp Trp Glu Gly Ala Leu Gln Tyr Gly
385                 390                 395                 400

Gln Lys Ile Ile Lys Pro Tyr Ser Lys His Tyr Pro Leu Tyr Ser Leu
                405                 410                 415

Asn Val Ala Ser Met Trp Leu Lys Leu Gly Arg Leu Tyr Met Gly Leu
                420                 425                 430

Glu His Lys Ala Ala Gly Glu Lys Ala Leu Lys Lys Ala Ile Ala Ile
                435                 440                 445

Met Glu Val Ala His Gly Lys Asp His Pro Tyr Ile Ser Glu Ile Lys
            450                 455                 460

Gln Glu Ile Glu Ser His
465                 470

<210> SEQ ID NO 2
<211> LENGTH: 433
<212> TYPE: PRT
<213> ORGANISM: Artificial Sequence
<220> FEATURE:
<223> OTHER INFORMATION: human SMYD2 after cleavage by TEV protease

<400> SEQUENCE: 2

Gly Arg Ala Glu Gly Leu Gly Gly Leu Glu Arg Phe Cys Ser Pro Gly
1               5                   10                  15

Lys Gly Arg Gly Leu Arg Ala Leu Gln Pro Phe Gln Val Gly Asp Leu
                20                  25                  30

Leu Phe Ser Cys Pro Ala Tyr Ala Tyr Val Leu Thr Val Asn Glu Arg
            35                  40                  45

Gly Asn His Cys Glu Tyr Cys Phe Thr Arg Lys Glu Gly Leu Ser Lys
        50                  55                  60

Cys Gly Arg Cys Lys Gln Ala Phe Tyr Cys Asn Val Glu Cys Gln Lys
65                  70                  75                  80

Glu Asp Trp Pro Met His Lys Leu Glu Cys Ser Pro Met Val Val Phe
                85                  90                  95

Gly Glu Asn Trp Asn Pro Ser Glu Thr Val Arg Leu Thr Ala Arg Ile
                100                 105                 110

Leu Ala Lys Gln Lys Ile His Pro Glu Arg Thr Pro Ser Glu Lys Leu
            115                 120                 125

Leu Ala Val Lys Glu Phe Glu Ser His Leu Asp Lys Leu Asp Asn Glu
        130                 135                 140
```

```
Lys Lys Asp Leu Ile Gln Ser Asp Ile Ala Ala Leu His His Phe Tyr
145                 150                 155                 160

Ser Lys His Leu Gly Phe Pro Asp Asn Asp Ser Leu Val Val Leu Phe
                165                 170                 175

Ala Gln Val Asn Cys Asn Gly Phe Thr Ile Glu Asp Glu Glu Leu Ser
            180                 185                 190

His Leu Gly Ser Ala Ile Phe Pro Asp Val Ala Leu Met Asn His Ser
        195                 200                 205

Cys Cys Pro Asn Val Ile Val Thr Tyr Lys Gly Thr Leu Ala Glu Val
    210                 215                 220

Arg Ala Val Gln Glu Ile Lys Pro Gly Glu Glu Val Phe Thr Ser Tyr
225                 230                 235                 240

Ile Asp Leu Leu Tyr Pro Thr Glu Asp Arg Asn Asp Arg Leu Arg Asp
                245                 250                 255

Ser Tyr Phe Phe Thr Cys Glu Cys Gln Glu Cys Thr Thr Lys Asp Lys
                260                 265                 270

Asp Lys Ala Lys Val Glu Ile Arg Lys Leu Ser Asp Pro Pro Lys Ala
            275                 280                 285

Glu Ala Ile Arg Asp Met Val Arg Tyr Ala Arg Asn Val Ile Glu Glu
        290                 295                 300

Phe Arg Arg Ala Lys His Tyr Lys Ser Pro Ser Glu Leu Leu Glu Ile
305                 310                 315                 320

Cys Glu Leu Ser Gln Glu Lys Met Ser Ser Val Phe Glu Asp Ser Asn
                325                 330                 335

Val Tyr Met Leu His Met Met Tyr Gln Ala Met Gly Val Cys Leu Tyr
                340                 345                 350

Met Gln Asp Trp Glu Gly Ala Leu Gln Tyr Gly Gln Lys Ile Ile Lys
            355                 360                 365

Pro Tyr Ser Lys His Tyr Pro Leu Tyr Ser Leu Asn Val Ala Ser Met
        370                 375                 380

Trp Leu Lys Leu Gly Arg Leu Tyr Met Gly Leu Glu His Lys Ala Ala
385                 390                 395                 400

Gly Glu Lys Ala Leu Lys Lys Ala Ile Ala Ile Met Glu Val Ala His
                405                 410                 415

Gly Lys Asp His Pro Tyr Ile Ser Glu Ile Lys Gln Glu Ile Glu Ser
                420                 425                 430

His

<210> SEQ ID NO 3
<211> LENGTH: 20
<212> TYPE: PRT
<213> ORGANISM: Artificial Sequence
<220> FEATURE:
<223> OTHER INFORMATION: biotinylated peptide

<400> SEQUENCE: 3

Gly Ser Arg Ala His Ser Ser Leu Lys Ser Lys Lys Gly Gln Ser
1               5                   10                  15

Thr Ser Arg His
            20
```

ARYL-CYANOGUANIDINE COMPOUNDS

CROSS REFERENCE TO RELATED APPLICATIONS

This application is the national stage of International Application No. PCT/EP2015/078912, filed internationally on Dec. 8, 2015, which claims the benefit of European Application Nos. 14196766.1, filed Dec. 8, 2014, and 15163993.7, filed Apr. 17, 2015, the disclosures of which are hereby incorporated by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052015900seqlisting.txt, date recorded: Jun. 7, 2017, size: 9 KB).

The present invention relates to protein-lysine N-methyltransferase SMYD2 (SET and MYND domain-containing protein 2) inhibitors, in particular SMYD2-inhibitory substituted cyanoguanidine-pyrazolines, to pharmaceutical compositions comprising compounds according to the invention and to their prophylactic and therapeutic use for hyperproliferative disorders, in particular for cancer, respectively tumour disorders. The present invention furthermore relates to the use of SMYD2 inhibitors for benign hyperplasias, atherosclerotic disorders, sepsis, autoimmune disorders, vascular disorders, viral infections, neurodegenerative disorders, inflammatory disorders, atherosclerotic disorders and the control of male fertility.

BACKGROUND

Post-translational modifications (PTMs) of histone proteins, such as acetylation, methylation, phosphorylation, and ubiquitylation, play essential roles in regulating chromatin dynamics and gene expression (Jenuwein and Allis, Science, 2001, 293(5532):1074-80). Combinations of different modifications on histone proteins, termed the 'histone code', extend the information potential and regulate the readout of the genetic code. In addition to histones it has been found that many PTMs occur on non-histone proteins. These PTMs regulate protein-protein interactions, stability, localization, and/or enzymatic activities of proteins (Sims and Reinberg, Nat Rev Mol Cell Biol., 2008, 9:815-20). Therefore PTMs on non-histone proteins (e.g. on transcription factors) can substantially alter protein function, extending the regulatory role of PTMs to multiple cellular pathways (Benayoun and Veitia, Trends Cell Biol., 2009, 19(5):189-97). Along with serine, threonine and tyrosine phosphorylation, lysine methylation also plays a critical role in cell function (Huang and Berger, Curr Opin Genet Dev, 2008, 18(2):152-8). The enzymes responsible for lysine methylation were initially found to target histones. Accumulating evidence confirmed that some of these enzymes are not completely histone specific, but rather have a broader spectrum of protein substrates and are therefore termed protein lysine methyltransferases (PKMTs) (Lanouette et al., Mol Syst Biol., 2014, 10:724). Misregulation of PKMTs has been reported in cancer cell lines as well as in cancer patients (Miremadi et al., Hum Mol Genet., 2007, 16 Spec No 1:R28-49; Kudithipudi and Jeltsch, Biochim Biophys Acta, 2014, 1846 (2):366-379) Accordingly, lysine was shown to influence different pathways directly linked to oncogenic transformation, providing a rationale for the involvement of PKMTs in cancer and for developing inhibitors for therapeutic intervention (Mair et al., Trends Pharmacol Sci., 2014, 35(3): 136-45; Wagner and Jung, Nat Biotechnol., 2012, 30(7): 622-3).

In the present invention, inhibitors directed against the PKMT SET and MYND domain-containing protein 2 (SMYD2) are described. SMYD2 is a catalytic SET domain containing protein methyltransferase reported to monomethylate several lysine residues on histone and non-histone proteins. Initially SMYD2 was characterized to methylate H3 lysine 36 (Brown et al., Mol Cancer., 2006, 5:26) and lysine 4 when interacting with HSP90a (Abu-Farha et al., Mol Cell Proteomics, 2008, 7(3):560-722008). Methylation of histones by SMYD2 has been connected to increased transcription of genes involved in cell cycle regulation, chromatin remodeling, and transcriptional regulation (Abu-Farha et al., Mol Cell Proteomics, 2008, 7(3):560-722008). In addition to the function of SMYD2 in transcriptional regulation, several studies uncovered an important role of SMYD2 methylation activity on non-histone proteins closely connected to cancer.

For example, the p53 tumor suppressor gene is mutated in approximately 50% of human cancers and protein activity is frequently repressed in the non-mutated cases, indicating a central role of p53 in preventing tumorgenesis (Levine, Cell, 1997, 88(3):323-31). It has been demonstrated that the activity of p53 protein is inhibited by SMYD2 mediated posttranslational methylation at lysine 370 (K370) (Wu et al., Biochemistry, 2011, 50(29):6488-97; Huang et al., Nature, 2006, 444(7119):629-32;). The structural basis of p53 methylation by SMYD2 has been characterized by solving the crystal structure of a ternary complex with cofactor product S-adenosylhomocysteine and a p53 substrate peptide (Wang et al., J Biol Chem., 2011, 286(44): 38725-37). Methylation at K370 reduces the DNA-binding efficiency of p53 and subsequently prevents the transcriptional activation of the tumor suppressive genes p21 and MDM2 (Huang et al., Nature, 2006, 444(7119):629-32). In the same study, a knockdown of SMYD2 and treatment with doxorubicin led to an increase in p53-mediated cell-cycle arrest and apoptosis in a cancer cell line model. In line with these observations, low SMYD2 gene expression was suggested as predictive marker of an improved response to doxorubicin and cyclophosphamide neoadjuvant chemotherapy in breast cancer patients (Barros Filho et al., Braz J Med Biol Res., 2010, 43(12):1225-31). Additionally, a regulatory role of SMYD2 on p53 activity was confirmed independently in heart biology. SMYD2 was characterized in a cardiomyocyte model to be a cardioprotective protein by methylating p53, thereby reducing p53 mediated apoptosis induction (Sajjad et al., Biochim Biophys Acta., 2014, 1843(11):2556-62). Therefore SMYD2 inhibitors may provide new therapeutic options for cancers with SMYD2-mediated inactivation of the p53 tumor suppressor.

Another study revealed an additional link to cancer chemotherapy by uncovering the SMYD2-dependent methylation of poly(ADP-Ribose) Polymerase-1 (PARP1). Methylation of PARP1 at lysine 528 (K528) positively regulated the poly(ADP-ribosyl)ation activity of oncogenic protein PARP1 in cancer cells (Piao et al., Neoplasia, 2014, 16(3): 257-64). PARP1 is involved in the base excision pathway of DNA repair. Increased PARP1 activity is known as possible escape mechanism from apoptosis induction by DNA-damaging agents for cancer cells (Peralta-Leal et al., Clin Transl Oncol., 2008, 10(6):318-23). Knockdown of SMYD2 resulted in the reduction of PARP1 enzymatic activity, suggesting that SMYD2 inhibition could improve cancer chemotherapy efficacy (Piao et al., Neoplasia, 2014, 16(3): 257-64).

The retinoblastoma protein (Rb) is a further important tumor suppressor protein regulated by SMYD2. Rb normally restricts DNA replication by preventing the progression from G1 to the replicative S phase of the cell division cycle, by binding to and inhibiting transcription factors of the E2F family (Weinberg, Cell, 1995, 81(3):323-30). SMYD2 methylates Rb at lysine 810 (K810) and 860 (K860). SMYD2 methylation of K810 enhances phosphorylation of Rb and its dissociation from E2F, which promotes abnormal cell cycle progression to S phase and proliferation in cancer (Cho et al., Neoplasia, 2012, 14(6): 476-86) In line with these observations, it has been shown that knockdown of SMYD2 in an esophageal squamous cell carcinoma (ESCC) cell line overexpressing SMYD2 led to suppression of proliferation due to G1 arrest (Komatsu et al., Carcinogenesis, 2009, 30(7):1139-46). The HSP90 chaperone is another protein regulated by SMYD2. This protein is a crucial facilitator of oncogene addiction and cancer survival (Whitesell et al., Nat Rev Cancer., 2005, 5(10):761-72). Cancer cells are dependent on the HSP90 chaperone machinery to protect oncoproteins from misfolding and degradation. In a protein-protein interaction study, SMYD2 was identified as an interaction partner of HSP90 (Abu-Farha et al., J Mol Cell Biol., 2011, 3(5):301-8). Different studies revealed multiple sites of SMYD2 dependent HSP90 methylation at lysines 531 (K531) and 574 (K574) (Hamamoto et al., Cancer Lett., 2014, 351(1):126-33) and lysines K209 and K615 (Abu-Farha et al., J Mol Cell Biol., 2011, 3(5):301-8). Methylation was shown to be important for dimerization and chaperone complex stability. Initially HSP90 regulation by SMYD2 was described in normal muscle tissue maintenance (Donlin et al., Genes Dev., 2012, 26(2):114-9; Voelkel et al., Biochim Biophys Acta. 2013, 1833(4):812-22). Notably, an additional role of HSP90 methylation by SMYD2 in human carcinogenesis was reported (Hamamoto et al., Cancer Lett., 2014, 351(1):126-33). Knockdown of SMYD2 in cancer cell lines destabilized ERBB2 and CDK4 oncoproteins, and overexpression of methylated HSP90 accelerated proliferation of model cell lines indicating an additional cancer promoting role of SMYD2.

In the MCF7 breast cancer model it has been demonstrated that SMYD2-mediates estrogen receptor alpha (ERα) methylation at lysine 266 (K266). SMYD2 thereby also has a potential role in breast cancer by fine-tuning the functions of ERα and estrogen induced gene expression (Zhang et al., Proc Natl Acad Sci USA., 2013, 110(43): 17284-9; Jiang et al., J Mol Biol. 2014, 426(20):3413-25). In cancers, several studies detected abnormally high expression of SMYD2. In a model of aggressive acute myeloid leukemia (AML) containing the MLL-AF9 fusion oncoprotein, SMYD2 expression was identified as part of a program of aberrant self-renewal genes linked to leukemia stem cells and poor prognosis (Zuber et al., Genes Dev., 2011, 25: 1628-1640). Different studies reported overexpression of SMYD2 in cancer cell lines as well as in ESCC, bladder carcinoma, gastric cancer and pediatric acute lymphoblastic leukemia patients (Komatsu et al., Carcinogenesis, 2009, 30(7):1139-46 and Br J Cancer, 2014, doi: 10.1038/bjc.2014.543; Cho et al., Neoplasia, 2012, 14(6):476-86; Sakamoto et al, 2014, 38(4):496-502). Notably higher SMYD2 expression in ESCC, gastric cancer, and acute lymphoblastic leukemia patients correlated with lower survival rate and was suggested to be a clinically relevant prognostic marker, further indicating an oncogenic role of SMYD2 (Komatsu et al., Carcinogenesis, 2009, 30(7):1139-46 and Br J Cancer, 2014, doi: 10.1038/bjc.2014.543; Sakamoto et al., Leuk Res., 2014, 38(4):496-502). In validation experiments in these reports, knockdown of SMYD2 in overexpressing ESCC, bladder and gastric cancer cell line models significantly reduced cell proliferation. One potential underlying explanation for higher SMYD2 expression in cancer patients was described for ESCC. The SMYD2 gene is localized in a genomic region around 1q32 q41 which has been found to be frequently amplified in ESCC cell lines and patients (Komatsu et al., Carcinogenesis, 2009, 30(7):1139-46; Pimkhaokham et al., Jpn J Cancer Res., 2000, 91(11): 1126-33).

These studies indicate that the SMYD2 proteins play an essential role in various pathologies. It would therefore be desirable to find potent and selective inhibitors which prevent the SMYD2 methylation activity.

PRIOR ART

WO 2006/072350 discloses cyanoguanidine-substituted pyrazolines and the use of such compounds as medicaments related to the field of blood coagulation. The examples of this application consist only of 3-(4-chlorophenyl)-4,5-dihydro-1H-pyrazoles, which are only weak SMYD2 inhibitors. There is no specific example which is covered by the formula (I) as described and defined herein.

WO 2005/007157 discloses pyrazolines as PAR-1 antagonists for treatment of cardiovascular diseases. However, the specific examples disclosed in WO 2005/007157 are not covered by the formula (I) as described and defined herein.

WO 1991/11438 discloses arthropodicidal pyrazolines. The claimed 4,5-dihydro-1H-pyrazoles may be substituted in the 4-position, but not with a nitrogen atom at this position.

The specific examples disclosed in WO 1991/11438 are not covered by the formula (I) as described and defined herein.

Based on the chemical structure, only very few types of Smyd 2 inhibitors have been described to date. Ferguson et. al. reported the discovery of AZ505 and the crystal structure of Smyd2 in complex with AZ505 (Structure 19, 1262-1273, Sep. 7, 2011). The SGC in collaboration with Ely Lilly and Company published the discovery of the Smyd2 inhibitor LLY-507. Inhibitors showing in vivo activity have not been reported to date.

Accordingly, it would be desirable to provide novel compounds having prophylactic and therapeutic properties.

BRIEF DESCRIPTION OF THE DRAWINGS

FIG. 1 shows the sequence of human SMYD2 with N-terminal His tag before cleavage by TEV protease (SEQ ID NO: 1).

FIG. 2 shows the sequence of human SMYD2 after cleavage by TEV protease (SEQ ID NO: 2).

DETAILED DESCRIPTION OF THE INVENTION

Figure 3:
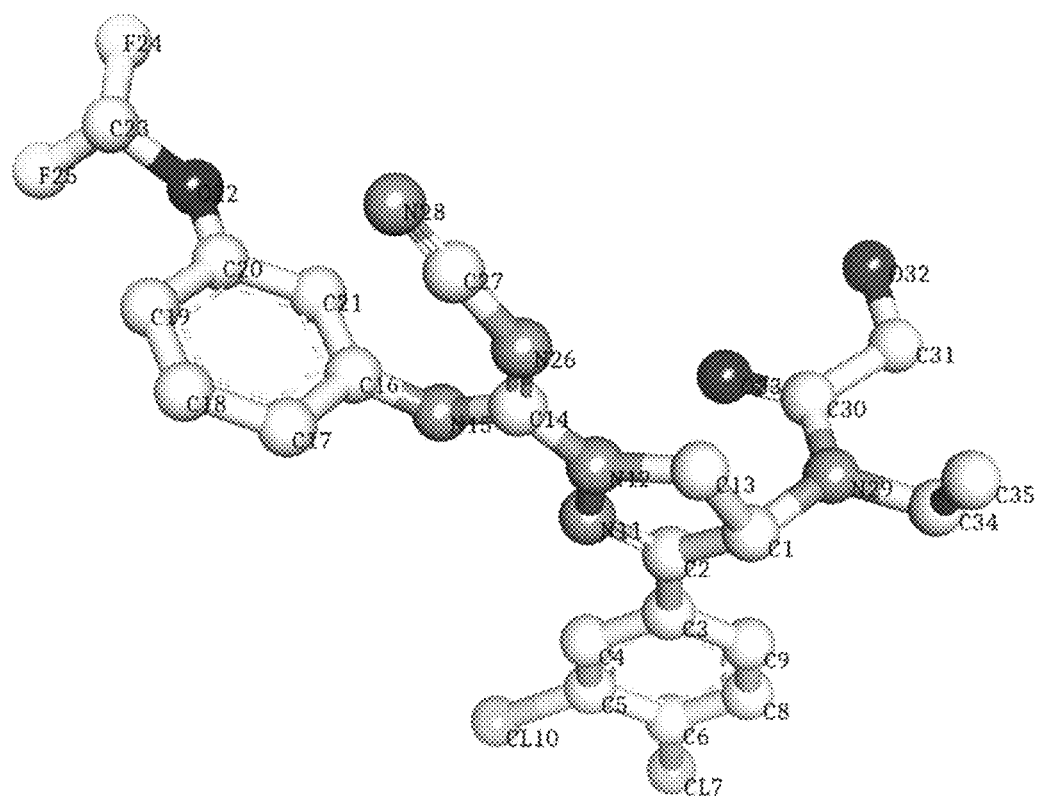
FIG. 3 shows the Example 4.1 in complex with human SMYD2 and SAM.

It is therefore an object of the present invention to provide compounds and pharmaceutical compositions comprising these compounds as SMYD2 protein inhibitors for prophylactic and therapeutic use for hyperproliferative disorders, in particular for cancer, respectively tumour disorders, for benign hyperplasias, atherosclerotic disorders, sepsis, autoimmune disorders, vascular disorders, viral infections, neurodegenerative disorders, inflammatory disorders, atherosclerotic disorders and the control of male fertility.

It has now been found that compounds of general formula (I)

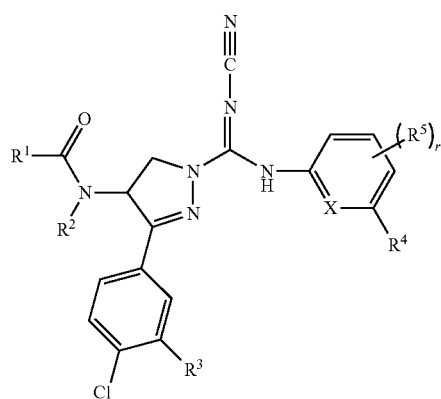

in which:
R¹ represents a $C_1$-$C_6$-alkyl group, which is substituted with one substituent selected from —OH, —NH$_2$ or —NHCH$_3$,
R² represents a hydrogen atom, a methyl or an ethyl group,
R³ represents a fluorine or a chlorine atom or a methyl group,
R⁴ represents a group selected from: —CF$_3$, —CH$_2$CF$_3$, —OCH$_3$, —OCHF$_2$, —OCF$_3$, —OCH$_2$CF$_3$ or —OCH$_2$CH$_2$N(CH$_3$)$_2$,
R⁵ represents a fluorine or a chlorine atom or a group selected from: —OCH$_3$, —OCF$_3$,

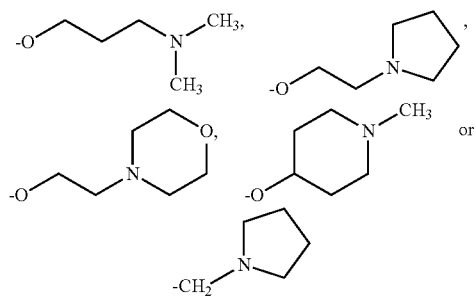

X represents CH or N,
r represents 0 or 1,
as well as their polymorphs, enantiomers, diastereomers, racemates, E/Z-isomers, tautomers, solvates, physiological acceptable salts and solvates of these salts can be prophylactically and therapeutically used in a wide range of diseases, especially in hyperproliferative diseases, and more especially in cancer, respectively tumor treatment.

The terms as mentioned in the instant invention are based on the following definitions:
Alkyl The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.
Alkoxy The term "$C_1$-$C_6$-alkoxy" is to be understood as preferably meaning a linear or branched, saturated, monovalent group of formula-O—($C_1$-$C_6$-alkyl), in which the term "$C_1$-$C_6$-alkyl" is defined above, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The compounds of this invention contain one or more asymmetric centres, depending upon the location and nature of the various substituents desired. Asymmetric carbon atoms may be present in the (R) or (S) configuration. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Diacel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The present invention includes all possible stereoisomers of the compounds of the present invention as single stereoisomers, or as any mixture of said stereoisomers, in any ratio. Isolation of a single stereoisomer, e.g. a single enantiomer or a single diastereomer, of a compound of the present invention may be achieved by any suitable state of the art method, such as chromatography, especially chiral chromatography, for example.

The cyanoguanidine moiety can formally adopt E- or Z-configuration:

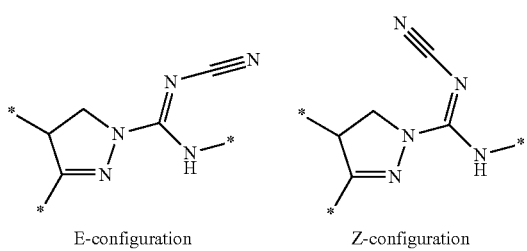 [SMILES: *N/C(=N\C#N)N1CC(*)C(*)=N1 ; *N/C(=N/C#N)N1CC(*)C(*)=N1]

E-configuration  Z-configuration

It is assumed, that at relevant temperatures, the two isomers are present in a fast equilibrium, and cannot be analytically or preparatively distinguished, as similarly described for N,N,N',N'-tetramethylcyanoguanidines (C. Gordon McCarty and Donald M. Wieland: Syn-Anti Isomerization Involving the N-Cyanoimino Group; Tetrahedron Letters No. 22, PP. 1787-1790, 1969). Therefore, any representation of the cyanoguanidine used herein represents both isomers.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, viz.:

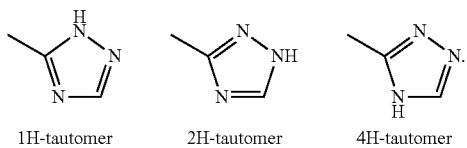

1H-tautomer  2H-tautomer  4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

Furthermore, the present invention includes all possible crystalline forms, or polymorphs, of the compounds of the present invention, either as single polymorphs, or as a mixture of more than one polymorphs, in any ratio.

Of particular interest are those compounds of general formula (I), in which
$R^1$ represents a group selected from: —CH$_2$—OH, —CH(OH)—CH$_3$, —C(CH$_3$)$_2$—OH, —CH$_2$—NH$_2$, —CH(CH$_3$)—NH$_2$, —CH$_2$—CH$_2$—NH$_2$ or —CH$_2$—CH$_2$—CH$_2$—NH$_2$,
$R^2$ represents a hydrogen atom, a methyl or an ethyl group,
$R^3$ represents a fluorine or a chlorine atom or a methyl group,
$R^4$ represents a group selected from: —CF$_3$, —CH$_2$CF$_3$, —OCH$_3$, —OCHF$_2$, —OCF$_3$ or —OCH$_2$CH$_2$N(CH$_3$)$_2$,
$R^5$ represents a fluorine or a chlorine atom or a group selected from: —OCH$_3$, —OCF$_3$,

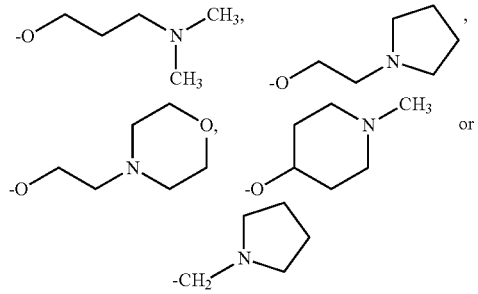

X represents CH or N,
r represents 0 or 1,
as well as their polymorphs, enantiomers, diastereomers, racemates, E/Z-isomers, tautomers, solvates, physiological acceptable salts and solvates of these salts.

It is to be understood that the present invention relates to any sub-combination within any embodiment or aspect of the present invention of compounds of general formula (I), above.

In another embodiment, the present invention relates to compounds of the general formula (I), above, in which:
$R^1$ represents a C$_1$-C$_3$-alkyl group, which is substituted with one substituent selected from a hydroxy or an amino group.

In another embodiment, the present invention relates to compounds of the general formula (I), above, in which:
$R^2$ represents a hydrogen atom, a methyl or an ethyl group.

In another embodiment, the present invention relates to compounds of the general formula (I), above, in which:
$R^2$ represents a hydrogen atom or a methyl group.

In another embodiment, the present invention relates to compounds of the general formula (I), above, in which:
$R^2$ represents a hydrogen atom.

In another embodiment, the present invention relates to compounds of the general formula (I), above, in which:
$R^2$ represents a methyl or an ethyl group.

In another embodiment, the present invention relates to compounds of the general formula (I), above, in which:
$R^3$ represents a fluorine or a chlorine atom or a methyl group.

In another embodiment, the present invention relates to compounds of the general formula (I), above, in which:
$R^3$ represents a fluorine or a chlorine atom.

In another embodiment, the present invention relates to compounds of the general formula (I), above, in which:
$R^3$ represents a fluorine atom.

In another embodiment, the present invention relates to compounds of the general formula (I), above, in which:
$R^3$ represents a chlorine atom.

In another embodiment, the present invention relates to compounds of the general formula (I), above, in which:
$R^4$ represents a group selected from: —CF$_3$, —CH$_2$CF$_3$, —OCH$_3$, —OCHF$_2$, —OCF$_3$ or —OCH$_2$CH$_2$N(CH$_3$)$_2$.

In another embodiment, the present invention relates to compounds of the general formula (I), above, in which:
$R^4$ represents a group selected from: —CF$_3$, —CH$_2$CF$_3$, —OCH$_3$, —OCHF$_2$ or —OCF$_3$.

In another embodiment, the present invention relates to compounds of the general formula (I), above, in which:
$R^5$ represents a fluorine or a chlorine atom or a group selected from: —OCH$_3$, —OCF$_3$,

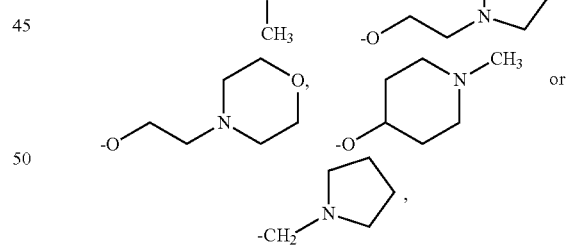

In another embodiment, the present invention relates to compounds of the general formula (I), above, in which:
$R^5$ represents a fluorine or a chlorine atom.

In another embodiment, the present invention relates to compounds of the general formula (I), above, in which:
$R^5$ represents a group selected from: —OCH$_3$, —OCF$_3$,

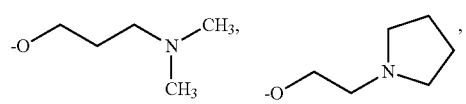

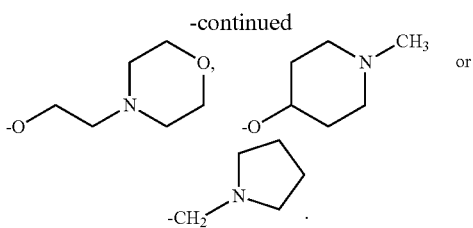

In another embodiment, the present invention relates to compounds of the general formula (I), above, in which:
X represents CH or N.

In another embodiment, the present invention relates to compounds of the general formula (I), above, in which:
X represents CH.

In another embodiment, the present invention relates to compounds of the general formula (I), above, in which:
X represents N.

In another embodiment, the present invention relates to compounds of the general formula (I), above, in which:
r represents 0 or 1.

In another embodiment, the present invention relates to compounds of the general formula (I), above, in which:
r represents 0.

In another embodiment, the present invention relates to compounds of the general formula (I), above, in which:
r represents 1.

In a preferred embodiment, the present invention relates to compounds of general formula (I), above, in which:
$R^1$ represents a group selected from: —CH$_2$—OH, —CH(OH)—CH$_3$, —C(CH$_3$)$_2$—OH, —CH$_2$—NH$_2$, —CH(CH$_3$)—NH$_2$, —CH$_2$—CH$_2$—NH$_2$ or —CH$_2$—CH$_2$—CH$_2$—NH$_2$.

Of selected interest are those compounds of general formula (I):

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxypropanamide (1:1 mixture of diastereomers);

Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-N-methylacetamide;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylglycinamide;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide;

N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 1;

N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 2;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-beta-alaninamide;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide (1:1 mixture of diastereomers);

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 1;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 2;

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 mixture of diastereomers);

(2R)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 mixture of diastereomers);

Rac-4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide;

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 1;

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 2;

Rac-N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide;

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 1;

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[4-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide;

Rac-N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide;

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 1;

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 2;

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide;

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 1;

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 2;

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethylglycinamide;

Rac-N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide;

N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(difluoromethoxy)-4-fluorophenyl]carbamimidoyl}-3-(3,4-dichlorophenyl)-4,5-dihydro-1H-pyrazol-4-yl]-N-ethyl-2-hydroxyacetamide;

Rac-N-[1-{N'-cyano-N-[3-(difluoromethoxy)-2-fluorophenyl]carbamimidoyl}-3-(3,4-dichlorophenyl)-4,5-dihydro-1H-pyrazol-4-yl]-N-ethyl-2-hydroxyacetamide;

Rac-N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-methoxy-5-(trifluoromethoxy)phenyl]carbamimidoyl}-3-(3,4-dichlorophenyl)-4,5-dihydro-1H-pyrazol-4-yl]-N-ethyl-2-hydroxyacetamide;

Rac-N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-(trifluoromethoxy)-5-(trifluoromethyl)phenyl]carbamimidoyl}-3-(3,4-dichlorophenyl)-4,5-dihydro-1H-pyrazol-4-yl]-N-ethyl-2-hydroxyacetamide;

Rac-N-[1-(N'-cyano-N-{5-(difluoromethoxy)-2-[3-(dimethylamino)propoxy]phenyl}-carbamimidoyl)-3-(3,4-dichlorophenyl)-4,5-dihydro-1H-pyrazol-4-yl]-N-ethyl-2-hydroxyacetamide;

Rac-N-[1-(N'-cyano-N-{2-[2-(pyrrolidin-1-yl)ethoxy]-5-(trifluoromethyl)phenyl}carbamimidoyl)-3-(3,4-dichlorophenyl)-4,5-dihydro-1H-pyrazol-4-yl]-N-ethyl-2-hydroxyacetamide;

Rac-N-[1-(N'-cyano-N-{2-[(1-methylpiperidin-4-yl)oxy]-5-(trifluoromethyl)phenyl}-carbamimidoyl)-3-(3,4-dichlorophenyl)-4,5-dihydro-1H-pyrazol-4-yl]-N-ethyl-2-hydroxyacetamide;

Rac-N-[1-(N'-cyano-N-{2-[(1-methylpiperidin-4-yl)oxy]-5-(trifluoromethyl)phenyl}-carbamimidoyl)-3-(3,4-dichlorophenyl)-4,5-dihydro-1H-pyrazol-4-yl]-N-ethyl-2-hydroxyacetamide;

Rac-N-[3-(4-chloro-3-methylphenyl)-1-{N'-cyano-N-[3-(difluoromethoxy)phenyl]-carbamimidoyl}-4,5-dihydro-1H-pyrazol-4-yl]-N-ethyl-2-hydroxyacetamide;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-2-hydroxyacetamide Isomer 1;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-2-hydroxyacetamide Isomer 2;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide (1:1 mixture of diastereomers);

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide Isomer 1;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide Isomer 2 and Rac-N-[3-(4-chloro-3-fluorophenyl)-1-{N'-cyano-N-[3-(trifluoromethoxy)phenyl]-carbamimidoyl}-4,5-dihydro-1H-pyrazol-4-yl]-N-ethyl-2-hydroxyacetamide;

as well as their polymorphs, enantiomers, diastereomers, racemates, E/Z isomers, tautomers, solvates, physiological acceptable salts and solvates of these salts.

Of selected interest are those compounds of general formula (I):

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxypropanamide (1:1 mixture of diastereomers);

Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-N-methylacetamide;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylglycinamide;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide;

N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 1;

N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 2;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-beta-alaninamide;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide (1:1 mixture of diastereomers);

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 1;

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 2;

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 mixture of diastereomers);

(2R)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 mixture of diastereomers);

Rac-4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide;

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 1;

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 2;

Rac-N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide;

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 1;

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[4-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide;

Rac-N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide;

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 1;

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 2;

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide;

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 1;

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 2;

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethylglycinamide;

Rac-N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-methoxy-5-(trifluoromethyl)phenyl]
carbamimidoyl}-3-(3,4-dichlorophenyl)-4,5-dihydro-1H-
pyrazol-4-yl]-N-ethyl-2-hydroxyacetamide Isomer 2;
Rac-N-[1-{N'-cyano-N-[6-(difluoromethoxy)pyridin-2-yl]
carbamimidoyl}-3-(3,4-dichlorophenyl)-4,5-dihydro-1H-
pyrazol-4-yl]-N-ethyl-2-hydroxyacetamide;
N-[1-{N'-cyano-N-[6-(difluoromethoxy)pyridin-2-yl]car-
bamimidoyl}-3-(3,4-dichlorophenyl)-4,5-dihydro-1H-
pyrazol-4-yl]-N-ethyl-2-hydroxyacetamide Isomer 1;
N-[1-{N'-cyano-N-[6-(difluoromethoxy)pyridin-2-yl]car-
bamimidoyl}-3-(3,4-dichlorophenyl)-4,5-dihydro-1H-
pyrazol-4-yl]-N-ethyl-2-hydroxyacetamide Isomer 2;
Rac-N-[1-{N'-cyano-N-[3-(2,2,2-trifluoroethyl)phenyl]car-
bamimidoyl}-3-(3,4-dichlorophenyl)-4,5-dihydro-1H-
pyrazol-4-yl]-N-ethyl-2-hydroxyacetamide;
N-[1-{N'-cyano-N-[3-(2,2,2-trifluoroethyl)phenyl]carbam-
imidoyl}-3-(3,4-dichlorophenyl)-4,5-dihydro-1H-pyra-
zol-4-yl]-N-ethyl-2-hydroxyacetamide Isomer 1;
N-[1-{N'-cyano-N-[3-(2,2,2-trifluoroethyl)phenyl]carbam-
imidoyl}-3-(3,4-dichlorophenyl)-4,5-dihydro-1H-pyra-
zol-4-yl]-N-ethyl-2-hydroxyacetamide Isomer 2;
Rac-N-[1-{N'-cyano-N-[3-(difluoromethoxy)-4-fluorophe-
nyl]carbamimidoyl}-3-(3,4-dichlorophenyl)-4,5-dihydro-
1H-pyrazol-4-yl]-N-ethyl-2-hydroxyacetamide;
Rac-N-[1-{N'-cyano-N-[3-(difluoromethoxy)-2-fluorophe-
nyl]carbamimidoyl}-3-(3,4-dichlorophenyl)-4,5-dihydro-
1H-pyrazol-4-yl]-N-ethyl-2-hydroxyacetamide;
Rac-N-[1-{N'-cyano-N-[3-(difluoromethoxy)-5-fluorophe-
nyl]carbamimidoyl}-3-(3,4-dichlorophenyl)-4,5-dihydro-
1H-pyrazol-4-yl]-N-ethyl-2-hydroxyacetamide;
N-[1-{N'-cyano-N-[3-(difluoromethoxy)-5-fluorophenyl]
carbamimidoyl}-3-(3,4-dichlorophenyl)-4,5-dihydro-1H-
pyrazol-4-yl]-N-ethyl-2-hydroxyacetamide Isomer 1;
N-[1-{N'-cyano-N-[3-(difluoromethoxy)-5-fluorophenyl]
carbamimidoyl}-3-(3,4-dichlorophenyl)-4,5-dihydro-1H-
pyrazol-4-yl]-N-ethyl-2-hydroxyacetamide Isomer 2;
Rac-N-[1-{N'-cyano-N-[3-fluoro-5-(trifluoromethoxy)phe-
nyl]carbamimidoyl}-3-(3,4-dichlorophenyl)-4,5-dihydro-
1H-pyrazol-4-yl]-N-ethyl-2-hydroxyacetamide;
N-[1-{N'-cyano-N-[3-fluoro-5-(trifluoromethoxy)phenyl]
carbamimidoyl}-3-(3,4-dichlorophenyl)-4,5-dihydro-1H-
pyrazol-4-yl]-N-ethyl-2-hydroxyacetamide Isomer 1;
N-[1-{N'-cyano-N-[3-fluoro-5-(trifluoromethoxy)phenyl]
carbamimidoyl}-3-(3,4-dichlorophenyl)-4,5-dihydro-1H-
pyrazol-4-yl]-N-ethyl-2-hydroxyacetamide Isomer 2;
Rac-N-[1-{N'-cyano-N-[2-methoxy-5-(trifluoromethoxy)
phenyl]carbamimidoyl}-3-(3,4-dichlorophenyl)-4,5-di-
hydro-1H-pyrazol-4-yl]-N-ethyl-2-hydroxyacetamide;
Rac-N-[1-{N'-cyano-N-[2-(pyrrolidin-1-ylmethyl)-5-(trif-
luoromethyl)phenyl]carbamimidoyl}-3-(3,4-dichlorophe-
nyl)-4,5-dihydro-1H-pyrazol-4-yl]-N-ethyl-2-hydroxyac-
etamide;
N-[1-{N'-cyano-N-[2-(pyrrolidin-1-ylmethyl)-5-(trifluo-
romethyl)phenyl]carbamimidoyl}-3-(3,4-dichlorophe-
nyl)-4,5-dihydro-1H-pyrazol-4-yl]-N-ethyl-2-hydroxyac-
etamide Isomer 1;
N-[1-{N'-cyano-N-[2-(pyrrolidin-1-ylmethyl)-5-(trifluo-
romethyl)phenyl]carbamimidoyl}-3-(3,4-dichlorophe-
nyl)-4,5-dihydro-1H-pyrazol-4-yl]-N-ethyl-2-hydroxyac-
etamide Isomer 2;
Rac-N-[1-{N'-cyano-N-[2-(trifluoromethoxy)-5-(trifluo-
romethyl)phenyl]carbamimidoyl}-3-(3,4-dichlorophe-
nyl)-4,5-dihydro-1H-pyrazol-4-yl]-N-ethyl-2-hydroxyac-
etamide;
Rac-N-[1-(N'-cyano-N-{5-(difluoromethoxy)-2-[3-(dimeth-
ylamino)propoxy]phenyl}-carbamimidoyl)-3-(3,4-di-
chlorophenyl)-4,5-dihydro-1H-pyrazol-4-yl]-N-ethyl-2-
hydroxyacetamide;
Rac-N-[1-(N'-cyano-N-{2-[2-(pyrrolidin-1-yl)ethoxy]-5-
(trifluoromethyl)phenyl}carbamimidoyl)-3-(3,4-dichlo-
rophenyl)-4,5-dihydro-1H-pyrazol-4-yl]-N-ethyl-2-hy-
droxyacetamide;
Rac-N-[1-(N'-cyano-N-{2-[(1-methylpiperidin-4-yl)oxy]-5-
(trifluoromethyl)phenyl}-carbamimidoyl)-3-(3,4-dichlo-
rophenyl)-4,5-dihydro-1H-pyrazol-4-yl]-N-ethyl-2-hy-
droxyacetamide;
Rac-N-[1-(N'-cyano-N-{2-[(1-methylpiperidin-4-yl)oxy]-5-
(trifluoromethyl)phenyl}-carbamimidoyl)-3-(3,4-dichlo-
rophenyl)-4,5-dihydro-1H-pyrazol-4-yl]-N-ethyl-2-hy-
droxyacetamide;
Rac-N-[3-(4-chloro-3-methylphenyl)-1-{N'-cyano-N-[3-
(difluoromethoxy)phenyl]-carbamimidoyl}-4,5-dihydro-
1H-pyrazol-4-yl]-N-ethyl-2-hydroxyacetamide;
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-2-hydroxyacetamide Isomer 1;
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-2-hydroxyacetamide Isomer 2;
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-L-alaninamide (1:1 mixture of
diastereomers);
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-L-alaninamide Isomer 1;
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-L-alaninamide Isomer 2
Rac-N-[3-(4-chloro-3-fluorophenyl)-1-{N'-cyano-N-[3-(tri-
fluoromethoxy)phenyl]-carbamimidoyl}-4,5-dihydro-
1H-pyrazol-4-yl]-N-ethyl-2-hydroxyacetamide;
Rac-N-[3-(4-chloro-3-methylphenyl)-1-{N'-cyano-N-[3-
(difluoromethoxy)phenyl]carbamimidoyl}-4,5-dihydro-
1H-pyrazol-4-yl]-N-ethyl-$N^2$-methylglycinamide
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-$N^2$-methylglycinamide Isomer 1
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-$N^2$-methylglycinamide Isomer 2
N-[3-(4-chloro-3-methylphenyl)-1-{N'-cyano-N-[3-(difluo-
romethoxy)phenyl]carbamimidoyl}-4,5-dihydro-1H-
pyrazol-4-yl]-N-ethyl-$N^2$-methyl-D-alaninamide
Rac-N-[1-{N'-cyano-N-[3-(difluoromethoxy)phenyl]car-
bamimidoyl}-3-(3,4-dichlorophenyl)-4,5-dihydro-1H-
pyrazol-4-yl]-3-methyl-D-isovalinamide
N-[1-{N'-Cyano-N-[3-(difluoromethoxy)phenyl]carbamim-
idoyl}-3-(3,4-dichlorophenyl)-4,5-dihydro-1H-pyrazol-
4-yl]-3-methyl-D-isovalinamide Isomer 1
N-[1-{N'-Cyano-N-[3-(difluoromethoxy)phenyl]carbamim-
idoyl}-3-(3,4-dichlorophenyl)-4,5-dihydro-1H-pyrazol-
4-yl]-3-methyl-D-isovalinamide Isomer 2
N-[1-{N'-cyano-N-[3-(trifluoromethoxy)phenyl]carbamim-
idoyl}-3-(3,4-dichlorophenyl)-4,5-dihydro-1H-pyrazol-
4-yl]-N-ethyl-D-leucinamide
N-[1-{N'-Cyano-N-[2-fluoro-3-(trifluoromethoxy)phenyl]
carbamimidoyl}-3-(3,4-dichlorophenyl)-4,5-dihydro-1H-
pyrazol-4-yl]-N-ethyl-D-valinamide and N-[1-{N'-Cyano-N-[3-(difluoromethoxy)phenyl]carbamimidoyl}-3-(3,4-dichlorophenyl)-4,5-dihydro-1H-pyrazol-4-yl]-N-ethyl-D-valinamide as well as their polymorphs, enantiomers, diastereomers, racemates, E/Z isomers, tautomers, solvates, physiological acceptable salts and solvates of these salts.

The compounds of general formula (I) can be used for the prophylactic and therapeutic treatment in hyperproliferative disorders, especially in cancer, respectively tumour disorders.

The compounds of general formula (I) can be used as SMYD2 inhibitors in benign hyperplasias, atherosclerotic disorders, sepsis, autoimmune disorders, vascular disorders, viral infections, neurodegenerative disorders, inflammatory disorders, atherosclerotic disorders and control of male fertility.

The instant invention further relates the production of a medicament comprising a compound of general formula (I). Said medicament can be used prophylactically and therapeutically in a human or in another mammal.

The present invention moreover also includes prodrugs of the compounds according to the invention. The term "prodrugs" here designates compounds which themselves can be biologically active or inactive, but are converted (for example metabolically or hydrolytically) into compounds according to the invention during their dwell time in the body.

The compounds according to the invention can act systemically and/or locally. For this purpose, they can be administered in a suitable manner, such as, for example, orally, parenterally, pulmonarily, nasally, sublingually, lingually, buccally, rectally, dermally, transdermally, conjunctivally, otically, as or as an implant or stent.

For these administration routes, the compounds according to the invention can be administered in suitable administration forms.

Suitable for oral administration are administration forms working according to the prior art, which release the compounds according to the invention rapidly and/or in modified form and comprise the compounds according to the invention in crystalline and/or amorphized and/or dissolved form, such as, for example, tablets (non-coated or coated tablets, for example coated with enteric, slowly dissolving or insoluble coats which control the release of the compound according to the invention), tablets which decompose rapidly in the oral cavity or films/wafers, films/lyophylizates, capsules (for example hard gelatin capsules or soft gelatin capsules), sugar-coated tablets, granules, pellets, powders, emulsions, suspensions, aerosols or solutions.

Parenteral administration can take place with circumvention of an absorption step (for example intravenous, intraarterial, intracardiac, intraspinal or intralumbar) or with involvement of an absorption (for example intramuscular, subcutaneous, intracutaneous, percutaneous or intraperitoneal). For parenteral administration, suitable administration forms are, inter alia, injection and infusion preparations in the form of solutions, suspensions, emulsions, lyophilizates or sterile powders.

Suitable for the other administration routes are, for example, pharmaceutical forms for inhalation (inter alia powder inhalers, nebulizers), nasal drops, nasal solutions, nasal sprays; tablets, films/wafers or capsules to be applied lingually, sublingually or buccally, suppositories, ear or eye preparations, vaginal capsules, aqueous suspensions (lotions, shake lotions), lipophilic suspensions, ointments, creams, transdermal therapeutic systems (such as, for example, patches), milk, pastes, foams, dusting powders, implants or stents.

The compounds according to the invention can be converted into the administration forms mentioned. This may take place in a manner known per se by mixing with inert non-toxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as, for example, ascorbic acid), colorants (e.g. inorganic pigments such as, for example, iron oxides) and taste and/or odour corrigents.

The present invention furthermore provides medicaments comprising the compounds according to the invention, usually together with one or more inert non-toxic, pharmaceutically suitable auxiliaries, and their use for the purposes mentioned.

Formulation of the compounds according to the invention to give pharmaceutical products takes place in a manner known per se by converting the active compound(s) with the excipients customary in pharmaceutical technology into the desired administration form.

Auxiliaries which can be employed in this connection are, for example, carrier substances, fillers, disintegrants, binders, humectants, lubricants, absorbents and adsorbents, diluents, solvents, cosolvents, emulsifiers, solubilizers, masking flavours, colorants, preservatives, stabilizers, wetting agents, salts to alter the osmotic pressure or buffers. Reference should be made in this connection to Remington's Pharmaceutical Science, 15th ed. Mack Publishing Company, East Pennsylvania (1980). The pharmaceutical formulations may be in solid form, for example as tablets, coated tablets, pills, suppositories, capsules, transdermal systems or in semisolid form, for example as ointments, creams, gels, suppositories, emulsions or in liquid form, for example as solutions, tinctures, suspensions or emulsions.

Auxiliaries in the context of the invention may be, for example, salts, saccharides (mono-, di-, tri-, oligo-, and/or polysaccharides), proteins, amino acids, peptides, fats, waxes, oils, hydrocarbons and derivatives thereof, where the auxiliaries may be of natural origin or may be obtained by synthesis or partial synthesis.

Suitable for oral or peroral administration are in particular tablets, coated tablets, capsules, pills, powders, granules, pastilles, suspensions, emulsions or solutions.

Suitable for parenteral administration are in particular suspensions, emulsions and especially solutions.

Dose and Administration

Based upon standard laboratory techniques known to evaluate compounds useful for the treatment of hyperproliferative disorders and angiogenic disorders, by standard toxicity tests and by standard pharmacological assays for the determination of treatment of the conditions identified in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The present invention further relates to the use of the compounds according to the invention.

The compounds according to the invention can be used for the prophylaxis and therapy of human disorders, in particular tumour disorders.

The compounds according to the invention can be used in particular for inhibiting or reducing cell proliferation and/or cell division and/or to induce apoptosis.

The compounds according to the invention are suitable in particular for the treatment of hyper-proliferative disorders such as, for example,
  psoriasis,
  keloids and other skin hyperplasias,
  benign prostate hyperplasias (BPH),
  solid tumours and
  haematological tumours.

Solid tumours which can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones and the connective tissue and metastases of these tumours.

Haematological tumours which can be treated are, for example,
  multiple myelomas,
  lymphomas or
  leukaemias.

Breast tumours which can be treated are, for example:
  breast carcinomas with positive hormone receptor status
  breast carcinomas with negative hormone receptor status
  Her-2 positive breast carcinomas
  hormone receptor and Her-2 negative breast carcinomas
  BRCA-associated breast carcinomas
  inflammatory breast carcinomas.

Tumours of the respiratory tract which can be treated are, for example,
  non-small-cell bronchial carcinomas such as squamous-cell carcinoma, adenocarcinoma, large-cell carcinoma and
  small-cell bronchial carcinomas.

Tumours of the brain which can be treated are, for example,
  gliomas,
  glioblastomas,
  astrocytomas,
  meningiomas and
  medulloblastomas.

Tumours of the male reproductive organs which can be treated are, for example: prostate carcinomas,
  malignant tumours of the epididymis,
  malignant testicular tumours and
  penis carcinomas.

Tumours of the female reproductive organs which can be treated are, for example:
  endometrial carcinomas
  cervix carcinomas
  ovarial carcinomas
  vaginal carcinomas
  vulvar carcinomas Tumours of the gastrointestinal tract which can be treated are, for example:
  colorectal carcinomas
  anal carcinomas
  stomach carcinomas
  pancreas carcinomas
  oesophagus carcinomas
  gall bladder carcinomas
  carcinomas of the small intestine
  salivary gland carcinomas
  neuroendocrine tumours
  gastrointestinal stroma tumours Tumours of the urogenital tract which can be treated are, for example:
  urinary bladder carcinomas
  kidney cell carcinomas
  carcinomas of the renal pelvis and lower urinary tract Tumours of the eye which can be treated are, for example:
  retinoblastomas
  intraocular melanomas Tumours of the liver which can be treated are, for example:
  hepatocellular carcinomas
  cholangiocellular carcinomas Tumours of the skin which can be treated are, for example:
  malignant melanomas
  basaliomas
  spinaliomas
  Kaposi sarcomas
  Merkel cell carcinomas Tumours of the head and neck which can be treated are, for example:

larynx carcinomas
carcinomas of the pharynx and the oral cavity
carcinomas of midline structures (e.g. NMC, C. A. French, Annu. Rev. Pathol. 2012, 7:247-265)
Sarcomas which can be treated are, for example:
soft tissue sarcomas
osteosarcomas
Lymphomas which can be treated are, for example:
non-Hodgkin lymphomas
Hodgkin lymphomas
cutaneous lymphomas
lymphomas of the central nervous system
AIDS-associated lymphomas
Leukaemias which can be treated are, for example:
acute myeloid leukaemias
chronic myeloid leukaemias
acute lymphatic leukaemias
chronic lymphatic leukaemias
hairy cell leukaemias Advantageously, the compounds according to the invention can be used for the prophylaxis and/or therapy of leukaemias, in particular acute myeloid leukaemias, prostate carcinomas, in particular androgen receptor-positive prostate carcinomas, cervix carcinomas, breast carcinomas, in particular of hormone receptor negative, hormone receptor positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

Particularly advantageously, the compounds according to the invention can be employed for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The compounds according to the invention are also suitable for the prophylaxis and/or therapy of benign hyperproliferative diseases such as endometriosis, leiomyoma and benign prostate hyperplasia.

The compounds according to the invention are also suitable for controlling male fertility.

The compounds according to the invention are also suitable for the prophylaxis and/or therapy of systemic inflammatory diseases, in particular LPS-induced endotoxic shock and/or bacteria-induced sepsis.

The compounds according to the invention are also suitable for the prophylaxis and/or therapy of inflammatory or autoimmune disorders such as:
  pulmonary disorders associated with inflammatory, allergic or proliferative processes: chronic obstructive pulmonary disorders of any origin, especially bronchial asthma; bronchitis of varying origin; all types of restrictive pulmonary disorders, especially allergic alveolitis; all types of pulmonary oedema, especially toxic pulmonary oedema; sarcoidoses and granulomatoses, especially Boeck's disease
  rheumatic disorders/autoimmune diseases/joint disorders associated with inflammatory, allergic or proliferative processes: all types of rheumatic disorders, especially rheumatoid arthritis, acute rheumatic fever, polymyalgia rheumatica; reactive arthritis; inflammatory soft tissue disorders of other origin; arthritic symptoms associated with degenerative joint disorders (arthroses); traumatic arthritides; collagenoses of any origin, e.g. systemic lupus erythematosus, scleroderma, polymyositis, dermatomyositis, Sjögren's syndrome, Still's syndrome, Felty's syndrome
  allergies associated with inflammatory or proliferative processes: all types of allergic reactions, e.g. angioedema, hay fever, insect bite, allergic reactions to drugs, blood derivatives, contrast media etc., anaphylactic shock, urticaria, contact dermatitis
  vessel inflammations (vasculitides): panarterilitis nodosa, arterilitis temporalis, erythema nodosum
  dermatological disorders associated with inflammatory, allergic or proliferative processes: atopic dermatitis; psoriasis; pityriasis rubra pilaris; erythematous disorders induced by various noxae, e.g. radiation, chemicals, burns etc.; bullous dermatoses; lichenoid disorders; pruritus; seborrheic eczema; rosacea; pemphigus vulgaris; erythema exsudativum multiforme; balanitis; vulvitis; hair loss such as alopecia areata; cutaneous T-cell lymphomas
  renal disorders associated with inflammatory, allergic or proliferative processes: nephrotic syndrome; all nephritides
  hepatic disorders associated with inflammatory, allergic or proliferative processes: acute liver cell necrosis; acute hepatitis of varying origin, e.g. viral, toxic, drug-induced; chronic aggressive and/or chronic intermittent hepatitis
  gastrointestinal disorders associated with inflammatory, allergic or proliferative processes: regional enteritis (Crohn's disease); ulcerative colitis; gastritis; reflux oesophagitis; gastroenteritides of other origin, e.g. indigenous sprue
  proctological disorders associated with inflammatory, allergic or proliferative processes: anal eczema; fissures; haemorrhoids; idiopatic proctitis
  ocular disorders associated with inflammatory, allergic or proliferative processes: allergic keratitis, uveitis, iritis; conjunctivitis; blepharitis; optic neuritis; chlorioditis; sympathetic ophthalmia
  ear-nose-throat disorders associated with inflammatory, allergic or proliferative processes: allergic rhinitis, hay fever; otitis externa, e.g. caused by contact eczema, infection etc.; otitis media
  neurological disorders associated with inflammatory, allergic or proliferative processes: cerebral oedema, especially tumour-induced cerebral oedema; multiple sclerosis; acute encephalomyelitis; meningitis; various types of spasms, e.g. West syndrome
  haematological disorders associated with inflammatory, allergic or proliferative processes: acquired haemolytic anaemia; idiopathic thrombocytopenia
  tumour disorders associated with inflammatory, allergic or proliferative processes: acute lymphatic leukaemia; malignant lymphomas; lymphogranulomatoses; lymphosarcomas; extensive metastasization, especially in cases of breast, bronchial and prostate carcinomas
  endocrine disorders associated with inflammatory, allergic or proliferative processes: endocrine orbitopathy; thyreotoxic crisis; de Quervain thyroiditis; Hashimoto thyroiditis; Basedow's disease
  organ and tissue transplantations, graft-versus-host disease
  severe states of shock, e.g. anaphylactic shock, systemic inflammatory response syndrome (SIRS)
  substitution therapy in cases of: congenital primary adrenal insufficiency, e.g. congenital adrenogenital syndrome; acquired primary adrenal insufficiency, e.g. Addison's disease, autoimmune adrenalitis, postinfectious tumours, metastases, etc; congenital secondary adrenal insufficiency, e.g. congenitaler hypopituitarism; acquired secondary adrenal insufficiency, e.g. postinfectious, tumours, etc emesis associated with inflammatory, allergic or proliferative processes, e.g. in combination with a 5-HT3 antagonist for emesis induced by cytostatic drugs pain of inflammatory origin, e.g. lumbago.

The inventive compounds can be combined with one or more active compounds.

Those compounds that can be combined with the inventive compounds can be, for example, those as follows:

The compounds according to the invention are also suitable for the treatment of viral disorders such as, for example, infections caused by papilloma viruses, herpes viruses, Epstein-Barr viruses, hepatitis B or C viruses and human immunodeficiency viruses, including HIV associated kidney diseases.

The inventive compounds are also suitable for the treatment of muscle dystrophia, such as fazioskapulo human muscle dystrophia.

The compounds according to the invention are also suitable for the treatment of atherosklerosis, dyslipidaemia, hypercholesterolaemia, hypertriglyceridaemia, peripheral vascular disorders, cardiovascular disorders, angina pectoris, ischaemia, stroke, insufficiency of the heart, myocardial infarction, angioplastic restenosis, hypertension, thrombosis, adiposity, endotoxemia.

The compounds according to the invention are also suitable for the treatment of neurodegenerative diseases such as, for example, multiple sclerosis, Alzheimer's disease and Parkinson's disease.

These disorders are well characterized in man but also exist in other mammals.

The present application furthermore provides the compounds according to the invention for use as medicaments, in particular for the prophylaxis and/or therapy of tumour disorders.

The present application furthermore provides the compounds according to the invention for the prophylaxis and/or therapy of leukaemias, in particular acute myeloid leukaemias, prostate carcinomas, in particular androgen receptor-positive prostate carcinomas, cervix carcinomas, breast carcinomas, in particular hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides the compounds according to the invention for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The invention furthermore provides the use of the compounds according to the invention for preparing a medicament.

The present application furthermore provides the use of the compounds according to the invention for preparing a medicament for the prophylaxis and/or therapy of tumour disorders.

The present application furthermore provides the use of the compounds according to the invention for preparing a medicament for the prophylaxis and/or therapy of leukaemias, in particular acute myeloid leukaemias, prostate carcinomas, in particular androgen receptor-positive prostate carcinomas, cervix carcinomas, breast carcinomas, in particular of hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides the use of the compounds according to the invention for preparing a medicament for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The present application furthermore provides the use of the compounds according to the invention for the prophylaxis and/or therapy of tumour disorders.

The present application furthermore provides the use of the compounds according to the invention for the prophylaxis and/or therapy of leukaemias, in particular acute myeloid leukaemias, prostate carcinomas, in particular androgen receptor-positive prostate carcinomas, cervix carcinomas, breast carcinomas, in particular hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides the use of the compounds according to the invention for the prophylaxis and/or therapy of leukaemias, in particular acute myeloid leukaemias, prostate carcinomas, in particular androgen receptor-positive prostate carcinomas, breast carcinomas, in particular oestrogen receptor alpha-negative breast carcinomas, melanomas or multiple myelomas.

The present application furthermore provides pharmaceutical formulations in the form of tablets comprising one of the compounds according to the invention for the prophylaxis and/or therapy of leukaemias, in particular acute myeloid leukaemias, prostate carcinomas, in particular androgen receptor-positive prostate carcinomas, cervix carcinomas, breast carcinomas, in particular of hormone receptor-negative, hormone receptor-positive or BRCA-associated breast carcinomas, pancreas carcinomas, kidney cell carcinomas, hepatocellular carcinomas, melanomas and other skin tumours, non-small-cell bronchial carcinomas, endometrial carcinomas and colorectal carcinomas.

The present application furthermore provides pharmaceutical formulations in the form of tablets comprising one of the compounds according to the invention for the prophylaxis and/or therapy of leukaemias, in particular acute myeloid leukaemias, prostate carcinomas, in particular androgen receptor-positive prostate carcinomas, breast carcinomas, in particular oestrogen receptor-alpha-negative breast carcinomas, melanomas or multiple myelomas.

The instant invention further comprises a pharmaceutical formulation that comprises one or more compounds of general formula (I), alone or in combination with one or more further active compounds.

The invention furthermore provides the use of the compounds according to the invention for treating disorders associated with proliferative processes.

The invention furthermore provides the use of the compounds according to the invention for treating benign hyperplasias, inflammatory disorders, autoimmune disorders, sepsis, viral infections, vascular disorders and neurodegenerative disorders.

The compounds according to the invention can be employed by themselves or, if required, in combination with one or more other pharmacologically active substances, as long as this combination does not lead to unwanted and unacceptable side effects. Accordingly, the present invention furthermore provides medicaments comprising a compound according to the invention and one or more further active compounds, in particular for the prophylaxis and/or therapy of the disorders mentioned.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture. A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. The compounds of general formula (I) can be use, respectively applied aloneor in combination together with one or more pharmaceutical active compounds.

Suitable active compounds for combinations which may be mentioned by way of example, without this list being exclusive, are:

131I-chTNT, abarelix, abiraterone, aclarubicin, aflibercept, aldesleukin, alemtuzumab, alitretinoin, altretamine, aminoglutethimide, amrubicin, amsacrine, anastrozole, arglabin, arsenic trioxide, asparaginase, axitinib, azacitidine, basiliximab, belotecan, bendamustine, bevacizumab, bexarotene, bicalutamide, bisantrene, bleomycin, bortezomib, bosutinib, brentuximab, buserelin, busulfan, cabazitaxel, cabozantinib-s-malat, calcium folinate, calcium levofolinate, capecitabine, carboplatin, carfilzomib, carmofur, carmustine, catumaxomab, celecoxib, celmoleukin, cediranib, cetuximab, chlorambucil, chlormadinone, chlormethine, cisplatin, cladribine, clodronic acid, clofarabine, copanlisib, crisantaspase, crizotinib, cyclophosphamide, cyproterone, cytarabine, dacarbazine, dactinomycin, darbepoetin alfa, dasatinib, daunorubicin, debrafenib, decitabine, degarelix, denileukin diftitox, denosumab, deslorelin, dexrazoxane hydrochloride, dibrospidium chloride, docetaxel, doxifluridine, doxorubicin, doxorubicin+estrone, eculizumab, edrecolomab, elliptinium acetate, eltrombopag, endostatin, enocitabine, enzalutamide, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glucarpidase, glutoxim, goserelin, histamine dihydrochloride, histrelin, hydroxycarbamide, I-125 seeds, ibandronic acid, ibritumomab tiuxetan, ibrutinib, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, leucovorin, levamisole, lisuride, lobaplatin, lomustine, lonidamine, masoprocol, mechlorethamine, medroxyprogesterone, megestrol, melphalan, mepitiostane, mercaptopurine, mesna, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, obinutuzumab, ofatumumab, omacetaxine mepesuccinate, omeprazole, oprelvekin, oxaliplatin, ozogamicin, p53 gene therapy, paclitaxel, palifermin, palladium-103 seed, palonosetron hydrochlorid, pamidronic acid, pamidronat disodium, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, pertuzumab, picibanil, pirarubicin, plerixafor, plicamycin, poliglusam, polyestradiol phosphate, polysaccharide-K, pomalidomide, pomatinib, porfimer sodium, pralatrexate, prednimustine, prednisone, procarbazine, quinagolide, radium-223 chloride, raloxifene, raltitrexed, ramucirumab, rasburicase, ranimustine, razoxane, refametinib, regorafenib, risedronic acid, rituximab, romidepsin, romiplostim, roniciclib, ruxolitinib, sargramostim, sipuleucel-T, sizofiran, sobuzoxane, sodium glycididazole, sorafenib, streptozocin, sunitinib, talaporfin, talk, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, I 131 tositumomab, trametinib, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

It is to be understood that the present invention relates also to any combination of the preferred embodiments described above.

A further object of the instant invention is the combination of one or more of the inventive compounds together with a P-TEFb—or CDK9—inhibitor.

A preferred object of the instand invention is the combination of one or more instant compounds together with one or more compounds that are used in cancer therapy, or in radiation therapy.

Generally, the following aims can be pursued with the combination of compounds of the present invention with other agents having a cytostatic or cytotoxic action:

an improved activity in slowing down the growth of a tumour, in reducing its size or even in its complete elimination compared with treatment with an individual active compound;

the possibility of employing the chemotherapeutics used in a lower dosage than in monotherapy;

the possibility of a more tolerable therapy with few side effects compared with individual administration;

the possibility of treatment of a broader spectrum of tumour disorders;

achievement of a higher rate of response to the therapy;

a longer survival time of the patient compared with present-day standard therapy.

The compounds according to the invention can moreover also be employed in combination with radiotherapy and/or surgical intervention.

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

Synthesis Routes for Preparing the Compounds of General Formula (I)

The schemes and general operating procedures below illustrate the general synthetic access to the compounds of general formula (I) according to the invention, without the syntheses of the compounds according to the invention being limited to these.

General Synthesis of the Compounds

The following paragraphs outline a variety of synthetic approaches suitable to prepare compounds of general formula (I), and intermediates useful for their synthesis.

In addition to the routes described below, also other routes may be used to synthesise the target compounds, in accordance with common general knowledge of a person skilled in the art of organic synthesis. The order of transformations exemplified in the following schemes is therefore not intended to be limiting, and suitable synthetic steps from various schemes can be combined to form additional synthetic sequences.

In general, compounds of formula (I) are obtained from the synthesis as mixtures of stereoisomers, e.g. racemates or diastereomers, which provide a 1:1 mixture of epimers at the pyrazoline 4-position. The isomers can be separated by methods known to the person skilled in the art, e.g. by chiral chromatography, by the formation of diastereomeric salts, or by non-chiral chromatography for the separation of diastereomers. Enantiomeric mixtures are preferably separated by chiral chromatography, whereas diastereomers are preferably separated by non-chiral or chiral chromatography. Separations of mixtures of stereoisomers might be carried out on the final compounds or on intermediates. In some cases, protective groups might be introduced to the final compound and removed after separation of stereoisomers.

Compounds of general formula (I) can be readily prepared from compounds of formula (II), according to scheme 1, in which $R^2$, $R^3$, $R^4$, $R^5$ and X are as defined for the compounds of general formula (I), $R^{1A}$ in compounds of formula (IV) represents $R^1$ or a protected derivative of $R^1$, PG is a protective group, and Y is hydroxy, chlorine, bromine or an active ester. If $R^{1A}$ equals $R^1$, compounds of formulae (V) and (I) are identical, and the second deprotection step is obsolete. If $R^{1A}$ is a protected derivative of $R^1$, respective compounds of formula (V) are deprotected to give the corresponding compounds of formula (I). Protective groups and their introduction and cleavage are well-known to a person skilled in the art (see for example T.W. Greene and P.G.M. Wuts in Protective Groups in Organic Synthesis, 4$^{th}$ edition, Wiley 2006). Normally, PG is a carbamate-based protective group; more preferably, PG is allyloxycarbonyl (alloc). Amide coupling reactions are usually carried out in an inert solvent and in presence of a base, preferably at a temperature between 0° C. and the boiling point of the solvent at normal pressure.

Inert solvents are for example halogenated alkanes like dichloromethane, trichloromethane or 1,2-dichloroethane, ethers like dioxane, diethyl ether, tetrahydrofuran or 1,2-dimethoxyethane, or other solvents like acetone, dimethylformamide, dimethylacetamide, N-methylpyrrolidinone or acetonitrile. Preferred solvents are dimethylformamide and acetonitrile.

Carboxylic acid derivatives of formula (IV), in which Y is hydroxy, can be transformed into acid halides or active esters (Molecules 2001, 6(1), 47-51; doi:10.3390/60100047) by well-known methods or activated with coupling reagents [as reviewed for example by Madeleine M. Joullié and Kenneth M. Lassen: Evolution of amide bond formation; ARKIVOC (Gainesville, Fla., United States) 2010, 8, 189-250].

Scheme 1:

Preparation of compounds of general formula (I) from 4-amino-N'-cyano-N,3-diphenyl-4-5-dihydro-1H-pyrazole-1-carboximidamide derivatives of formula (II).

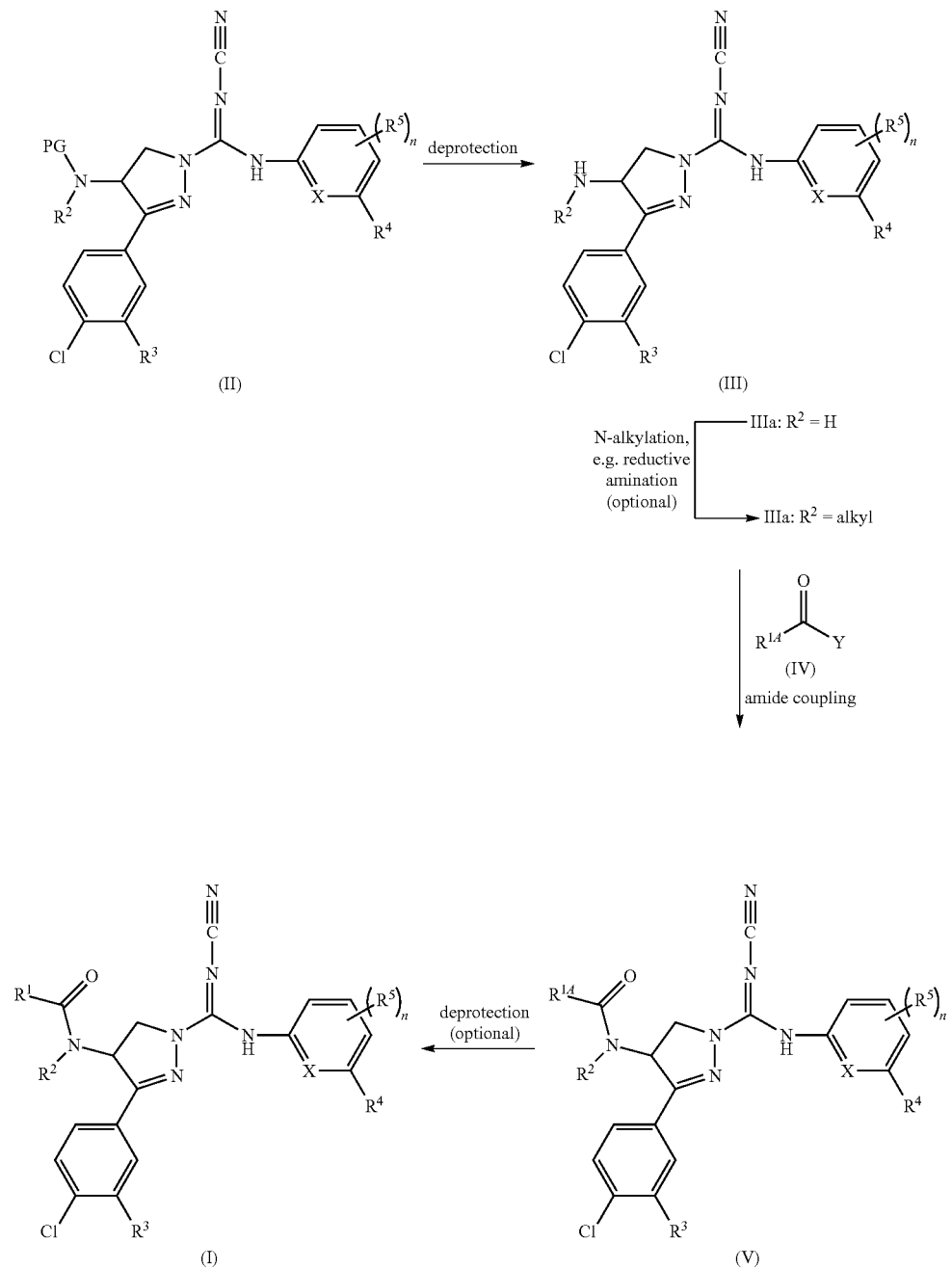

Compounds of formula (V), in which $R^2$ is alkyl, are prepared from the respective alkylated compounds of formula (II), as shown in scheme 1. Alternatively, they are prepared from a compound of formula (III), in which $R^1$ is hydrogen, by reductive alkylation and subsequent amide coupling.

Compounds of formula (II) can be prepared from the corresponding phenoxy derivatives (VI) and arylamines of formula (VII), according to scheme 2. The reaction can be carried out in an inert solvent, as defined above, preferably in tetrahydrofuran at low temperature, e.g. between −78° C. and 0° C. in the presence of a base, for example n-butyllithium, lithium diisopropylamide, or bases which are comparable with regard to basicity and nucleophilicity. Alternatively, reactions of compounds of formula (VI) with compounds of formula (VII) to give compounds of formula (II) can be achieved by heating in inert solvents, preferably ethers, for example 1,4-dioxane, in the presence or absence of a base, such as an aliphatic or aromatic tertiary amine, preferably a tertiary aliphatic amine of the formula $N(C_1$-$C_4$-$alkyl)_3$, at temperatures between room temperature and the boiling point of the solvent.

Scheme 2:
Preparation of compounds of general (II) from phenyl 4-amino-N-cyano-3-phenyl-4,5-dihydro-1H-pyrazole-1-carboximidates of formula (VI) and arylamines of formula (VII).

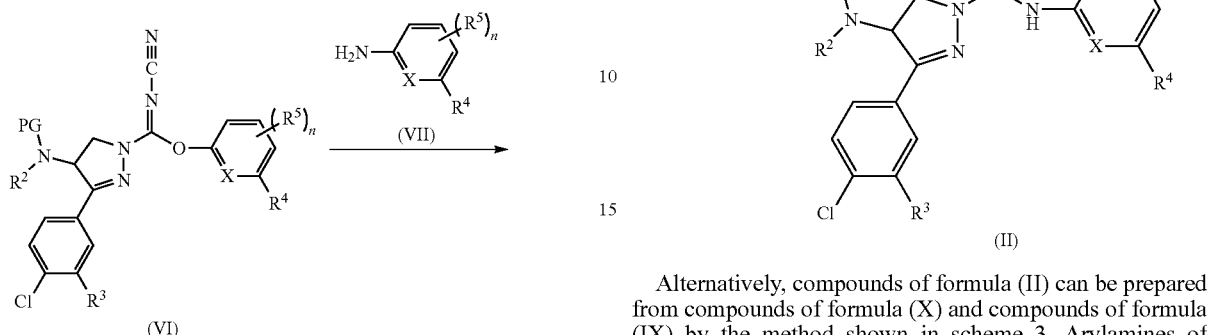

Alternatively, compounds of formula (II) can be prepared from compounds of formula (X) and compounds of formula (IX) by the method shown in scheme 3. Arylamines of formula (VII) are converted into their corresponding isothiocyanates of formula (VIII), which are reacted with sodium cyanoazanide to give the N-cyanothioureas of formula (IX). These are reacted in the presence of a coupling reagent, preferably EDC (1-(3-dimethylaminopropyl)-3-ethylcarbodiimide hydrochloride) with pyrazolines of formula (X) to give compounds of formula (II).

Scheme 3:
Alternative method for the preparation of compounds of formula (II) from 3-phenyl-4,5-dihydro-1H-pyrazol-4-amine derivatives of formula (X) and arylamines of formula (VII).

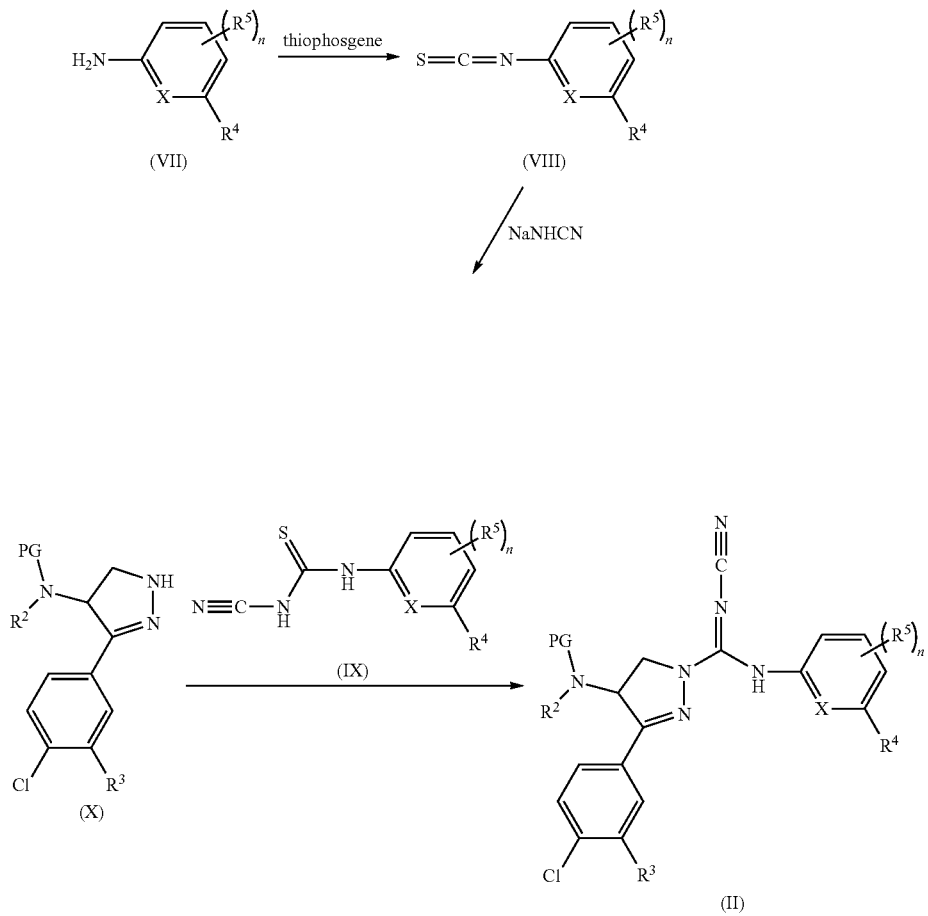

The synthesis of compounds of formula (VI) and (X), as shown in scheme 4, is described in close analogy in WO 2006072350 (e.g. for derivatives of compounds of formula (VI) and (X), in which $R^3$ is hydrogen). The methods can be generally transferred to the preparation of further substituted compounds of formulae (VI) and (X).

Scheme 4: Preparation of compounds of formula (VI) and (X). Compounds of formula (XI) can be prepared by different methods, as described in schemes 5-7. The method is to be chosen based on the substituent $R^2$.

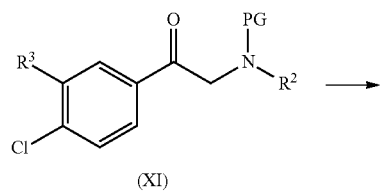

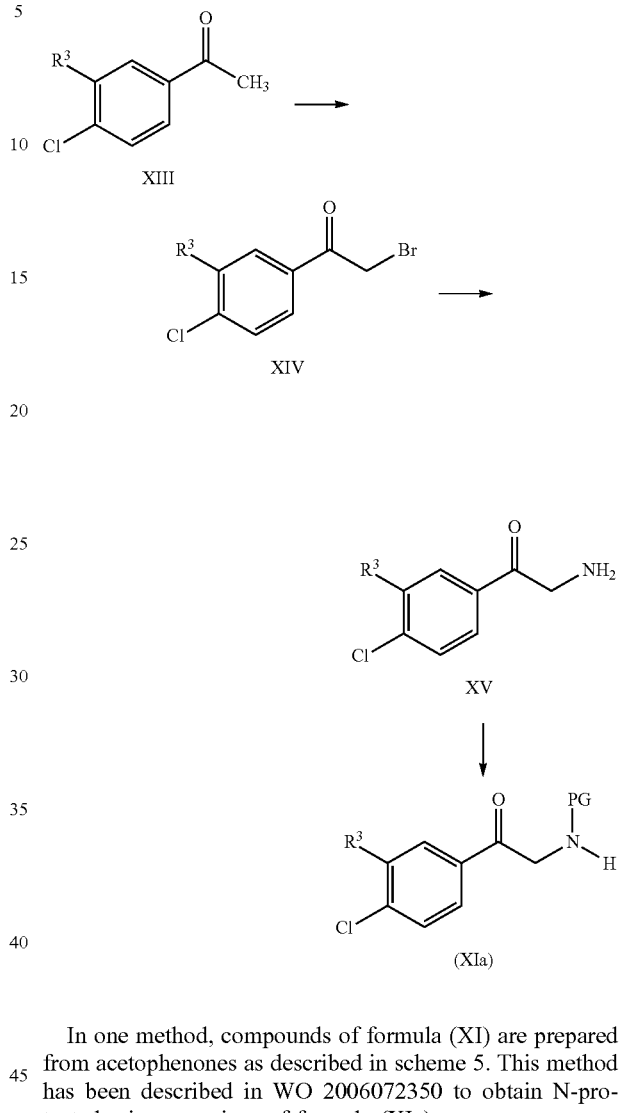

Scheme 5: Preparation of compounds of formula (XI), in which $R^2$ is hydrogen (XIa).

In one method, compounds of formula (XI) are prepared from acetophenones as described in scheme 5. This method has been described in WO 2006072350 to obtain N-protected primary amines of formula (XIa).

Scheme 6: Alternative preparation of compounds of formula (XI) from glycine derivatives.

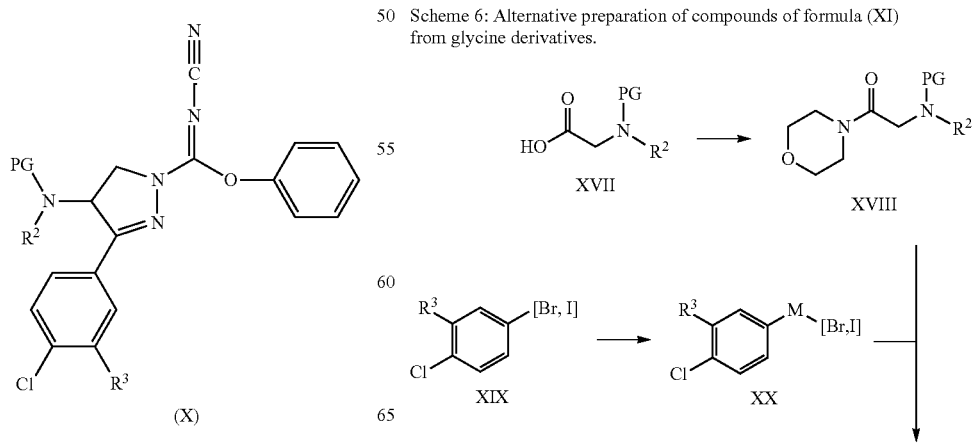

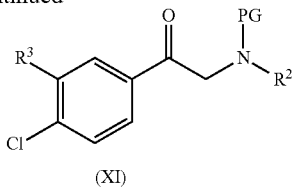

(XI)

Alternatively, compounds of formula (XI) can be prepared from N-protected glycine (XVII) following the route described in scheme 6. Preparation of the glycine amide (XVIII) is followed by the addition of an—optionally in situ generated—aryl metal species (XX), to yield aminoacetophenones of formula (XI), as described similarly in [Org. Process Res. Dev. 2012, 16, 982-1002]. Compounds of formula (XX) are commercially available or can be prepared from aryl halides of formula (XIX) as described, for example in [Org. Process Res. Dev. 2012, 16, 982-1002].

Scheme 7: Preparation of compounds of formula (XI), in which $R^2$ is alkyl.

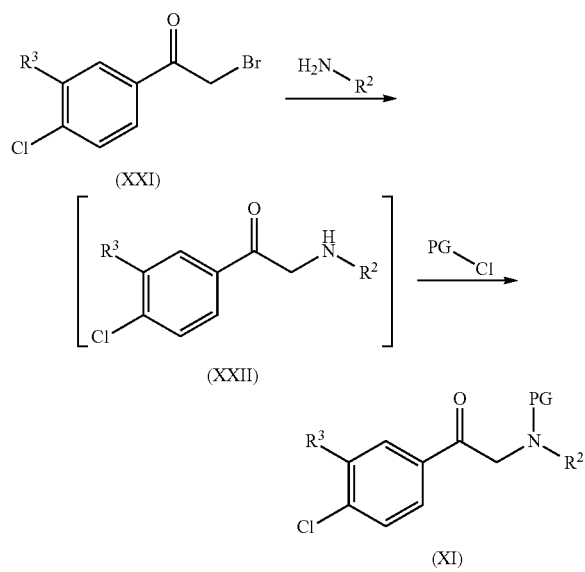

Alternatively, compounds of formula (XI) can be prepared from bromoacetophenones of formula (XXI) by reaction with alkylamines, followed by protection of the resulting secondary amine (XXII), for example with a chloroformate, preferably with allyl chloroformate.

The following table lists the abbreviations used in this paragraph, and in the examples section.

| Abbreviation | Meaning |
| --- | --- |
| anh | anhydrous |
| br. | broad signal (in NMR data) |
| d | day(s) |
| DAD | Diode Array Detector |
| DCM | dichloromethane |
| DEA | diethylamine |
| DME | 1,2-dimethoxyethane |
| DMF | N,N-dimethylformamide |
| DMSO | dimethyl sulfoxide |
| ELSD | Evaporative Light Scattering Detector |
| ESI | electrospray ionisation |
| EtOAc | ethyl acetate |
| Fmoc | [(9H-fluoren-9-ylmethoxy)carbonyl] |
| h | hour |
| HPLC, LC | high performance liquid chromatography |
| m/z | mass-to-charge ratio (in mass spectrum) |
| mc | multiplet centred |
| MeOH | methanol |
| min | minute |
| MS | mass spectroscopy |
| neg | negative |
| NMR | nuclear magnetic resonance |
| PE | petroleum ether |
| pos | positive |
| ppm | chemical shift δ in parts per million |
| Rac | racemic |
| $R_t$ | retention time |
| RT | room temperature |
| SFC | Supercritical Fluid Chromatography |
| THF | tetrahydrofuran |
| TLC | thin layer chromatography |

Other abbreviations have their meanings customary per se to the skilled person.

The various aspects of the invention described in this application are illustrated by the following examples which are not meant to limit the invention in any way.

SPECIFIC EXPERIMENTAL DESCRIPTIONS

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH₂ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only, and are not to be construed as limiting the scope of the invention in any manner. All publications mentioned herein are incorporated by reference in their entirety.

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

Representation of Stereochemistry

All example structures have been synthesized as racemates or 1:1 mixtures of diastereomers, whereas one stereocenter is formed racemic during the synthesis and a second stereocenter is in some cases introduced by amide coupling with an enantiopure carboxylic acid. The racemic stereocenter is indicated as follows:

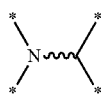

After separation of the stereoisomers, the chiral center with an unknown absolute configuration is indicated as follows:

In this case, the two different stereoisomers are specified by the terms Isomer 1 and Isomer 2.

The cyanoguanidine moiety can formally adopt E- or Z-configuration:

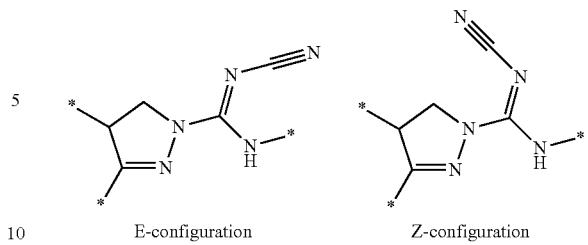

E-configuration        Z-configuration

It is assumed, that at relevant temperatures, the two isomers are present in a fast equilibrium, and cannot be analytically or preparatively distinguished, as similarly described for N,N,N',N'-tetramethylcyanoguanidines (C. Gordon McCarty and Donald M. Wieland: Syn-Anti Isomerization Involving the N-Cyanoimino Group; Tetrahedron Letters No. 22, PP. 1787-1790, 1969). Therefore, any representation of the cyanoguanidine used herein represents both isomers.

EXPERIMENTAL SECTION

Methods:
Method 1:
Column: XBridge C18 IS 5 μm 2.1×30 mm
Eluents: A: 10 mM ammonium bicarbonate pH 10, B: MeCN
Gradient: 0-95% A in 3.10 min, hold @ 95% A to 3.9 min
Flow: 1 mL/min
Method 2:
Column: Acquity UPLC BEH C18 1.7 μm 50×2.1 mm
Eluents: A: $H_2O$+0.2% Vol. $NH_3$ (32%); B: acetonitrile
Gradient: 0-1.6 min 1-99% B; 1.6-2.0 min 99% B
Flow: 0.8 mL/min
Method 3:
Column: XBridge C18 2.5 μm 2.1×20 mm
Eluents: A: 10 mM ammonium bicarbonate pH 10; B: acetonitrile
Gradient: 0% B to 0.18 min, 0-95% B to 2.00 min, hold @ 95% B to 2.60 min
Flow: 1 mL/min
Method 4:
Column: Acquity BEH C18 1.7 μm 2.1×50 mm
Eluents: A: 0.05% aqueous formic acid; B: 0.05% formic acid in acetonitrile
Gradient: 30-80% B to 4.00 min, 80% 5.00 min, 80-50% B to 5.01 min
Flow: 0.4 mL/min
Method 5:
Column: Acquity UPLC BEH C18 1.7 μm 50×2.1 mm
Eluents: A: 0.1% aqueous formic acid; B: acetonitrile
Gradient: 0-1.6 min 1-99% B; 1.6-2.0 min 99% B
Flow: 0.8 mL/min
Method 6:
Column: XBridge BEH C18 2.5 μm 2.1×50 mm
Eluents: A: 10 mM ammonium bicarbonate pH 10; B: acetonitrile
Gradient: 2-98% B in 0.80 min, hold at 98% B to 1.30 min
Flow: 0.8 mL/min
Method 7:
Column: XBridge BEH C18 2.5 μm 2.1×50 mm
Eluents: A: 10 mM ammonium bicarbonate pH 10; B: acetonitrile
Gradient: 2-98% B in 4.00 min, hold @ 98% B to 4.70 min
Flow: 0.8 mL/min Optical Rotation Values:
Instrument: JASCO P2000 Polarimeter; wavelength 589 nm; temperature: 20° C.; integration time 10 s; path length 100 mm.

INTERMEDIATES

Intermediate 1

2-Bromo-1-(3,4-dichlorophenyl)ethanone

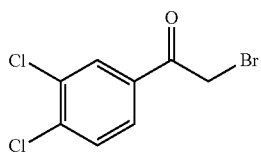 [SMILES: O=C(CBr)c1ccc(Cl)c(Cl)c1]

The reaction was carried out twice on 135 g scale.

To a stirred solution of 3,4-dichloroacetophenone, 135 g (0.714 mol) in acetic acid (675 mL) cooled to 17° C. was added bromine, 37.0 mL (0.722 mol) in acetic acid (360 mL) dropwise. After approximately a third of the bromine had been added no reaction had occurred therefore the reaction mixture was warmed to 25° C. at which point an exotherm to 35° C. occurred. The remainder of the bromine was added and the reaction mixture stirred at room temperature for 30 minutes. The mixture was poured into ice water (1.5 L) while stirring vigorously. The precipitate was collected by filtration and the two batches combined and washed with water. The solid was triturated in diethyl ether (300 mL) to give the desired product 2-bromo-1-(3,4-dichlorophenyl)ethanone, 230 g. The filtrate was washed with brine, dried over magnesium sulfate and concentrated to give a brown oil. The oil was poured into ice/water (1 L) and stirred. The precipitate was collected by filtration to give a second batch of the desired product, 157 g, which were used directly without further purification.

$^1$H NMR (400 MHz, DMSO-d6): δ [ppm]=4.95 (s, 2H), 7.81 (d, 1H), 7.91 (dd, 1H), 8.18 (d, 1H).

LC (method 1): $R_t$ 2.82 min

Intermediate 2

2-Bromo-1-(4-chloro-3-methylphenyl)ethanone

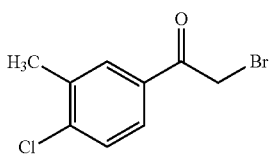

1,2-bromo-1-(4-chloro-3-methylphenyl)ethanone (intermediate 2) was prepared in analogy to intermediate 1, starting from 1-(4-chloro-3-methylphenyl)ethanone.

$^1$H NMR (300 MHz, CDCl$_3$): δ [ppm]=2.44 (s, 3H), 4.40 (s, 2H), 7.45 (d, 1H), 7.73 (dd, 1H), 7.85 (d, 1H).

LCMS (method 2): $R_t$ 1.28 min

Intermediate 3

2-Amino-1-(3,4-dichlorophenyl)ethanone hydrochloride (1:1)

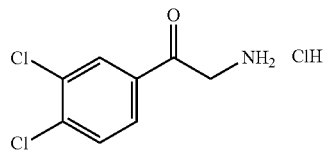 [SMILES: NCC(=O)c1ccc(Cl)c(Cl)c1 ; Cl]

To a stirred solution of 2-bromo-1-(3,4-dichlorophenyl) ethanone (Intermediate 1), 155 g (0.590 mol) in dichloromethane (600 mL) was added a suspension of hexamethylenetetramine, 113 g (0.810 mol) in dichloromethane (600 mL). The reaction mixture was stirred for 2 hours and the resulting precipitate was filtered and washed with dichloromethane (2×150 mL) before being re-suspended in ethanol (1 L). Concentrated hydrochloric acid (600 mL, 37 wt %) was added cautiously and resulted in dissolution of the suspension over 10 minutes. The reaction mixture was stirred for a further 2 hours after which time a precipitate formed, which was collected by filtration, washed with acetone (2×100 mL) and allowed to dry overnight to yield 2-amino-1-(3,4-dichlorophenyl)ethanone hydrochloride, 157 g as a white solid. Excess ammonium chloride was present therefore product was overweight.

$^1$H NMR (400 MHz, DMSO-d6): δ [ppm]=4.57 (s, 2H), 7.84 (d, 1H), 7.94 (dd, 1H), 8.22 (d, 1H).

LC (method 1): $R_t$ 2.13 min

Intermediate 4

2-Amino-1-(4-chloro-3-methylphenyl)ethanone hydrochloride (1:1)

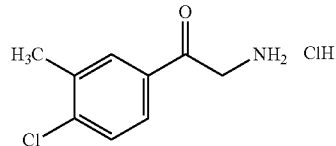

2-amino-1-(4-chloro-3-methylphenyl)ethanone hydrochloride was prepared in analogy to intermediate 3, starting from intermediate 2.

$^1$H NMR (400 MHz, DMSO-d6): δ [ppm]=2.39 (s, 3H), 4.52 (s, 2H), 7.61 (d, 1H), 7.82 (dd, 1H), 8.00 (dd, 1H).

LCMS (method 2): $R_t$ 0.93 min

MS (ESI): [M+H]$^+$=184.0

Intermediate 5

Allyl [2-(3,4-dichlorophenyl)-2-oxoethyl]carbamate

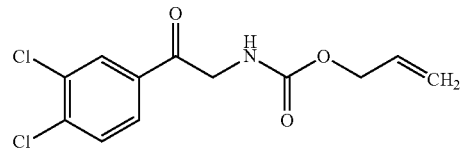 [SMILES: C=CCOC(=O)NCC(=O)c1ccc(Cl)c(Cl)c1]

To a stirred solution of 2-Amino-1-(3,4-dichlorophenyl)ethanone hydrochloride (1:1) (intermediate 3), 116 g (0.480 mol) in water (500 mL) was added allyl chloroformate, 56.5 mL (0.530 mol) in dichloromethane (800 mL). The reaction mixture was cooled to 0° C. and potassium carbonate, 207 g (1.49 mol) in water (1 L) was added dropwise to the reaction mixture over 1 hour. The reaction mixture was allowed to warm to room temperature and was stirred overnight. The reaction mixture was diluted with dichloromethane (500 mL) and the organic phase was extracted and washed with saturated ammonium chloride solution (400 mL) followed by brine solution (500 mL). The organic phase was collected, dried over magnesium sulfate, filtered and the solvent evaporated in vacuo. The crude reaction mixture was purified by dry flash column chromatography (eluent: dichloromethane-heptane 2:1, 3:1, 4:1; dichloromethane; ethyl acetate) to yield allyl [2-(3,4-dichlorophenyl)-2-oxoethyl]carbamate, 120 g (46% over 3 steps) as a white crystalline solid.

$^1$H NMR (400 MHz, CDCl3): δ [ppm]=4.46 (d, 2H), 4.51 (d, 2H), 5.15 (dd, 1H), 5.27 (dd, 1H), 5.81-5.92 (m, 1H), 7.54 (t, 1H), 7.79 (d, 1H), 7.90 (dd, 1H), 8.16 (d, 1H).

LCMS (method 3): R$_t$ 1.59 min
MS (ESI): [M+H]$^+$=288.06

Intermediate 6

Allyl [2-(4-chloro-3-methylphenyl)-2-oxoethyl]carbamate

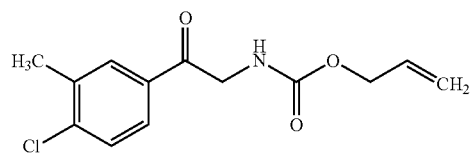 [SMILES: C=CCOC(=O)NCC(=O)c1ccc(Cl)c(C)c1]

Allyl [2-(4-chloro-3-methylphenyl)-2-oxoethyl]carbamate was prepared in analogy to intermediate 5, starting from intermediate 4.

$^1$H NMR (400 MHz, CDCl3): δ [ppm]=2.44 (s, 3H), 4.62 (d, 2H), 4.67 (d, 2H), 5.23 (dd, 1H), 5.33 (dd, 1H), 5.72 (br s, 1H), 5.94 (ddt, 1H), 7.45 (d, 1H), 7.71 (dd, 1H), 7.83 (dd, 1H).

LCMS (method 2): R$_t$ 1.19 min
MS (ESI): [M+H]$^+$=268.0

Intermediate 7

Rac-allyl [3-(3,4-dichlorophenyl)-4,5-dihydro-1H-pyrazol-4-yl]carbamate

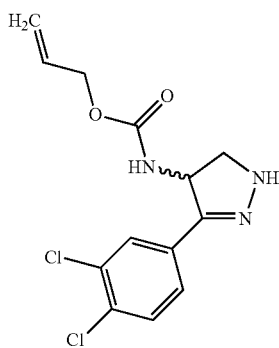 [SMILES: C=CCOC(=O)NC1CNN=C1c1ccc(Cl)c(Cl)c1]

Step 1

Allyl [3-(3,4-dichlorophenyl)-3-oxoprop-1-en-2-yl]carbamate

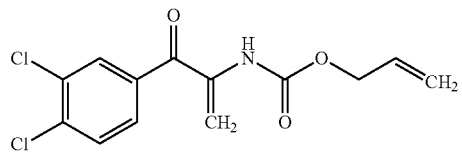 [SMILES: C=CCOC(=O)NC(=C)C(=O)c1ccc(Cl)c(Cl)c1]

To a stirred suspension of allyl [2-(3,4-dichlorophenyl)-2-oxoethyl]carbamate (intermediate 5), 50.0 g (0.174 mol) in ethanol (390 mL) was added formaldehyde solution, 20 mL (0.261 mol, 37 wt % in water) followed by the dropwise addition of piperidine, 26 mL (0.261 mol) in ethanol (130 mL) over 30 minutes. The reaction mixture was stirred overnight and thin layer chromatography indicated consumption of the starting material. The solvent was removed by evaporation to yield an orange oil, no further purification was performed and the crude product was used in the subsequent step as isolated.

Step 2

Rac-allyl [3-(3,4-dichlorophenyl)-4,5-dihydro-1H-pyrazol-4-yl]carbamate

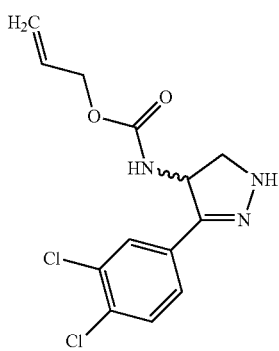 [SMILES: C=CCOC(=O)NC1CNN=C1c1ccc(Cl)c(Cl)c1]

To a solution of allyl [3-(3,4-dichlorophenyl)-3-oxoprop-1-en-2-yl]carbamate, (~0.174 mol) in ethanol (480 mL) was added hydrazine monohydrate, 29.6 mL (0.609 mol) and the reaction mixture was heated to reflux for 2.5 hours. The reaction mixture was allowed to cool to room temperature then concentrated before pouring over ice cooled saturated ammonium chloride solution (300 mL). The crude product was extracted with ethyl acetate (1.5 L) and the organic layers were combined and washed with brine solution (300 mL). The collected organic phase was dried over magnesium sulfate, filtered and the solvent evaporated to yield rac-allyl [3-(3,4-dichlorophenyl)-4,5-dihydro-1H-pyrazol-4-yl]carbamate, 50.0 g (91%) as a pale yellow solid.

$^1$H NMR (400 MHz, DMSO-d6): δ [ppm]=3.24 (m partially masked by H$_2$O peak), 3.59 (td, 1H), 4.39-4.54 (m, 2H), 5.08-5.25 (m, 3H), 5.79-5.90 (m, 1H), 7.52 (dd, 1H), 7.57 (br s, 1H), 7.59 (d, 1H), 7.68 (d, 1H), 7.84 (d, 1H).

LCMS (method 3): R$_t$ 1.55 min
MS (ESI): [M+H]$^+$=314.1

Intermediate 8

Rac-allyl [3-(4-chloro-3-methylphenyl)-4,5-dihydro-1H-pyrazol-4-yl]carbamate

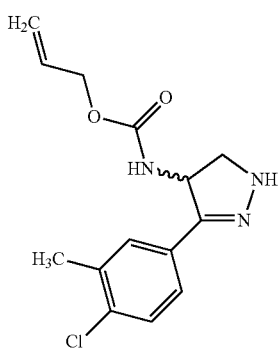 [SMILES: C=CCOC(=O)NC1CNN=C1c1ccc(Cl)c(C)c1]

Rac-allyl [3-(4-chloro-3-methylphenyl)-4,5-dihydro-1H-pyrazol-4-yl]carbamate was prepared in analogy to intermediate 7, starting from intermediate 6.

$^1$H NMR (400 MHz, DMSO-d6): δ [ppm]=2.28 (s, 3H), 3.20 (dd, 1H), 3.55 (td, 1H), 4.45 (qd, 2H), 5.11 (d, 1H), 5.14-5.24 (m, 2H), 5.85 (ddt, 1H), 3.30-3.39 (m, 3H), 7.52 (s, 1H), 7.80 (d, 1H).

LCMS (method 2): R$_t$ 1.14 min
MS (ESI): [M+H]$^+$=294.2

Intermediate 9

Rac-phenyl 4-{[(allyloxy)carbonyl]amino}-N-cyano-3-(3,4-dichlorophenyl)-4,5-dihydro-1H-pyrazole-1-carboximidate

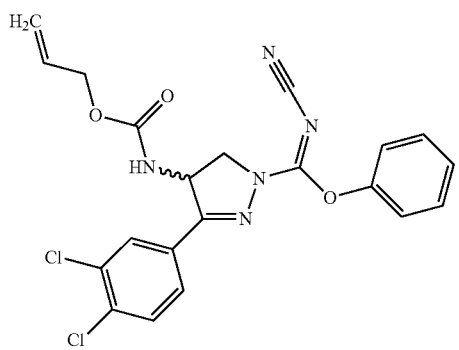 [SMILES: C=CCOC(=O)NC1CN(/C(=N\C#N)Oc2ccccc2)N=C1c1ccc(Cl)c(Cl)c1]

To a stirred suspension of rac-allyl [3-(3,4-dichlorophenyl)-4,5-dihydro-1H-pyrazol-4-yl]carbamate (intermediate 7), 50.0 g (0.159 mol) in 2-propanol (860 mL) was added diphenyl N-cyanocarbonimidate, 38.0 g (0.159 mol). The reaction mixture was heated to reflux at which point the suspension dissolved into solution after a further 10 minutes at reflux a white precipitate formed. The reaction mixture was stirred at reflux for a further 1 hour before allowing to slowly cool to room temperature overnight. The precipitate was filtered, washing with diethyl ether (2×250 mL) and the resulting white solid was allowed to dry to yield rac-phenyl 4-{[(allyloxy)carbonyl]amino}-N-cyano-3-(3,4-dichlorophenyl)-4,5-dihydro-1H-pyrazole-1-carboximidate as a white solid, 48.6 g (67%).

$^1$H NMR (400 MHz, DMSO-d6): δ [ppm]=4.13 (apparent d, 1H), 4.47 (m, 3H), 5.14 (dd, 2H), 5.51-5.63 (m, 1H), 5.79-5.90 (m, 1H), 7.23 (d, 2H), 7.30 (t, 1H), 7.45 (t, 2H), 7.79 (br m, 2H), 7.97 (br s, 1H), 8.19 (d, 1H).

LCMS (method 3): R$_t$ 1.75 min
MS (ESI): [M+H]$^+$=458.0

Intermediate 10

Rac-phenyl 4-{[(allyloxy)carbonyl]amino}-3-(4-chloro-3-methylphenyl)-N-cyano-4,5-dihydro-1H-pyrazole-1-carboximidate

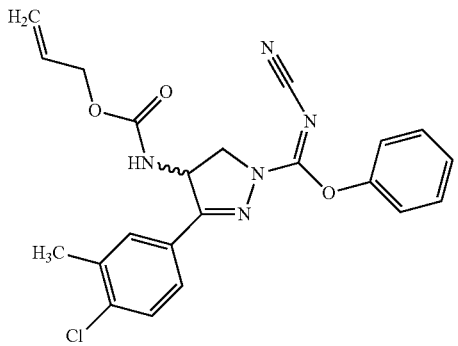 [SMILES: C=CCOC(=O)NC1CN(/C(=N\C#N)Oc2ccccc2)N=C1c1ccc(Cl)c(C)c1]

Rac-phenyl 4-{[(allyloxy)carbonyl]amino}-3-(4-chloro-3-methylphenyl)-N-cyano-4,5-dihydro-1H-pyrazole-1-carboximidate was prepared in analogy to intermediate 9, starting from intermediate 8.

$^1$H NMR (400 MHz, CDCl3): δ [ppm]=2.18 (s, 3H), 4.30 (d, 2H), 4.64 (d, 2H), 5.24 (d, 1H), 5.34 (d, 1H), 5.60-5.70 (m, 1H), 5.94 (ddt, 1H), 6.89-7.35 (m, 7H), 7.48 (dd, 1H), 7.54 (d, 1H).

LCMS (method 2): $R_t$ 1.30 min
MS (ESI): [M+H]$^+$=438.2

Intermediate 11

Rac-phenyl 4-{[(allyloxy)carbonyl]amino}-3-(4-chloro-3-methylphenyl)-N-cyano-4,5-dihydro-1H-pyrazole-1-carboximidate

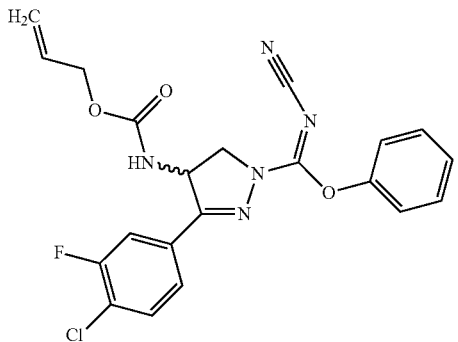 [SMILES: C=CCOC(=O)NC1CN(/C(=N\C#N)Oc2ccccc2)N=C1c1ccc(Cl)c(F)c1]

Rac-phenyl 4-{[(allyloxy)carbonyl]amino}-3-(4-chloro-3-methylphenyl)-N-cyano-4,5-dihydro-H-pyrazole-1-carboximidate was prepared as described for intermediate 9, starting from 1-(4-chloro-3-fluorophenyl)ethanone.

$^1$H-NMR (400 MHz, DMSO-d$_6$): d [ppm]=4.17 (d, 1H), 4.49-4.60 (m, 3H), 5.10-5.27 (m, 2H), 5.52-5.67 (m, 1H), 5.79-5.96 (m, 1H), 7.26 (d, 2H), 7.30-7.38 (m, 1H), 7.44-7.54 (m, 2H), 7.69 (br. s., 1H), 7.79 (d, 2H), 8.21 (d, 1H).
MS (ESI): [M+H]$^+$=442

Intermediate 12

Rac-allyl [1-{N'-cyano-N-[3-(difluoromethoxy)phenyl]carbamimidoyl}-3-(3,4-dichlorophenyl)-4,5-dihydro-1H-pyrazol-4-yl]carbamate

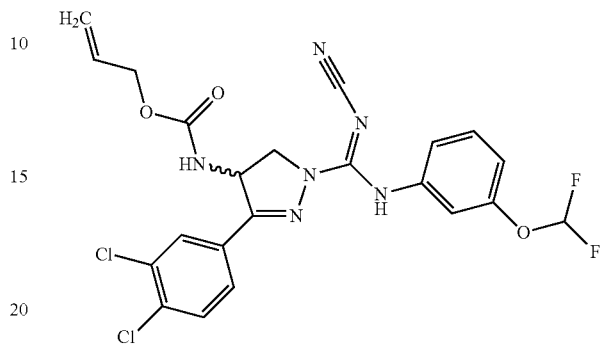

To a stirred solution of m-difluoromethoxy aniline, 8.20 mL (65.5 mmol) in anhydrous tetrahydrofuran (100 mL) at −78° C. was added n-butyl lithium, 33.0 mL (65.5 mmol, 2 M in hexane) dropwise maintaining the reaction temperature below −65° C. during the addition. The reaction mixture was stirred for 1 hour at −78° C. before Rac-phenyl 4-{[(allyloxy)carbonyl]amino}-N-cyano-3-(3,4-dichlorophenyl)-4,5-dihydro-1H-pyrazole-1-carboximidate (intermediate 9), 10.0 g (21.8 mmol) in anhydrous tetrahydrofuran (600 mL) was added dropwise maintaining the reaction temperature below −65° C. The reaction mixture was stirred for 2 hours at −78° C. before slowly pouring over saturated ammonium chloride solution (700 mL). The crude product was extracted into ethyl acetate (700 mL) and the organic layers were combined and washed with brine solution (350 mL). The collected organic phase was dried over magnesium sulfate, filtered and the solvent evaporated to yield an off-white crude solid. The crude solid was precipitated from a minimum volume of ethyl acetate and filtered, washing with diethyl ether to yield rac-allyl [1-{N'-cyano-N-[3-(difluoromethoxy)phenyl]carbamimidoyl}-3-(3,4-dichlorophenyl)-4,5-dihydro-1H-pyrazol-4-yl]carbamate, 7.6 g (67%) as a white solid.

$^1$H NMR (400 MHz, DMSO-d6): δ [ppm]=4.08 (dd, 1H), 4.36-4.53 (m, 3H), 5.11 (dd, 1H), 5.17 (dd, 1H), 5.50-5.59 (m, 1H), 5.77-5.90 (m, 1H), 6.99 (dd, 1H), 7.16 (t, 1H), 7.21 (t, 1H), 7.23 (dd, 1H), 7.39 (t, 1H), 7.73-7.81 (m, 2H), 8.15 (d, 1H), 8.17 (d, 1H), 9.79 (br s, 1H).

LCMS (method 3): $R_t$ 1.78 min
MS (ESI): [M+H]$^+$=523.2

The following intermediates were prepared according to the method described for intermediate 12, by addition of the respective aniline derivatives to intermediate 9, intermediate 10 or intermediate 11.

| Intermediate No | Structure IUPAC name | Analytical data |
|---|---|---|
| 13 | 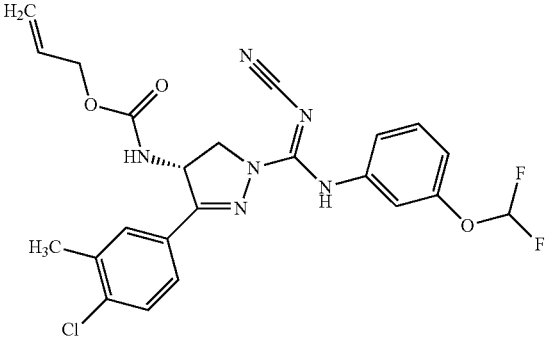<br>Rac-allyl [3-(4-chloro-3-methylphenyl)-1-{N'-cyano-N-[3-(difluoromethoxy)phenyl]carbamimidoyl}-4,5-dihydro-1H-pyrazol-4-yl]carbamate | LMCS (method 2):<br>$R_t$ 1.35 min<br>MS (ESI):<br>$[M + H]^+ = 503.2$ |
| 14 | 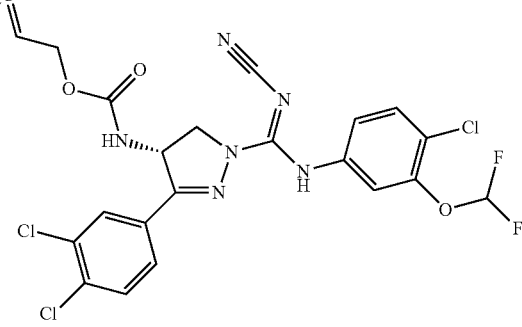<br>Rac-allyl [1-{N-[4-chloro-3-(difluoromethoxy)phenyl]-N'-cyanocarbamimidoyl}-3-(3,4-dichlorophenyl)-4,5-dihydro-1H-pyrazol-4-yl]carbamate | LMCS (method 2):<br>$R_t$ 1.40 min<br>MS (ESI):<br>$[M + H]^+ = 557.2$ |
| 15 | 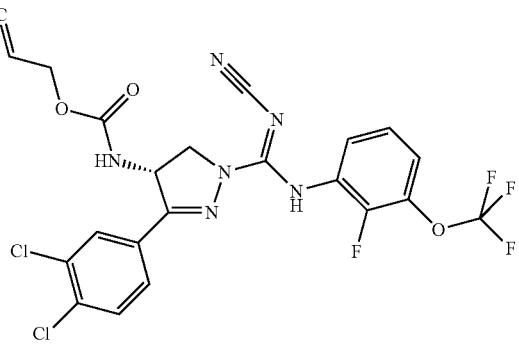<br>Rac-allyl [1-{N'-cyano-N-[2-fluoro-3-(trifluoromethoxy)phenyl]carbamimidoyl}-3-(3,4-dichlorophenyl)-4,5-dihydro-1H-pyrazol-4-yl]carbamate | LMCS (method 2):<br>$R_t$ 1.24 min<br>MS (ESI):<br>$[M + H]^+ = 559.2$ |

-continued

| Intermediate No | Structure IUPAC name | Analytical data |
|---|---|---|
| 16 | 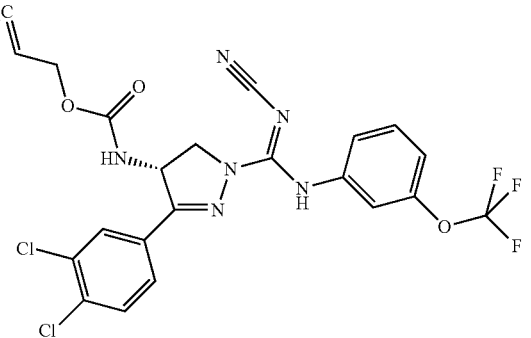<br>Rac-allyl [1-{N'-cyano-N-[3-(trifluoromethoxy)phenyl]carbamimidoyl}-3-(3,4-dichlorophenyl)-4,5-dihydro-1H-pyrazol-4-yl]carbamate | LMCS (method 2):<br>$R_t$ 1.43 min<br>MS (ESI):<br>$[M + H]^+ = 541.1$ |
| 17 | 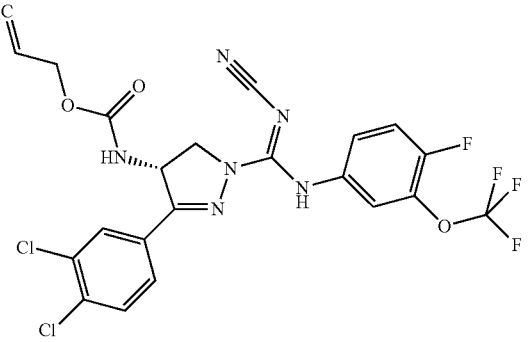<br>Rac-allyl [1-{N'-cyano-N-[4-fluoro-3-(trifluoromethoxy)phenyl]carbamimidoyl}-3-(3,4-dichlorophenyl)-4,5-dihydro-1H-pyrazol-4-yl]carbamate | LMCS (method 2):<br>$R_t$ 1.35 min<br>MS (ESI):<br>$[M + H]^+ = 559.0$ |
| 18 | 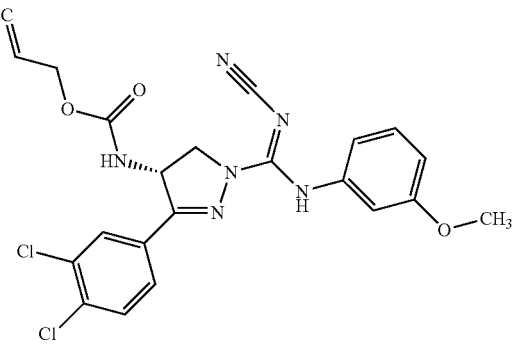<br>Rac-allyl {1-[N'-cyano-N-(3-methoxyphenyl)carbamimidoyl]-3-(3,4-dichlorophenyl)-4,5-dihydro-1H-pyrazol-4-yl}carbamate | LMCS (method 2):<br>$R_t$ 1.33 min<br>MS (ESI):<br>$[M + H]^+ = 487.1$ |

| Intermediate No | Structure IUPAC name | Analytical data |
|---|---|---|
| 19 | Rac-allyl [1-(N'-cyano-N-{3-[2-(dimethylamino)ethoxy]phenyl}carbamimidoyl)-3-(3,4-dichlorophenyl)-4,5-dihydro-1H-pyrazol-4-yl]carbamate | LMCS (method 2): $R_t$ 1.31 min<br>MS (ESI):<br>$[M + H]^+$ = 544.0 |
| 20 | Rac-allyl [1-{N'-cyano-N-[6-(difluoromethoxy)pyridin-2-yl]carbamimidoyl}-3-(3,4-dichlorophenyl)-4,5-dihydro-1H-pyrazol-4-yl]carbamate | LMCS (method 3): $R_t$ 1.05 min<br>MS (ESI):<br>$[M + H]^+$ = 524.1 |
| 21 | Rac-allyl [1-{N'-cyano-N-[3-(2,2,2-trifluoroethyl)phenyl]carbamimidoyl}-3-(3,4-dichlorophenyl)-4,5-dihydro-1H-pyrazol-4-yl]carbamate | LMCS (method 2): $R_t$ 1.39 min<br>MS (ESI):<br>$[M + H]^+$ = 539.1 |

-continued

| Intermediate No | Structure IUPAC name | Analytical data |
|---|---|---|
| 22 | 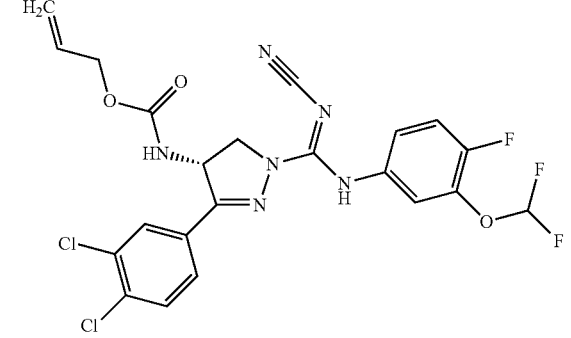<br>Rac-allyl [1-{N'-cyano-N-[3-(difluoromethoxy)-4-fluorophenyl]carbamimidoyl}-3-(3,4-dichlorophenyl)-4,5-dihydro-1H-pyrazol-4-yl]carbamate | LMCS (method 2):<br>$R_t$ 1.32 min<br>MS (ESI):<br>$[M + H]^+$ = 540.8 |
| 23 | 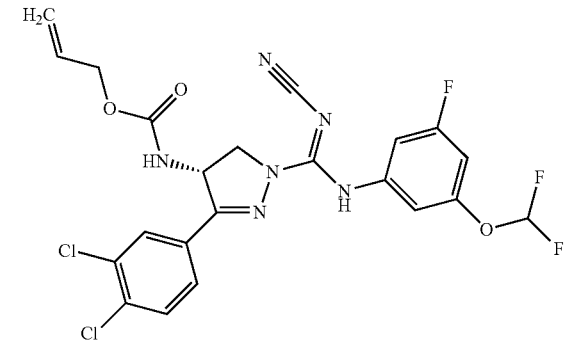<br>Rac-allyl [1-{N'-cyano-N-[3-(difluoromethoxy)-5-fluorophenyl]carbamimidoyl}-3-(3,4-dichlorophenyl)-4,5-dihydro-1H-pyrazol-4-yl]carbamate | LMCS (method 2):<br>$R_t$ 1.29 min<br>MS (ESI):<br>$[M + H]^+$ = 541.2 |
| 24 | 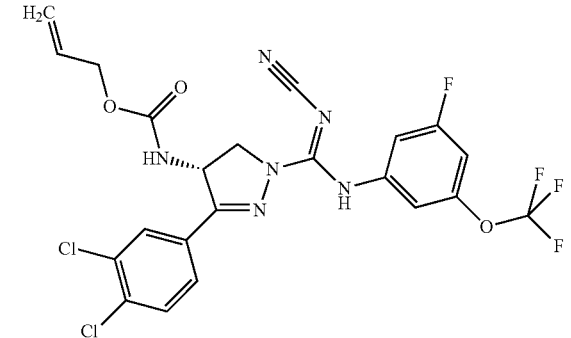<br>Rac-allyl [1-{N'-cyano-N-[3-fluoro-5-(trifluoromethoxy)phenyl]carbamimidoyl}-3-(3,4-dichlorophenyl)-4,5-dihydro-1H-pyrazol-4-yl]carbamate | LMCS (method 2):<br>$R_t$ 1.33 min<br>MS (ESI):<br>$[M + H]^+$ = 559.2 |

-continued

| Intermediate No | Structure IUPAC name | Analytical data |
|---|---|---|
| 25 | Rac-allyl [1-{N'-cyano-N-[2-(pyrrolidin-1-ylmethyl)-5-(trifluoromethoxy)phenyl]carbamimidoyl}-3-(3,4-dichlorophenyl)-4,5-dihydro-1H-pyrazol-4-yl]carbamate | LMCS (method 2): $R_t$ 1.61 min MS (ESI): $[M + H]^+$ = 608.2 |
| 26 | Rac-allyl [1-{N'-cyano-N-[2-(trifluoromethoxy)-5-(trifluoromethyl)phenyl]carbamimidoyl}-3-(3,4-dichlorophenyl)-4,5-dihydro-1H-pyrazol-4-yl]carbamate | LMCS (method 2): $R_t$ 1.30 min MS (ESI): $[M + H]^+$ = 608.7 |
| 27 | Rac-allyl [1-(N'-cyano-N-{2-[2-(pyrrolidin-1-yl)ethoxy]-5-(trifluoromethyl)phenyl}carbamimidoyl)-3-(3,4-dichlorophenyl)-4,5-dihydro-1H-pyrazol-4-yl]carbamate | LMCS (method 2): $R_t$ 1.44 min MS (ESI): $[M + H]^+$ = 637.8 |

| Intermediate No | Structure IUPAC name | Analytical data |
|---|---|---|
| 28 | 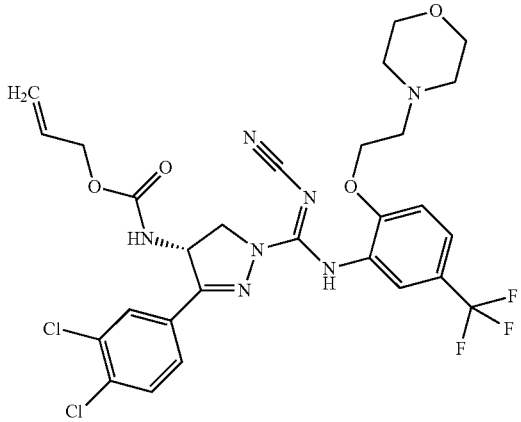

Rac-allyl [1-(N'-cyano-N-{2-[2-(morpholin-4-yl)ethoxy]-5-(trifluoromethyl)phenyl}carbamimidoyl}-3-(3,4-dichlorophenyl)-4,5-dihydro-1H-pyrazol-4-yl]carbamate | LMCS (method 2): R$_t$ 1.33 min MS (ESI): [M + H]$^+$ = 653.8 |
| 29 | 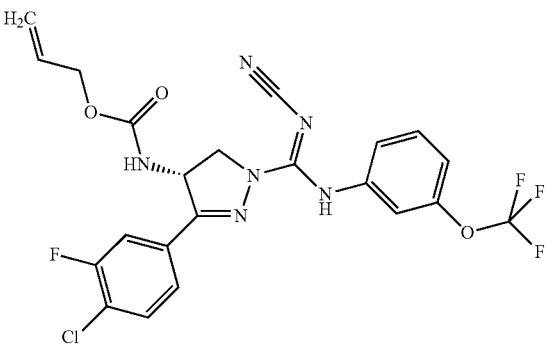

Rac-allyl [3-(4-chloro-3-fluorophenyl)-1-{N'-cyano-N-[3-(trifluoromethoxy)phenyl]carbamimidoyl}-4,5-dihydro-1H-pyrazol-4-yl]carbamate | LMCS (method 2): R$_t$ 1.33 min MS (ESI): [M + H]$^+$ = 524.8 |

Intermediate 30

Rac-allyl [1-{N'-cyano-N-[5-(difluoromethoxy)-2-methoxyphenyl]carbamimidoyl}-3-(3,4-dichlorophenyl)-4,5-dihydro-1H-pyrazol-4-yl]carbamate

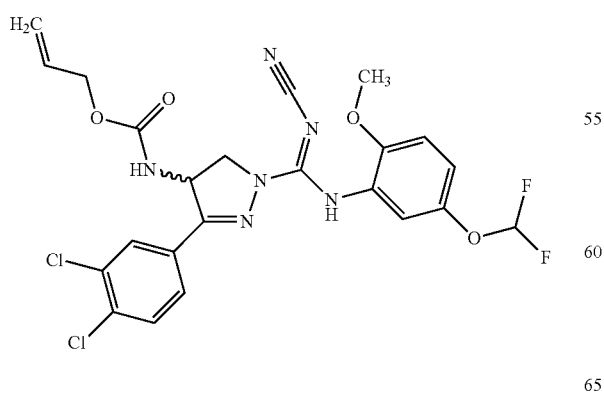

Intermediate 30 was prepared from intermediate 44 and intermediate 7 according to the scheme below.

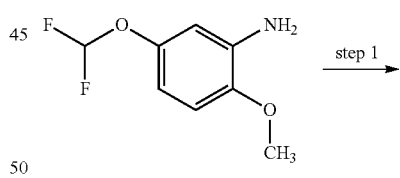

intermediate 44 step 1 → step 2 →

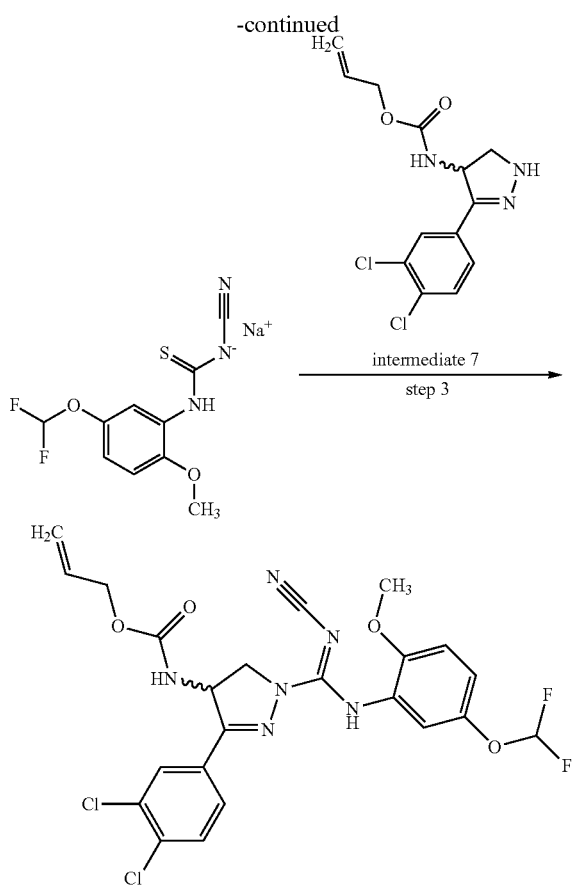

Step 1

To a solution of 5-(difluoromethoxy)-2-methoxyaniline (intermediate 44), 5.17 g (27.3 mmol) in dichloromethane (100 mL) was added an aqueous solution of sodium hydrogen carbonate 100 mL. Thiophosgene 2.2 mL (28.7 mmol) was added dropwise to the vigorously stirred mixture at room temperature and stirring continued for 1 hour. The reaction mixture was diluted with dichloromethane and washed with water. The aqueous layer was washed with further dichloromethane and the combined organic extracts were washed with brine, dried over sodium sulfate and concentrated to give 4-(difluoromethoxy)-2-isothiocyanato-1-methoxybenzene as a dark red oil 5.59 g (89%).

$^1$H NMR (400 MHz, CDCl$_3$): δ [ppm]=3.90 (s, 3H), 6.40 (t, 1H), 6.85 (d, 1H), 6.91 (d, 1H), 7.01 (dd, 1H)

UPLC (method 6) 0.89 min

Step 2

A solution of 4-(difluoromethoxy)-2-isothiocyanato-1-methoxybenzene 5.59 g (24.2 mmol) and mono sodium cyanamide 1.55 g (24.2 mmol) in ethanol 50 mL was stirred at reflux for 1 hour. The suspension was allowed to cool and concentrated in vacuo. The resulting residue was triturated with diethyl ether to give a light purple solid which was collected by filtration and washed with further diethyl ether to give sodium cyano {[5-(difluoromethoxy)-2-methoxyphenyl]carbamothioyl}azanide as a light purple solid 5.79 g (81%).

$^1$H NMR (400 MHz, DMSO-d$_6$): δ [ppm]=3.80 (s, 3H), 6.65 (dd, 1H), 6.92 (d, 1H), 6.99 (t, 1H), 7.87 (s, 1H), 8.20 (d, 1H)

UPLC (method 6) 0.56 min

MS (ESI): [M−Na]$^-$=272.01

Step 3

To a solution of rac-allyl (3-[3,4-dichlorophenyl]-4,5-dihydro-1H-pyrazol-4-yl)carbamate (intermediate 7) 8.16 g (27.6 mmol) in N,N-dimethylformamide 100 mL was added N-(3-dimethylaminopropyl)-N'-ethylcarbodiimide hydrochloride 7.07 g (36.9 mmol) and sodium cyano {[5-(difluoromethoxy)-2-methoxyphenyl]carbamothioyl}azanide (intermediate 44) 5.79 g (18.4 mmol) were added sequentially. The dark brown solution was stirred at room temperature overnight. The solution was diluted with ethyl acetate 50 mL and washed with 10% citric acid aqueous solution 25 mL then brine (3×25 mL). The organic layer was dried over sodium sulfate and concentrated to a brown solid. Trituration with dichloromethane and diethyl ether gave a solid which was collected by filtration and washed with further diethyl ether to give rac-allyl [1-{N'-cyano-N-[5-(difluoromethoxy)-2-methoxyphenyl]carbamimidoyl}-3-(3,4-dichlorophenyl)-4,5-dihydro-1H-pyrazol-4-yl]carbamate as a cream solid 3.66 g (36%).

$^1$H NMR (400 MHz, DMSO-d$_6$): δ [ppm]=3.79 (s, 3H), 3.93 (dd, 1H), 4.31 (t, 1H), 4.43-4.49 (m, 2H), 5.10-5.19 (m, 1H), 5.49-5.57 (m, 1H), 5.79-5.89 (m, 1H), 7.08-7.11 (m, 3H), 7.13 (s, 1H), 7.74-7.75 (m, 2H), 8.14 (s, 1H), 8.15-8.18 (m, 2H), 9.53 (br s, 1H)

UPLC (method 6) 0.90 min

MS (ESI): [M−Na]$^-$=553.13

Intermediate 31

Rac-allyl [1-{N'-cyano-N-[2-methoxy-5-(trifluoromethyl)phenyl]carbamimidoyl}-3-(3,4-dichlorophenyl)-4,5-dihydro-1H-pyrazol-4-yl]carbamate

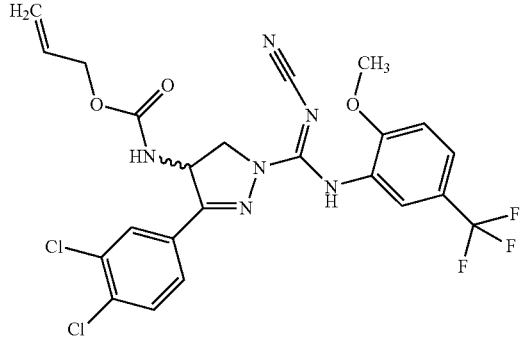 [SMILES: C=CCOC(=O)NC1CN(/C(=N\C#N)Nc2cc(C(F)(F)F)ccc2OC)N=C1c1ccc(Cl)c(Cl)c1]

Intermediate 31 was prepared as described for intermediate 30 starting from 2-methoxy-5-(trifluoromethyl)aniline and intermediate 7, to obtain rac-allyl [1-{N'-cyano-N-[2-methoxy-5-(trifluoromethyl)phenyl]carbamimidoyl}-3-(3,4-dichlorophenyl)-4,5-dihydro-1H-pyrazol-4-yl]carbamate, in 42% over three steps.

$^1$H NMR (400 MHz, DMSO-d$_6$): δ [ppm]=3.88 (s, 3H), 3.90-3.96 (m, 1H), 4.31 (t, 1H), 4.43-4.51 (m, 2H), 5.10-5.19 (m, 1H), 5.51-5.58 (m, 1H), 5.80-5.89 (m, 1H), 7.26 (d, 1H), 7.57 (d, 1H), 7.65 (dd, 1H), 7.73-7.78 (m, 2H), 8.14 (s, 1H), 8.17 (d, 1H), 9.62 (br s, 1H)

UPLC (method 6): R$_t$ 0.92 min

MS (ESI): [M−H]$^-$=553.09

Intermediate 32

Rac-allyl [3-(3,4-dichlorophenyl)-4,5-dihydro-1H-pyrazol-4-yl]ethylcarbamate

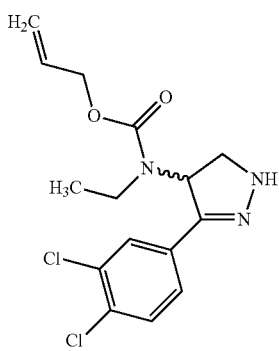 [SMILES: C=CCOC(=O)N(CC)C1CNN=C1c1ccc(Cl)c(Cl)c1]

Intermediate 32 was synthesized starting from intermediate 2 following the scheme below.

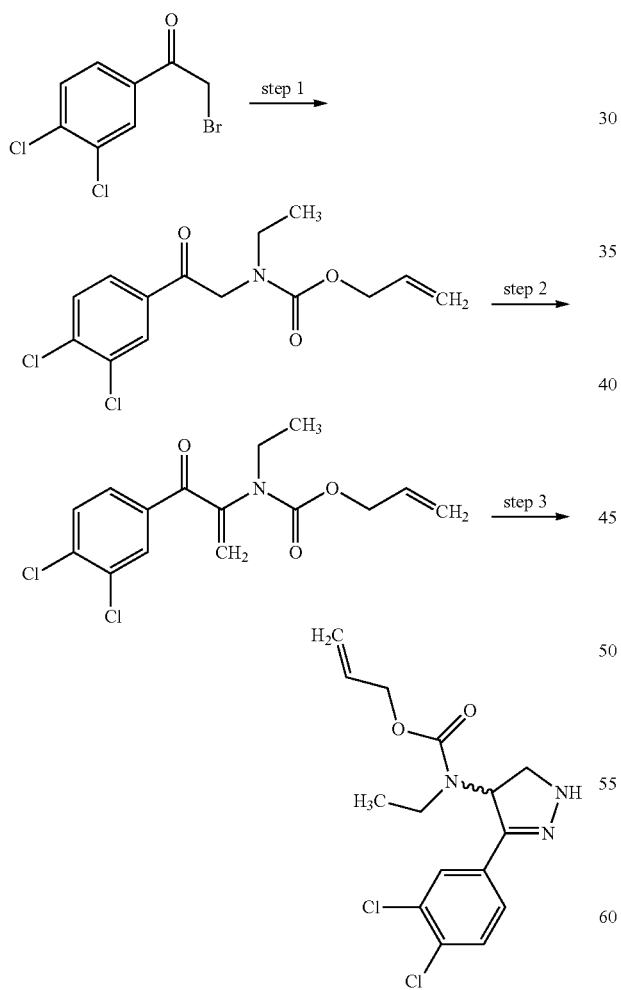

Step 1

To 2-bromo-1-(4-chloro-3-methylphenyl)ethanone (intermediate 2) (20 g, 74.6 mmol), ethyl amine (2M in tetrahydrofuran) (187 ml) was added. The mixture was cooled to −50° C., and allyl chloroformate (18 g) was added. The reaction was stirred at room temperature for 16 h.

Step 2 and 3 were performed as described for intermediate 7, to obtain the N-ethylated analogue Rac-allyl [3-(3,4-dichlorophenyl)-4,5-dihydro-1H-pyrazol-4-yl]ethylcarbamate.

MS (ESI): [M+H]⁺=342.1

Intermediate 33

Rac-phenyl 4-{[(allyloxy)carbonyl](ethyl)amino}-N-cyano-3-(3,4-dichlorophenyl)-4,5-dihydro-1H-pyrazole-1-carboximidate

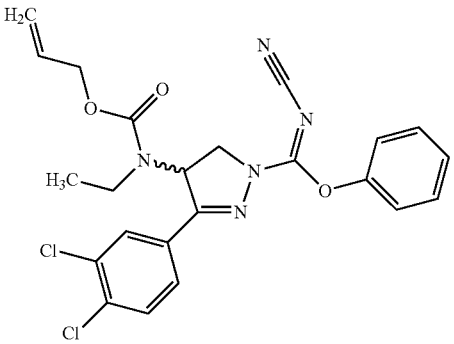 [SMILES: C=CCOC(=O)N(CC)C1CN(/C(=N\C#N)Oc2ccccc2)N=C1c1ccc(Cl)c(Cl)c1]

Intermediate 33 was prepared from intermediate 32 in analogy to the preparation of intermediate 9 from intermediate 7. Rac-phenyl 4-{[(allyloxy)carbonyl](ethyl)amino}-N-cyano-3-(3,4-dichlorophenyl)-4,5-dihydro-1H-pyrazole-1-carboximidate was obtained as an off-white solid.

¹H NMR (400 MHz, DMSO-d6): δ [ppm]=1.02 (m, 3H), 3.21 (m, 1H), 3.48 (m, 1H), 4.24 (d, 1H), 4.50-4.64 (m, 3H), 5.12-5.32 (m, 2H), 5.78-5.95 (m, 2H), 7.24-7.37 (m, 3H), 7.48 (t, 2H), 7.71 (m, 1H), 7.84 (d, 1H), 7.93 (m, 1H).

LCMS (method 4): R$_t$ 3.32 min

MS (ESI): [M+H]⁺=486.1

Intermediate 34

Rac-allyl [3-(3,4-dichlorophenyl)-4,5-dihydro-1H-pyrazol-4-yl]methylcarbamate

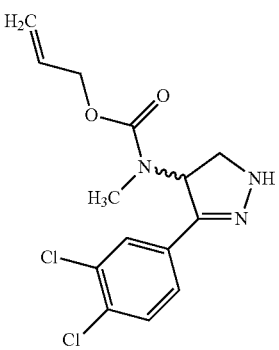 [SMILES: C=CCOC(=O)N(C)C1CNN=C1c1ccc(Cl)c(Cl)c1]

Intermediate 32 was synthesized starting from intermediate 2 following the scheme below.

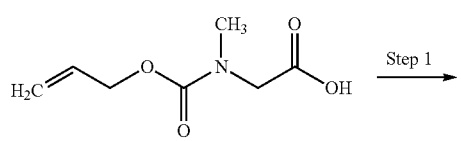

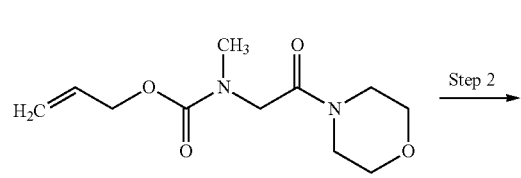

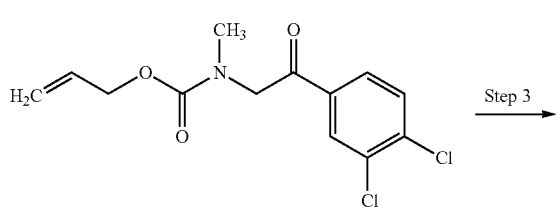

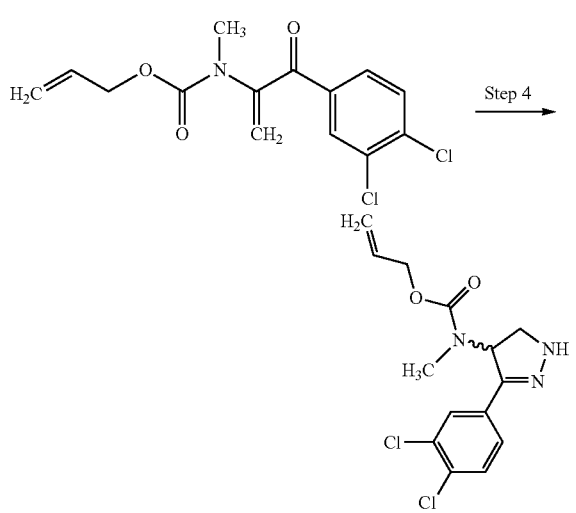

Step 1 and 2 were performed as similarly described in *Org. Process Res. Dev.* 2012, 16, 982-1002 (page 989, scheme 10), starting with Alloc-protected instead of Boc-protected sarcosine and using 4-bromo-1,2-dichlorobenzene instead of 4-bromo-1-fluoro-2-(trifluoromethyl)benzene for the preparation of the grignard reagent.

Step 3 and 4 were performed as described for intermediate 7, to obtain the N-methylated analogue Rac-allyl [3-(3,4-dichlorophenyl)-4,5-dihydro-1H-pyrazol-4-yl]methylcarbamate.

MS (ESI): [M+H]⁺=328.1

Intermediate 35

Rac-phenyl 4-{[(allyloxy)carbonyl](methyl)amino}-N-cyano-3-(3,4-dichlorophenyl)-4,5-dihydro-1H-pyrazole-1-carboximidate

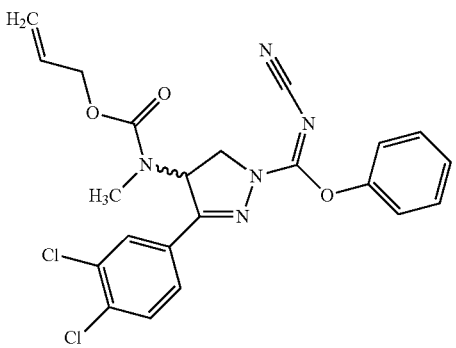 [SMILES: C=CCOC(=O)N(C)C1CN(/C(=N\C#N)Oc2ccccc2)N=C1c1ccc(Cl)c(Cl)c1]

Intermediate 35 was prepared from intermediate 34 in analogy to the preparation of intermediate 9 from intermediate 7. Rac-phenyl 4-{[(allyloxy)carbonyl](methyl)amino}-N-cyano-3-(3,4-dichlorophenyl)-4,5-dihydro-1H-pyrazole-1-carboximidate was obtained as an off-white solid.

$^1$H NMR (400 MHz, DMSO-d6): δ [ppm]=2.75 (s, 3H), 4.35 (dd, 1H), 4.48 (t, 1H), 4.55-4.70 (m, 2H), 5.14-5.40 (m, 2H), 5.93 (m, 1H), 6.17 (m, 1H), 7.27-7.37 (m, 3H), 7.48 (t, 2H), 7.70 (m, 1H), 7.84 (d, 1H), 7.90 (m, 1H).

LCMS (method 4): $R_t$ 3.19 min

MS (ESI): [M+H]⁺=472.1

Intermediate 36

Rac-allyl [1-{N'-cyano-N-[3-(difluoromethoxy)-2-fluorophenyl]carbamimidoyl}-3-(3,4-dichlorophenyl)-4,5-dihydro-1H-pyrazol-4-yl]ethylcarbamate

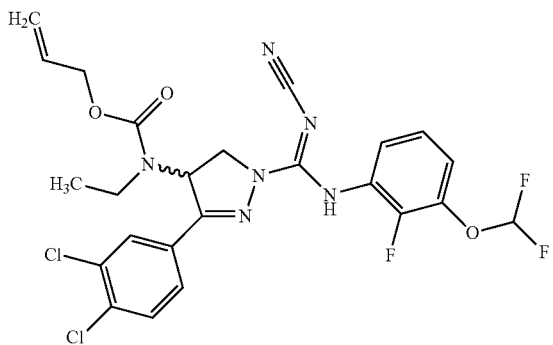 [SMILES: C=CCOC(=O)N(CC)C1CN(/C(=N\C#N)Nc2cccc(OC(F)F)c2F)N=C1c1ccc(Cl)c(Cl)c1]

Intermediate 36 was prepared from intermediate 33, following the procedure described for the synthesis of intermediate 12. In this case, 3-(difluoromethoxy)-2-fluoroaniline was used as the aniline instead of 3-(difluoromethoxy)aniline. The crude product was directly used without purification.

LCMS (method 2): $R_t$ 1.19 min

MS (ESI): [M+H]⁺=568.7

Intermediate 37

Rac-allyl [1-{N'-cyano-N-[2-methoxy-5-(trifluoromethoxy)phenyl]carbamimidoyl}-3-(3,4-dichlorophenyl)-4,5-dihydro-1H-pyrazol-4-yl]ethylcarbamate

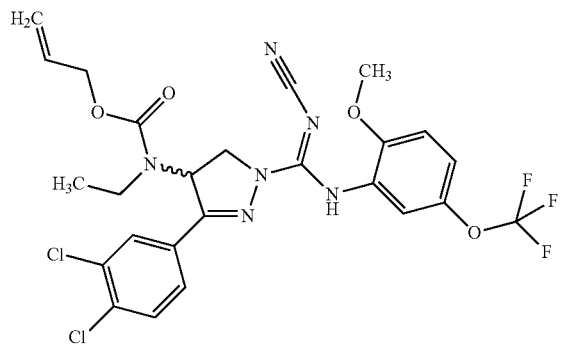 [SMILES: C=CCOC(=O)N(CC)C1CN(/C(=N\C#N)Nc2cc(OC(F)(F)F)ccc2OC)N=C1c1ccc(Cl)c(Cl)c1]

Intermediate 37 was prepared from intermediate 33, following the procedure described for the synthesis of intermediate 12. In this case, 2-methoxy-5-(trifluoromethoxy)aniline was used as the aniline instead of 3-(difluoromethoxy)aniline. The crude product was treated with diethyl ether. The suspension was stirred for 10 min, and then the solid was filtered and dried to give the desired product.

LCMS (method 2): $R_t$ 1.53 min
MS (ESI): $[M+H]^+=599.3$

Intermediate 38

Rac-allyl [1-(N'-cyano-N-{5-(difluoromethoxy)-2-[3-(dimethylamino)propoxy]phenyl}carbamimidoyl)-3-(3,4-dichlorophenyl)-4,5-dihydro-1H-pyrazol-4-yl]ethylcarbamate

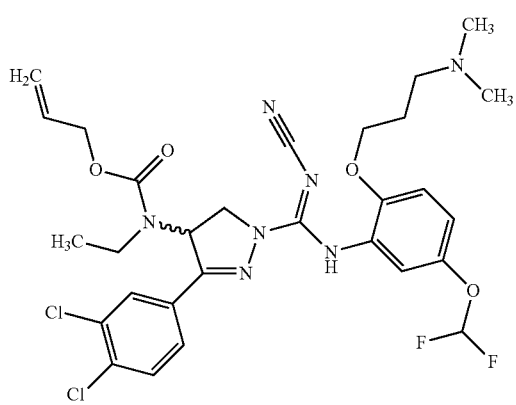 [SMILES: C=CCOC(=O)N(CC)C1CN(/C(=N\C#N)Nc2cc(OC(F)F)ccc2OCCCN(C)C)N=C1c1ccc(Cl)c(Cl)c1]

Intermediate 38 was prepared from intermediate 33, following the procedure described for the synthesis of intermediate 12. In this case, 5-(difluoromethoxy)-2-[3-(dimethylamino)propoxy]aniline was used as the aniline instead of 3-(difluoromethoxy)aniline. The crude product was directly used without purification.

Analytical data of subsequent alloc-deprotected rac-N'-cyano-3-(3,4-dichlorophenyl)-N-{5-(difluoromethoxy)-2-[3-(dimethylamino)propoxy]phenyl}-4-(ethylamino)-4,5-dihydro-1H-pyrazole-1-carboximidamide:

LCMS (method 2): $R_t$ 1.50 min
MS (ESI): $[M+H]^+=569.9$

Intermediate 39

Rac-allyl [1-(N'-cyano-N-{2-[(1-methylpiperidin-4-yl)oxy]-5-(trifluoromethyl)phenyl}carbamimidoyl)-3-(3,4-dichlorophenyl)-4,5-dihydro-1H-pyrazol-4-yl]ethylcarbamate

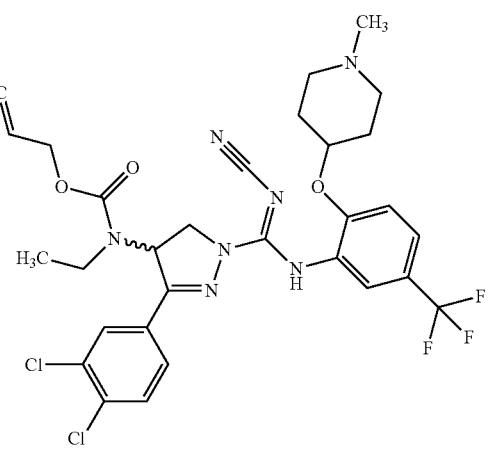

Intermediate 39 was prepared from intermediate 33, following the procedure described for the synthesis of intermediate 12. In this case, 2-[(1-methylpiperidin-4-yl)oxy]-5-(trifluoromethyl)aniline was used as the aniline instead of 3-(difluoromethoxy)aniline. The crude product was directly used LCMS (method 2): $R_t$ 1.50 min
MS (ESI): $[M+H]^+=666.4$

Intermediate 40

Rac-allyl [1-{N'-cyano-N-[3-(difluoromethoxy)phenyl]carbamimidoyl}-3-(3,4-dichlorophenyl)-4,5-dihydro-1H-pyrazol-4-yl]methylcarbamate

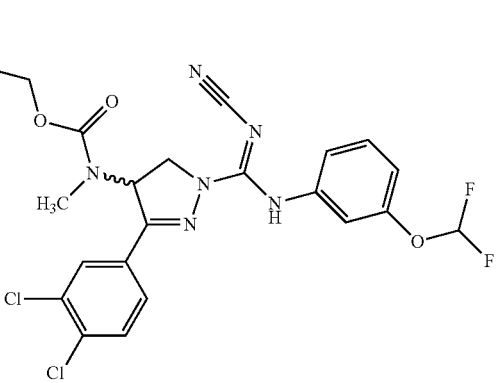

Intermediate 40 was prepared from intermediate 34, following the procedure described for the synthesis of intermediate 12.
LCMS (method 1): R$_t$ 1.36 min
MS (ESI): [M+H]$^+$=536.8

Intermediate 41

4-methoxy-3-nitrophenyl acetate

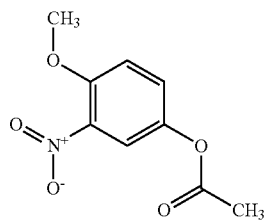

Acetic anhydride 100 mL was added to a solution of 4-methoxyphenol (CAS: 150-76-5) 24.8 g (0.2 mol) in acetic acid 100 mL at room temperature. The pale yellow solution was stirred at 100° C. for 3.5 hours. The solution was cooled to 0° C. and 70% nitric acid 20 mL was added slowly over 10 minutes, solution became warm. The orange solution was stirred at 0° C. for 1 hour, a solid precipitated. Water 100 mL was added and the solid collected by filtration and washed with further water to give 4-methoxy-3-nitrophenyl acetate as a cream solid, 47.25 g (112%, still water present). Taken onto next step without further drying.
$^1$H NMR (400 MHz, CDCl$_3$): δ [ppm]=2.30 (s, 3H), 3.95 (s, 3H), 7.08 (d, 1H), 7.30 (dd, 1H), 7.65 (d, 1H)
UPLC (method 6): R$_t$ 0.69 min Intermediate 42

4-methoxy-3-nitrophenol

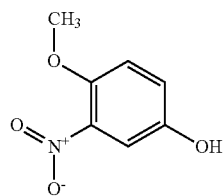

4-Methoxy-3-nitrophenyl acetate 47.25 g (200 mmol) was suspended in ethanol 800 mL and cooled to 0° C. A 1 M aqueous solution of sodium hydroxide 220 mL was added slowly and the light yellow suspension became a dark red solution. Stirred for 1 hour and allowed to warm to room temperature. The reaction was quenched with acetic acid to give a light orange solution. Partitioned between brine and ethyl acetate, the aqueous was washed with further ethyl acetate. The combined organic extracts were washed with further brine, dried over sodium sulfate and concentrated to a dark orange oil which crystallised on standing to give 4-methoxy-3-nitrophenol, 30.97 g (92%).
$^1$H NMR (400 MHz, CDCl$_3$): δ [ppm]=3.90 (s, 3H), 5.54 (br s, 1H), 6.98 (d, 1H), 7.07 (dd, 1H), 7.38 (d, 1H)
UPLC (method 6): R$_t$ 0.47 min
MS (ESI): [M−H]$^-$=167.95

Intermediate 43

4-(difluoromethoxy)-1-methoxy-2-nitrobenzene

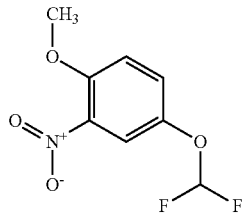

A solution of 4-methoxy-3-nitrophenol 10.0 g (59.1 mmol) in N,N-dimethylformamide 150 mL was degassed with argon for 20 minutes. Cesium carbonate 38.5 g (118.2 mmol) was added and the orange solution became a dark red suspension. Sodium chlorodifluoroacetate 18.0 g (118.2 mmol) was added and the suspension was stirred at 100° C. for 1.5 hours, a light brown suspension formed. Diluted with water and extracted with ethyl acetate twice. The combined organic extracts were washed with brine three times, dried over sodium sulfate and concentrated to a light brown solid. The solid was triturated with methanol and the cream solid collected by filtration. The filtrate was concentrated to a dark brown oil (6.60 g). Purification by dry-flash column chromatography on silica gel 60 (heptanes:ethyl acetate 4:1 to 1:1) to give a yellow oil which solidified on standing to give 4-(difluoromethoxy)-1-methoxy-2-nitrobenzene, 4.65 g (36%).
$^1$H NMR (400 MHz, CDCl$_3$): δ [ppm]=3.96 (s, 3H), 6.48 (t, 1H), 7.08 (d, 1H), 7.36 (dd, 1H), 7.67 (d, 1H)
UPLC (method 6): R$_t$ 0.74 min Intermediate 44

5-(difluoromethoxy)-2-methoxyaniline

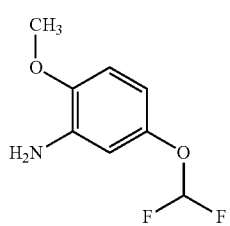

A suspension of 4-(difluoromethoxy)-1-methoxy-2-nitrobenzene 6.43 g (29.3 mmol) and tin(II) chloride dihydrate, 33.1 g (146.7 mmol) in ethyl acetate 100 mL was heated to reflux for 2.5 hours. The reaction mixture was poured into a potassium carbonate aqueous solution 200 mL. The resulting suspension was filtered through a pad of celite and washed with ethyl acetate. The biphasic filtrate was separated and the aqueous was washed with ethyl acetate. The combined organic extracts were washed with brine, dried over sodium sulfate and concentrated to give 5-(difluoromethoxy)-2-methoxyaniline as a purple oil 5.17 g (93%).
$^1$H NMR (400 MHz, CDCl$_3$): δ [ppm]=3.83 (s, 3H), 3.88 (br s, 2H), 6.38 (t, 1H), 6.46 (dd, 1H), 6.50 (d, 1H), 6.69 (d, 1H)
UPLC (method 6): R$_t$ 0.68 min
MS (ESI): [M+H]$^+$=190.05

Examples for the Production of the Inventive Compounds

Example 1

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxypropanamide (1:1 Mixture of Diastereomers)

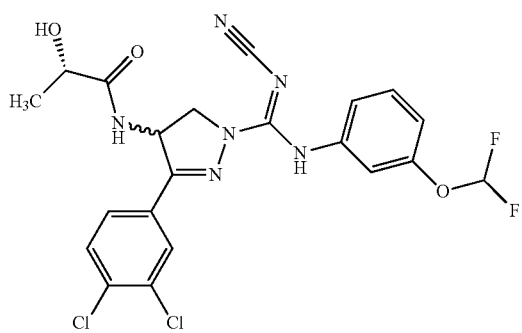 [SMILES: C[C@H](O)C(=O)NC1CN(/C(=N\C#N)Nc2cccc(OC(F)F)c2)N=C1c1ccc(Cl)c(Cl)c1]

Example 1 was prepared starting from intermediate 12 according to the following scheme:

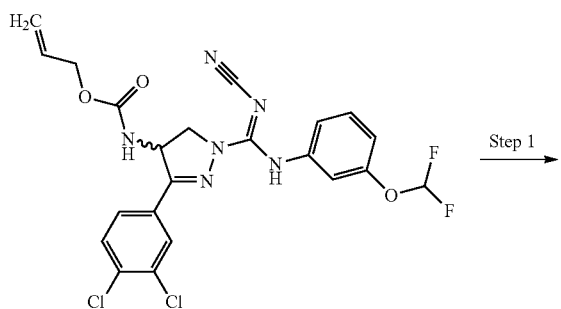

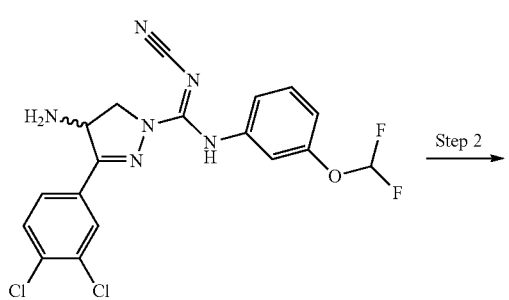

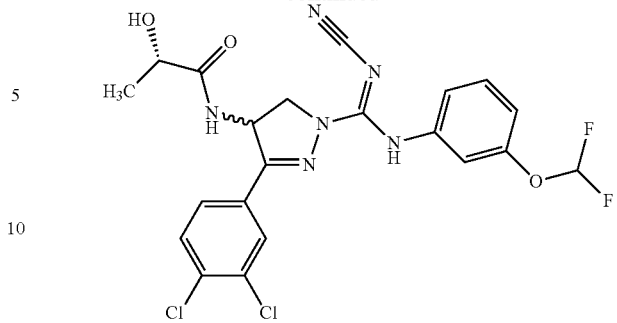

Step 1

To a stirred solution of rac-allyl [1-{N'-cyano-N-[3-(difluoromethoxy)phenyl]carbamimidoyl}-3-(3,4-dichlorophenyl)-4,5-dihydro-1H-pyrazol-4-yl]carbamate (intermediate 12), 14.2 g (27.0 mmol) in degassed tetrahydrofuran (370 mL) was added 1,3-dimethylbarbituric acid, 17.0 g (108 mmol) followed by tetrakis(triphenylphosphine) palladium 0, 2.40 g (2.16 mmol). The reaction mixture was stirred under argon for 15 minutes then cautiously quenched with saturated sodium hydrogen carbonate solution (400 mL) and extracted into ethyl acetate (400 mL). The organic layer was washed with brine solution (200 mL) before being dried over magnesium sulfate, filtered and the solvent evaporated to yield a crude orange oil. The crude material was purified by dry flash column chromatography (eluent: ethyl acetate-heptane 1:1, 2:1; ethyl acetate; methanol-ethyl acetate 0.01:1) to yield 4-amino-N'-cyano-3-(3,4-dichlorophenyl)-N-[3-(difluoromethoxy)phenyl]-4,5-dihydro-1H-pyrazole-1-carboximidamide, 9.3 g (78%) as an orange oil.

$^1$H NMR (400 MHz, DMSO-d6): δ [ppm]=3.95-4.02 (m, 1H under ethyl acetate signal), 4.35 (dd, 1H), 4.80 (dd, 1H), 6.98 (dd, 1H), 7.19 (t, 1H), 7.21 (t, 1H), 7.23 (dd, 1H), 7.38 (t, 1H), 7.48-7.61 (m, 1H), 7.72 (d, 1H), 8.00 (dd, 1H), 8.31 (d, 1H), 9.67 (br s, 1H);

LCMS (method 3): $R_t$ 1.65 min

MS (ESI): [M+H]$^+$=439.1

Step 2

To the solution of L-lactic acid (61.5 mg, 683 μmol) in N,N-dimethylformamide (2 ml) was added 1-[Bis(dimethylamino)methylene]-1H-1,2,3-triazolo[4,5-b]pyridinium 3-oxid hexafluorophosphate (HATU, CAS No. 148893-10-1), 260 mg (683 μmol), followed by N-methylmorpholine (150 yl, 1.37 mmol), and the mixture was stirred for 30 min. rac-4-amino-N'-cyano-3-(3,4-dichlorophenyl)-N-[3-(difluoromethoxy)phenyl]-4,5-dihydro-1H-pyrazole-1-carboximidamide (150 mg, 341 μmol) dissolved in N,N-dimethylformamide (1 ml) was added and stirred for 12 h at room temperature. The reaction mixture was treated with potassium carbonate (25 mg) and methanol (2 ml) for 1 h. The solids were filtered off and the filtrate was concentrated in vacuo. The residue was purified by preparative HPLC (gradient of acetonitrile in water) to yield 5 mg (3%) of the desired product.

LCMS (method 5): $R_t$ 1.18 min

MS (ESI): [M+H]$^+$=510.9

Example 2

Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-N-methylacetamide

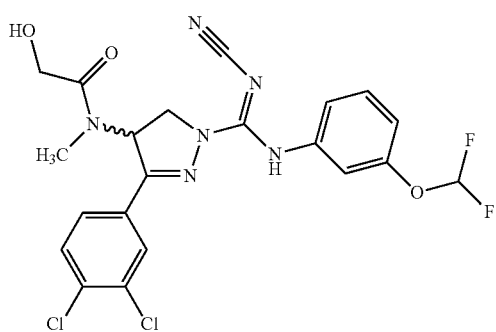 [SMILES: CN(C(=O)CO)C1CN(/C(=N\C#N)Nc2cccc(OC(F)F)c2)N=C1c1ccc(Cl)c(Cl)c1]

Example 2 was prepared starting from intermediate 40 according to the following scheme:

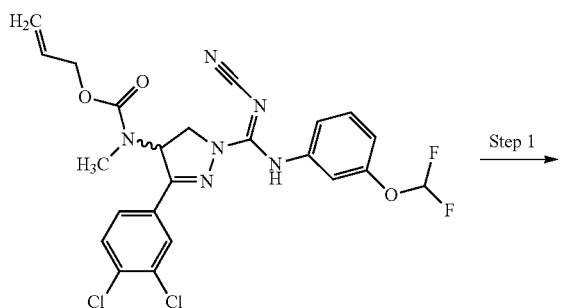

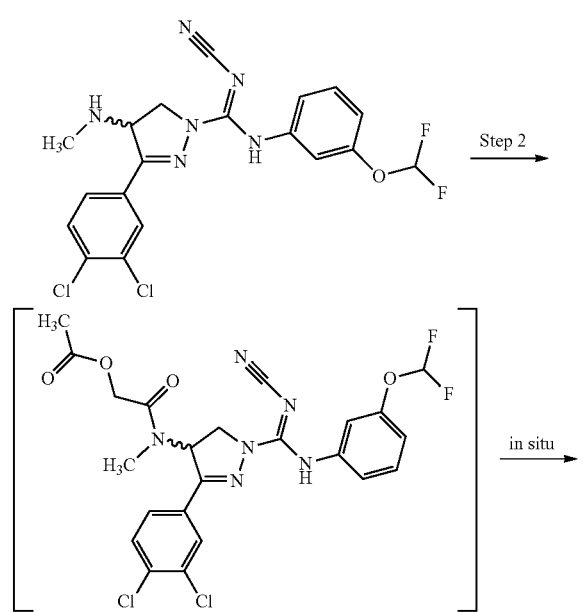

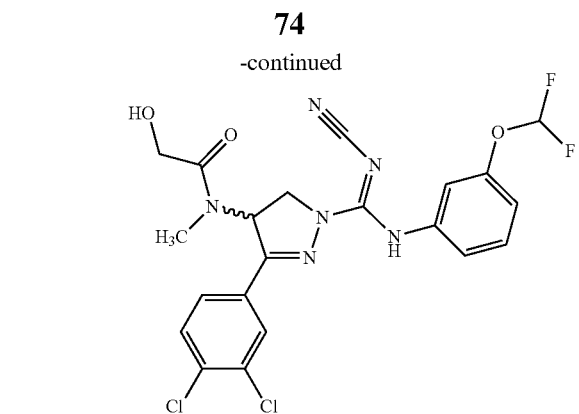

Step 1

To a stirred solution of rac-allyl [1-{N'-cyano-N-[3-(difluoromethoxy)phenyl]carbamimidoyl}-3-(3,4-dichlorophenyl)-4,5-dihydro-1H-pyrazol-4-yl]methylcarbamate (intermediate 40), 875 mg (1.6 mmol) in tetrahydrofuran (12 mL) was added 1,3-dimethylbarbituric acid, 508 mg (3.3 mmol) followed by tetrakis(triphenylphosphine) palladium 56.5 mg (0.05 mmol). The reaction mixture was stirred under argon for 1 hour then cautiously quenched with saturated sodium hydrogen carbonate solution (400 mL) and extracted into ethyl acetate (400 mL). The organic layer was washed with brine solution (200 mL) before being dried over magnesium sulfate, filtered and the solvent evaporated. The crude material was stirred in diethyl ether (10 ml), filtered, and dried to yield crude rac-N'-cyano-3-(3,4-dichlorophenyl)-N-[3-(difluoromethoxy)phenyl]-4-(methylamino)-4,5-dihydro-1H-pyrazole-1-carboximidamide (902 mg), which was used in the next step without further purification.

LCMS (method 5): $R_t$ 1.29 min

MS (ESI): $[M+H]^+=452.8$

Step 2

To rac-N'-cyano-3-(3,4-dichlorophenyl)-N-[3-(difluoromethoxy)phenyl]-4-(methylamino)-4,5-dihydro-1H-pyrazole-1-carboximidamide 246 mg (0.54 mmol) in dichloromethane (12 mL) was added saturated sodium hydrogen carbonate solution (12 mL). The biphasic mixture was stirred vigorously and cooled to 0° C., acetoxyacetyl chloride (111 mg, 0.81 mmol) in dichloromethane, 3 mL was added dropwise over 15 min. The reaction mixture was stirred for 30 minutes at 0° C. Dichloromethane was removed by evaporation to yield an oily aqueous suspension, to which potassium carbonate, 150 mg (1.1 mmol) was added followed by methanol (4 mL). The reaction mixture was brought to reflux for 30 min then allowed to cool to room temperature. Upon cooling rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-N-methylacetamide precipitated out of solution as a white solid which was filtered, and purified by column chromatography (reversed phase, water, acetonitrile), to yield 37 mg (13%) of the desired product.

$^1$H-NMR (400 MHz, DMSO-$d_6$): d [ppm]=2.69 (s, 3H), 4.09 (d, 2H), 4.20 (dd, 1H), 4.39 (t, 1H), 4.77 (t, 1H), 6.37 (br. s., 1H), 6.98 (d, 1H), 7.19 (s, 1.25H), 7.20-7.26 (m, 1.5H), 7.39-7.44 (m, 1.25H), 7.63 (dd, 1H), 7.76 (d, 1H), 8.05-8.15 (m, 1H), 9.25 (br. s., 1H).

MS (ESI): $[M+H]^+=511$

Example 3

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylglycinamide

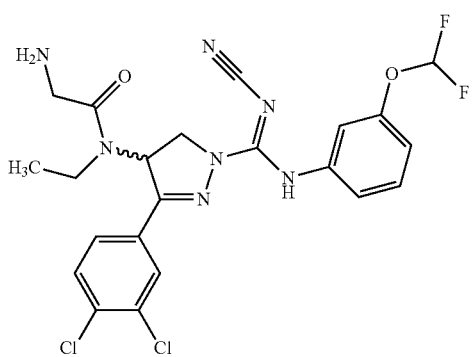 [SMILES: CCN(C(=O)CN)C1CN(/C(=N\C#N)Nc2cccc(OC(F)F)c2)N=C1c1ccc(Cl)c(Cl)c1]

Example 3 was prepared starting from intermediate 12 according to the following scheme:

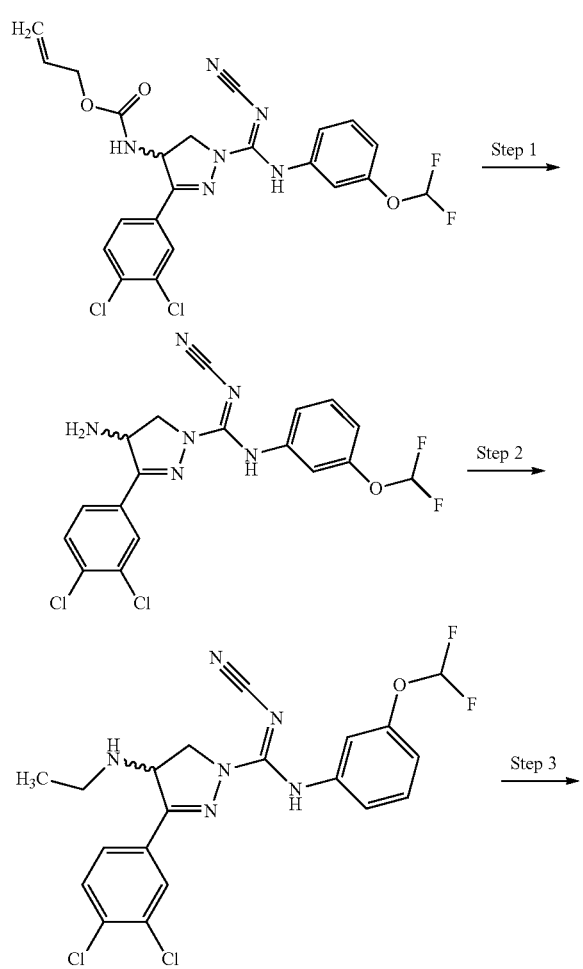

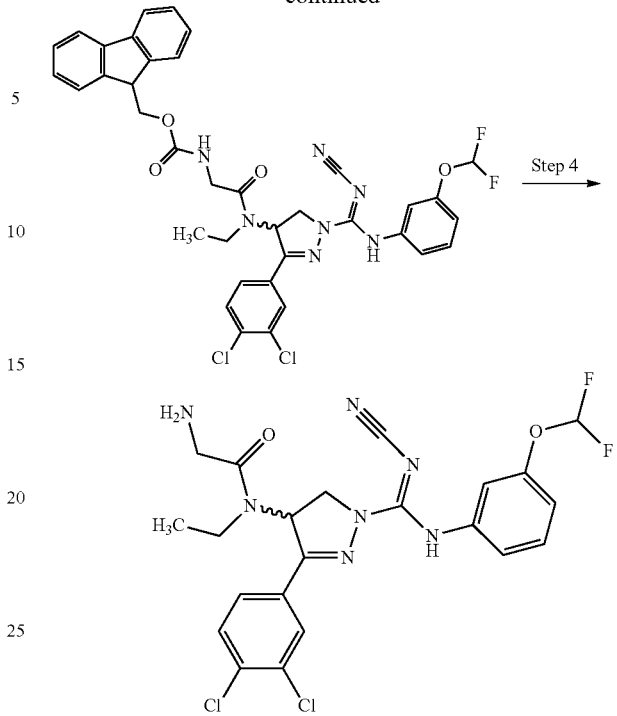

Step 1
As described for example 1.

Step 2
To a stirred solution of rac-4-amino-N'-cyano-3-(3,4-dichlorophenyl)-N-[3-(difluoromethoxy)phenyl]-4,5-dihydro-1H-pyrazole-1-carboximidamide, 9.30 g (21.2 mmol) in methanol (170 mL) at 0° C. was added acetaldehyde, 1.12 g (25.4 mmol) followed by the portion wise addition of sodium borohydride, 0.96 g (25.4 mmol) over 20 minutes. The reaction mixture was stirred for 30 minutes before pouring over saturated sodium hydrogen carbonate solution (100 mL). The methanol was removed by evaporation and the resulting aqueous slurry was extracted with ethyl acetate (2×100 mL). The organic layers were combined and washed with brine solution (100 mL) dried over magnesium sulfate, filtered and the solvent evaporated to yield a crude black oil. The crude material was purified by dry flash column chromatography (eluent: ethyl acetate-heptane 1:1, 2:1; ethyl acetate) to yield a black oil, which was triturated with diethyl ether to yield rac-N'-cyano-3-(3,4-dichlorophenyl)-N-[3-(difluoromethoxy)phenyl]-4-(ethylamino)-4,5-dihydro-H-pyrazole-1-carboximidamide, 7.40 g (75%) as a grey solid.

$^1$H NMR (400 MHz, DMSO-d6): δ [ppm]=0.98 (t, 3H), 2.40-2.64 (m, 2H partially under DMSO signal), 4.16-4.27 (m, 2H), 4.83 (dd, 1H), 6.98 (dd, 1H), 7.20 (d, 1H), 7.21 (t, 1H), 7.25 (dd, 1H), 7.39 (t, 1H), 7.70 (d, 1H), 7.97 (dd, 1H), 8.29 (d, 1H), 9.71 (br s, 1H)

LCMS (method 3): $R_t$ 1.80 min
MS (ESI): [M+H]$^+$=467.18

Step 3
To a solution of rac-N'-cyano-3-(3,4-dichlorophenyl)-N-[3-(difluoromethoxy)phenyl]-4-(ethylamino)-4,5-dihydro-1H-pyrazole-1-carboximidamide (300 mg, 0.64 mmol) in DMF (15 mL) was added Fmoc-glycine (382 mg, 1.3 mmol), HATU (488 mg, 1.3 mmol), and 4-methylmorpholine (0.28 mL, 2.6 mmol). The solution was stirred at room temperature for 4 h. The reaction mixture was poured into water (25 mL), and the mixture was extracted with ethyl acetate (3×50 mL). The organic phases were dried over magnesium sulphate and concentrated in vacuo. The residue was directly used in the following reaction.

Step 4

The crude product from step 3 was dissolved in dichloromethane (20 mL) and piperidine (0.8 mL) was added. The reaction was stirred at room temperature for 1.5 h. Water (10 mL) was added, and the aqueous was extracted with ethyl acetate (3×20 mL). The combined organic phases were washed with brine, dried over magnesium sulphate and concentrated. The crude product was purified by chromatography (RP, water+0.1% ammonia, acetonitrile) to give rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylglycinamide (150 mg, 45%).

$^1$H-NMR (400 MHz, DMSO-d$_6$): d [ppm]=1.07-1.22 (m, 3H), 3.77-3.98 (m, 2H), 4.15 (dd, 1H), 4.55 (t, 1H), 7.02-7.07 (m, 1.25H), 7.21 (t, 1H), 7.23-7.29 (m, 1.5H), 7.41-7.47 (m, 1.25H), 7.68 (dd, 1H), 7.75 (m, 1H), 7.90-8.03 (m, 3H), 8.16 (d, 1H), 9.86 (s, 1H); 3H obscured by solvent and water signals.

LCMS (method 2): R$_t$ 1.12 min
MS (ESI): [M+H]$^+$=523.8

Example 4

Rac-N-[1-{N'-cyano-N-[3-(difluoromethoxy)phenyl] carbamimidoyl}-3-(3,4-dichlorophenyl)-4,5-dihydro-1H-pyrazol-4-yl]-N-ethyl-2-hydroxyacetamide

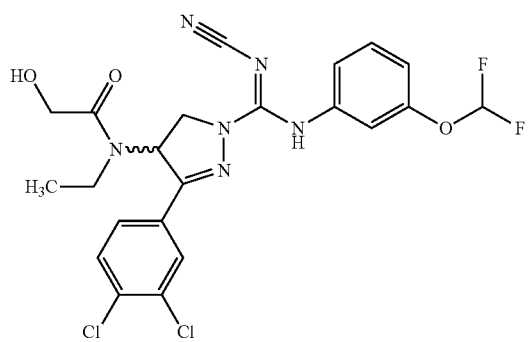 [SMILES: CCN(C(=O)CO)C1CN(/C(=N\C#N)Nc2cccc(OC(F)F)c2)N=C1c1ccc(Cl)c(Cl)c1]

Example 4 was prepared starting from intermediate 12 according to the following scheme:

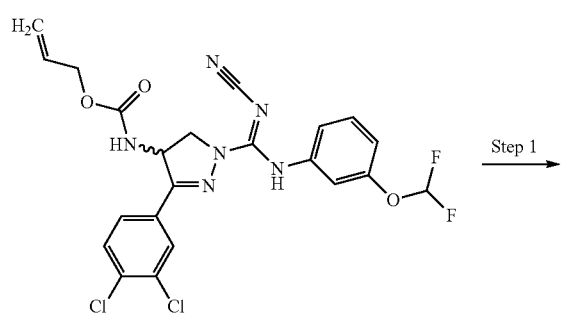

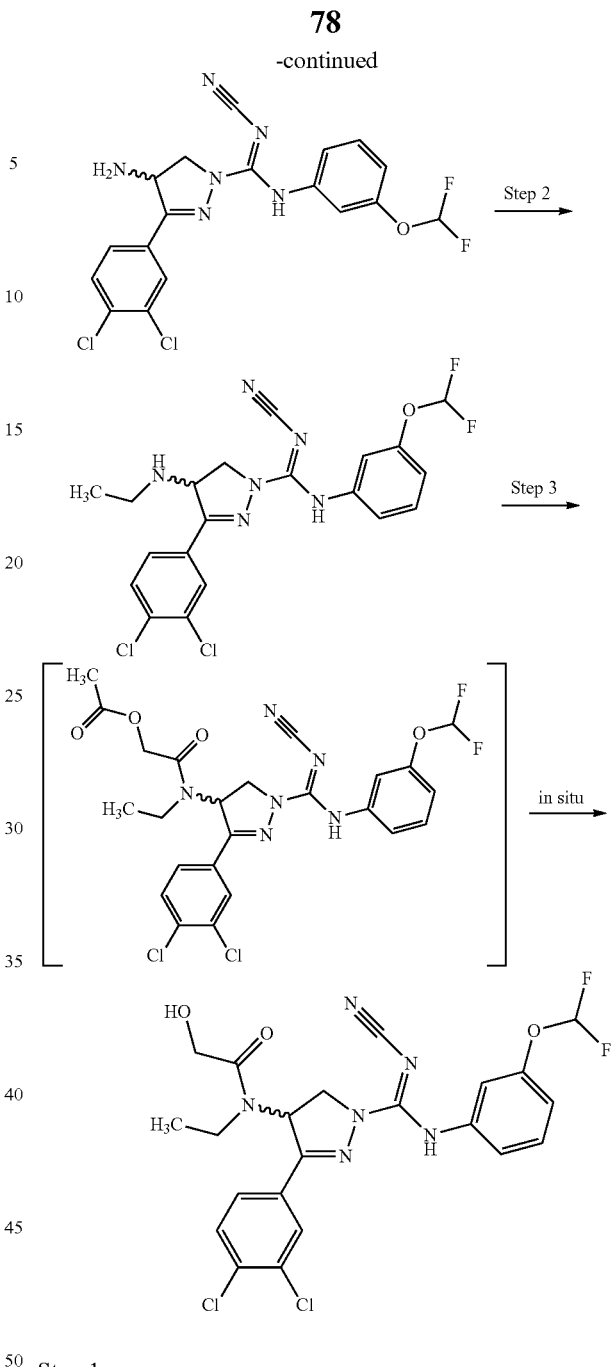

Step 1
As described for example 1.
Step 2
As described for example 3.
Step 3
To rac-N'-cyano-3-(3,4-dichlorophenyl)-N-[3-(difluoromethoxy)phenyl]-4-(ethylamino)-4,5-dihydro-1H-pyrazole-1-carboximidamide, 7.24 g (15.5 mmol) in dichloromethane, 62 mL was added saturated sodium hydrogen carbonate solution, 72 mL. The biphasic mixture was stirred vigorously and cooled to 5° C., acetoxyacetyl chloride, 2.50 mL (23.2 mmol) in dichloromethane, 10 mL was added dropwise over 15 min. The reaction mixture was stirred for 10 mins at 5° C. after which time LC analysis indicated total consumption of starting material with only one major peak. Dichloromethane was removed by evaporation to yield an oily aqueous suspension to which potassium carbonate, 4.28 g (31.0 mmol) was added followed by methanol, 110 mL. The reaction mixture was brought to reflux for 5 min then allowed to cool to room temperature. Upon cooling rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide precipitated out of solution as a white solid which was filtered, washing with water, 50 mL and diethyl ether, 50 mL. The precipitate was dried in vacuo to yield the desired product, 7.58 g (93%) as a white powder.

$^1$H NMR (400 MHz, DMSO-d6): δ [ppm]=0.98-1.10 (m, 3H), 3.42-3.17 (m, 2H partially under water signal), 3.94-4.17 (m, 3H), 4.46 (dd, 1H), 4.75 (dd, 1H), 6.98 (dd, 1H), 7.18 (t, 1H), 7.22 (dd, 1H), 7.23 (t, 1H), 7.40 (t, 1H), 7.62 (dd, 1H), 7.72 (d, 1H), 8.11 (d, 1H), 9.85 (br s, 1H)

UPLC (method 6): $R_t$ 0.58 min

MS (ESI): $[M+H]^+$=525

Example 4 was separated into its enantiomers by chiral SFC:

| System: | Sepiatec: Prep SFC100, |
| Column: | Chiralpak ID 5 μm 250 × 20 mm |
| Solvent: | CO2/propan-2-ol 7/3 |
| Flow: | 80 mL/min |
| Temperature: | 40° C. |
| Detection: | UV 254 nm |

| Example No | Rt in min |
| --- | --- |
| 4.1 | 3.35-4.40 |
| 4.2 | 7.31-9.00 |

Example 4.1

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 1

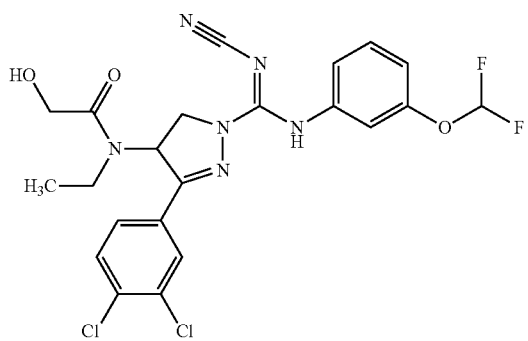 [SMILES: CCN(C(=O)CO)C1CN(/C(=N\C#N)Nc2cccc(OC(F)F)c2)N=C1c1ccc(Cl)c(Cl)c1]

Chiralpak ID 5 m 100×4.6 mm (CO2/2-Propanol 7/3), $R_t$ 2.41 min $[\alpha]_D$=−102° (c: 0.44, MeOH)

Example 4.2

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 2

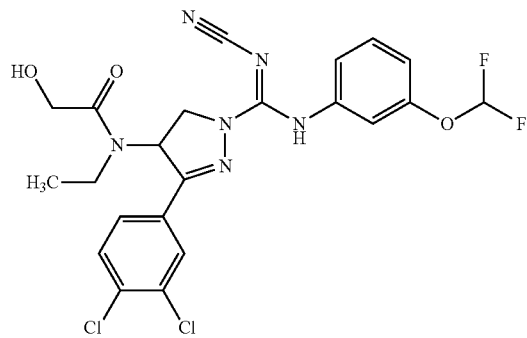 [SMILES: CCN(C(=O)CO)C1CN(/C(=N\C#N)Nc2cccc(OC(F)F)c2)N=C1c1ccc(Cl)c(Cl)c1]

Chiralpak ID 5 m 100×4.6 mm (CO2/2-Propanol 7/3), $R_t$ 5.66 min $[\alpha]_D$=+96° (c: 0.25, MeOH)

Example 5

Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide

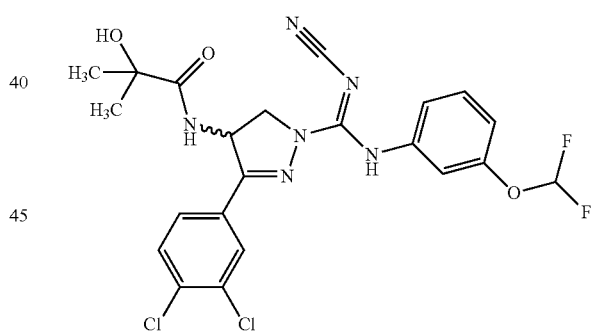

Example 5 was prepared from intermediate 12 according to the following scheme:

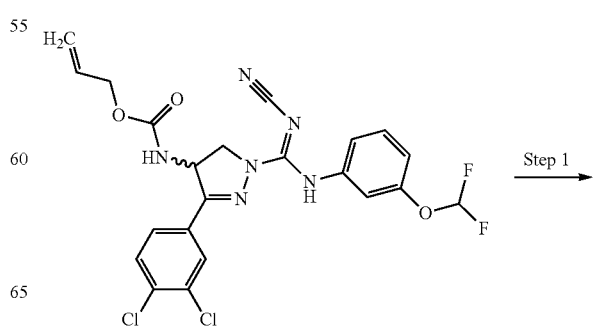

Step 1

-continued

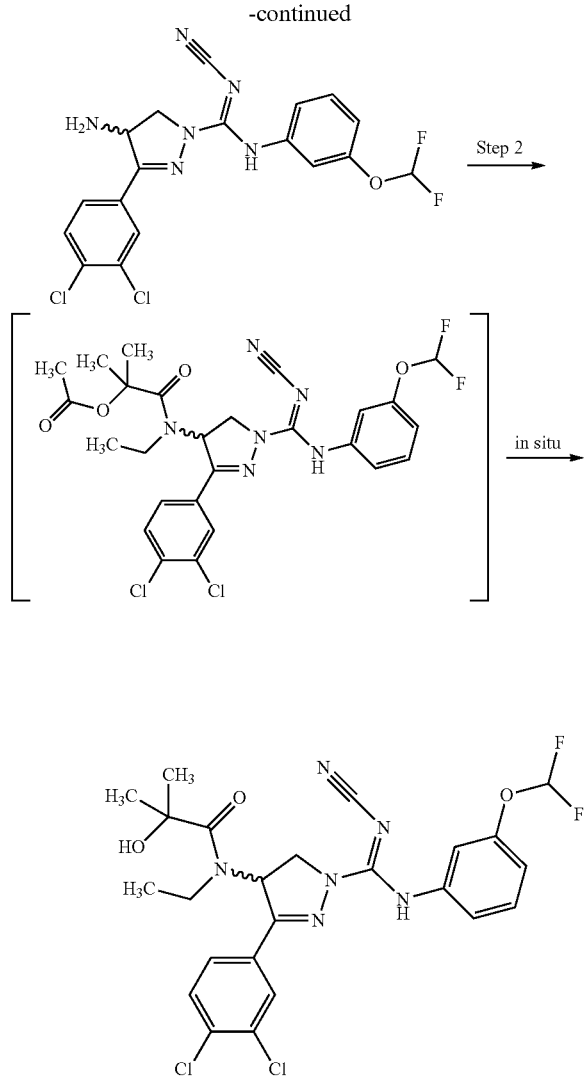

Step 1

As described for example 1.

Step 2

Step 2 was performed in analogy to example 4 (step 3), by reacting rac-4-amino-N'-cyano-3-(3,4-dichlorophenyl)-N-[3-(difluoromethoxy)phenyl]-4,5-dihydro-1H-pyrazole-1-carboximidamide with acetoxy isobutyryl chloride, followed by removal of the acetyl group, to obtain the desired product.

$^1$H NMR (300 MHz, DMSO-$d_6$) δ [ppm]=1.16 (s, 3H), 1.17 (s, 3H), 3.74-3.82 (m, 1H), 4.11-4.22 (m, 1H), 5.64-5.75 (m, 1H), 6.78-6.84 (m, 1H), 6.95 (s, 0.25H), 7.19 (s, 0.5H), 7.29-7.37 (m, 1H), 7.44 (s, 0.25H), 7.51-7.63 (m, 3H), 7.70-7.75 (m, 1H), 7.82 (d, J=2.07 Hz, 1H), 8.11 (d, J=1.88 Hz, 1H), 8.71 (d, J=9.23 Hz, 1H), 9.28 (s, 1H).

LCMS (method 2): R$_t$=1.22 min

MS (ESI): [M+H]$^+$=525.1

Example 5 was separated into its enantiomers by chiral SFC:

| System: | Sepiatec: Prep SFC100, |
|---|---|
| Column: | Chiralpak ID 5 μm 250 × 20 mm |
| Solvent: | CO2/2-Propanol + 0.4% DEA 8/2 |
| Flow: | 80 mL/min |
| Temperature: | 40° C. |
| Detection: | UV 254 nm |

| Example No | Rt in min |
|---|---|
| 5.1 | 2.60-3.00 |
| 5.2 | 3.40-4.40 |

Example 5.1

N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 1

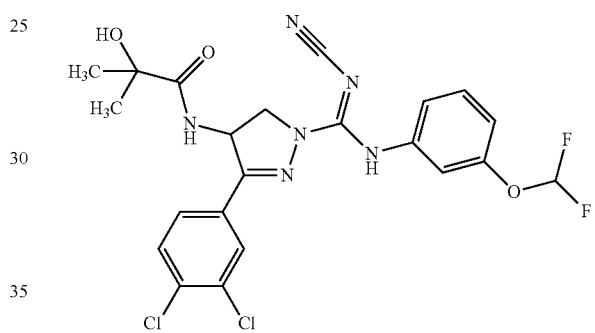

Chiralpak ID 5 μm 100×4.6 mm (CO2/2-Propanol+0.2% Diethylamine 8:2) R$_t$=3.02 min

[α]$_D$=+14.9° (c: 1.0, DMSO)

Example 5.2

N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 2

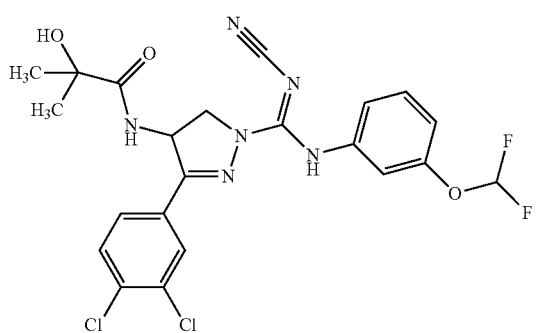 [SMILES: CC(C)(O)C(=O)NC1CN(/C(=N\C#N)Nc2cccc(OC(F)F)c2)N=C1c1ccc(Cl)c(Cl)c1]

Chiralpak ID 5 μm 100×4.6 mm (CO2/2-Propanol+0.2% Diethylamine 8:2) R$_t$=7.09 min

[α]$_D$=−23.2° (c: 1.0, DMSO)

Example 6

Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-beta-alaninamide

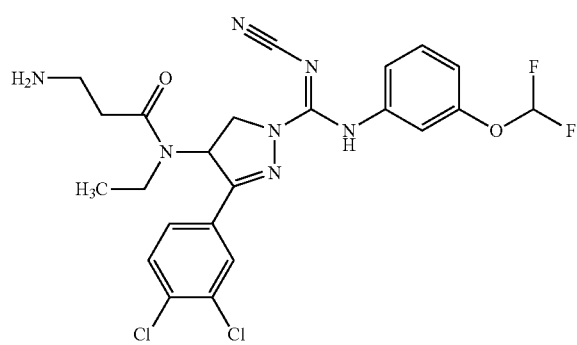 [SMILES: CCN(C(=O)CCN)C1CN(/C(=N\C#N)Nc2cccc(OC(F)F)c2)N=C1c1ccc(Cl)c(Cl)c1]

Example 6 was prepared analogously to example 3 using Fmoc-beta-alanine instead of Fmoc-glycine for the amide coupling.

LCMS (method 2): $R_t$=0.97

MS (ESI): $[M+H]^+$=538.0

Example 7

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide (1:1 Mixture of Diastereomers)

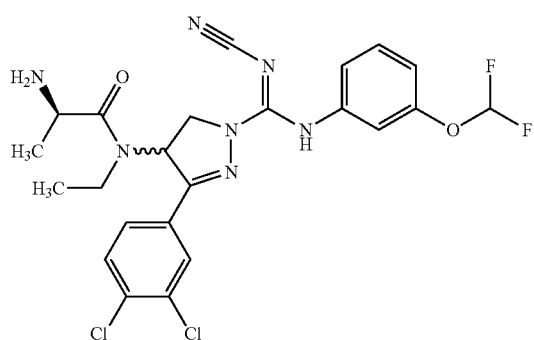 [SMILES: CCN(C(=O)[C@@H](C)N)C1CN(/C(=N\C#N)Nc2cccc(OC(F)F)c2)N=C1c1ccc(Cl)c(Cl)c1]

Example 7 was prepared analogously to example 3 using Fmoc-D-alanine instead of Fmoc-glycine for the amide coupling.

$^1$H-NMR (400 MHz, DMSO-d6): d [ppm]=0.13-0.26 (m, 2H), 0.35-0.55 (m, 6H), 2.65 (d, 1H), 2.85-2.99 (m, 1H), 3.40 (dd, 1H), 3.67-3.80 (m, 1H), 6.03 (t, 1H), 6.19-6.27 (m, 1H), 6.41 (t, 1H), 6.46 (ddd, 1H), 6.60 (t, 1H), 6.79 (d, 1H), 6.85 (dd, 1H), 7.19-7.29 (m, 1H).

MS (ESI): $[M+H]^+$=538

Example 7 was separated into its diastereomers by chiral SFC:

| System: | Sepiatec: Prep SFC100, |
|---|---|
| Column: | Chiralpak IC 5 μm 250 × 20 mm |
| Solvent: | CO2/Ethanol + 0.4% DEA 7/3 |
| Flow: | 80 mL/min |
| Temperature: | 40° C. |
| Detection: | UV 254 nm |

| Example No | Rt in min |
|---|---|
| 7.1 | 2.2-4.0 |
| 7.2 | 7.0-10.2 |

Example 7.1

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 1

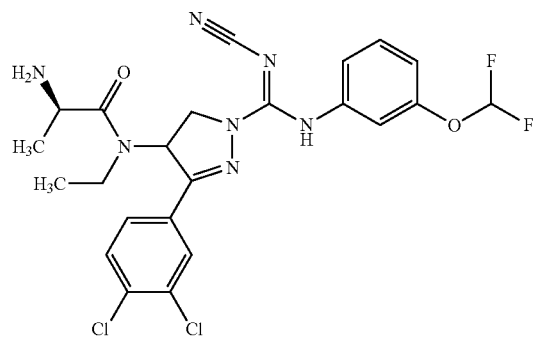 [SMILES: CCN(C(=O)[C@@H](C)N)C1CN(/C(=N\C#N)Nc2cccc(OC(F)F)c2)N=C1c1ccc(Cl)c(Cl)c1]

Chiralpak IC 5 μm 100×4.6 mm (CO2/Ethanol+0.2% DEA 7/3), $R_t$ 1.80 min $[α]_D$=−60° (c: 0.30, DMSO)

Example 7.2

N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 2

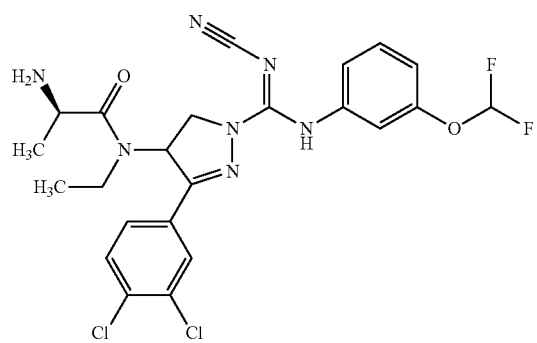 [SMILES: CCN(C(=O)[C@@H](C)N)C1CN(/C(=N\C#N)Nc2cccc(OC(F)F)c2)N=C1c1ccc(Cl)c(Cl)c1]

Chiralpak IC 5 μm 100×4.6 mm (CO2/Ethanol+0.2% DEA 7/3), $R_t$ 4.77 min $[α]_D$=+56° (c: 0.20, DMSO)

Example 8

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 Mixture of Diastereomers)

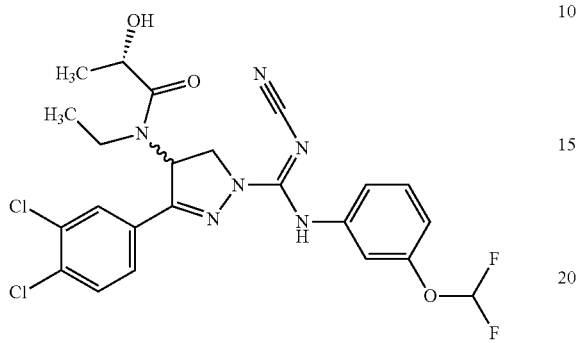

Example 8 was prepared analogously to example 4 using (2S)-2-{[tert-butyl(dimethyl)silyl]-oxy}propanoyl chloride instead of acetoxyacetyl chloride for the amide coupling. The silyl group was removed by treating the crude protected amide with 2 eq N,N,N-tributylbutan-1-aminium fluoride in tetrahydrofuran at room temperature for 45 min. The reaction mixture was concentrated and the residue was purified by HPLC (gradient of acetonitrile in 0.1% aqueous ammonia).

$^1$H-NMR (400 MHz, DMSO-d6): d [ppm]=1.08-1.17 (m, 6H), 3.34-3.48 (m, 1H), 3.63 (br. s., 1H), 4.08 (m, 1H), 4.27-4.41 (m, 1H), 4.44-4.58 (m, 1H), 4.98 (d, 0.5H), 5.18 (d, 0.5H), 6.99-7.07 (m, 1.25H), 7.20-7.30 (m, 2.5H), 7.39-7.48 (m, 1.25H), 7.62-7.70 (m, 1H), 7.75 (t, 1H), 8.09 (dd, 1H), 9.84 (br. s., 1H).

LCMS (method 2): $R_t$=1.22
MS (ESI): [M+H]$^+$=539.1

Example 9

(2R)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 Mixture of Diastereomers)

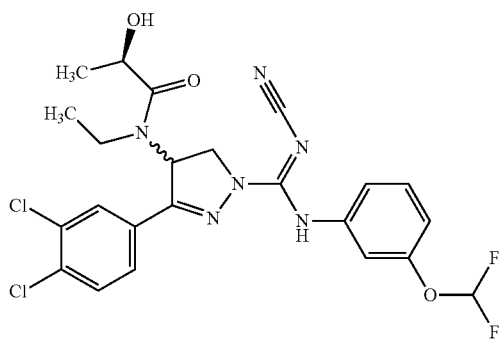 [SMILES: CCN(C(=O)[C@@H](C)O)C1CN(/C(=N\C#N)Nc2cccc(OC(F)F)c2)N=C1c1ccc(Cl)c(Cl)c1]

Example 9 was prepared analogously to example 8 using (2R)-2-{[tert-butyl(dimethyl)silyl]oxy}propanoyl chloride instead of acetoxyacetyl chloride for the amide coupling.

$^1$H-NMR corresponds to example 8.
LCMS (method 2): $R_t$=1.22
MS (ESI): [M+H]$^+$=539.1

Example 10

Rac-4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide

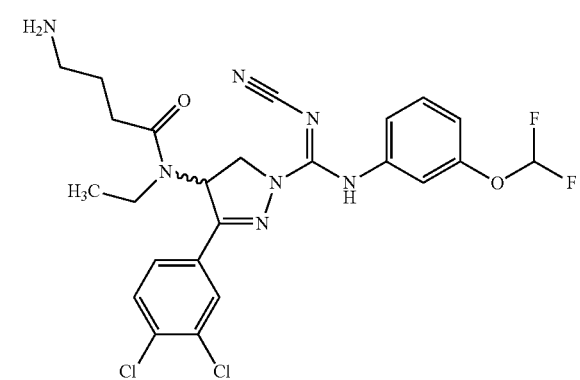 [SMILES: CCN(C(=O)CCCN)C1CN(/C(=N\C#N)Nc2cccc(OC(F)F)c2)N=C1c1ccc(Cl)c(Cl)c1]

Example 10 was prepared analogously to example 3 using Fmoc-4-aminobutanoic acid instead of Fmoc-glycine for the amide coupling.

$^1$H-NMR (400 MHz, DMSO-d$_6$): δ [ppm]=1.03 (t, 3H), 1.57 (m, 2H), 2.26-2.44 (m, 3H), 3.17-3.53 (m, 4H), 4.05 (dd, 1H), 4.36 (m, 1H), 6.84-6.88 (m, 1H), 7.01 (s, 0.25H), 7.09 (m, 2H), 7.19 (s, 0.5H), 7.32 (t, 1H), 7.38 (s, 0.25H), 7.61 (m, 3H), 7.72 (d, 1H), 7.99 (d, 1H).

LCMS (method 2): $R_t$=1.25 min
MS (ESI): [M+H]$^+$=552.1

Example 10 was subsequently separated into its enantiomers by the following sequence:

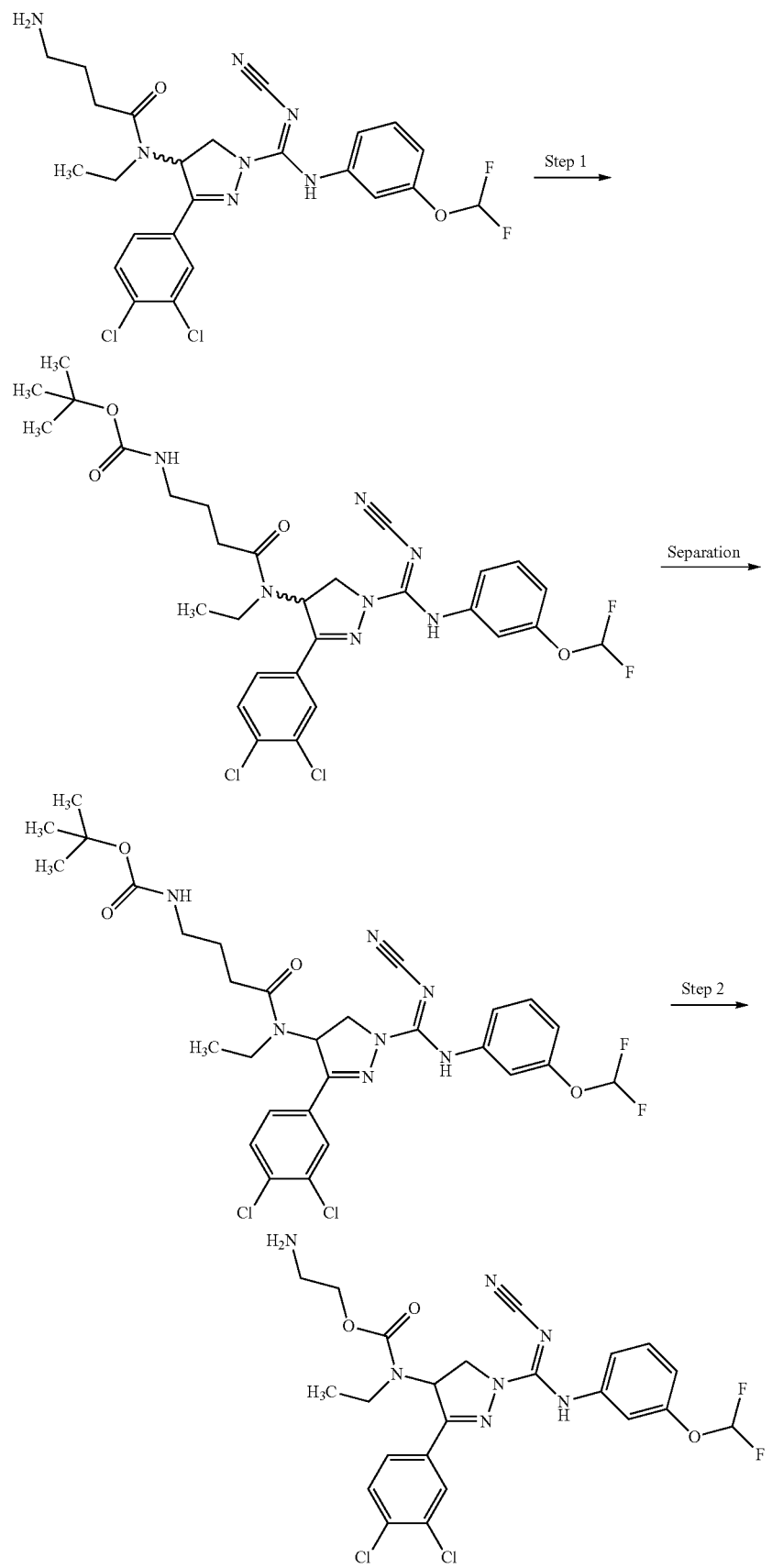

Step 1

Rac-tert-butyl (4-{[1-{N'-cyano-N-[3-(difluoromethoxy)phenyl]carbamimidoyl}-3-(3,4-dichlorophenyl)-4,5-dihydro-1H-pyrazol-4-yl](ethyl)amino}-4-oxobutyl)carbamate

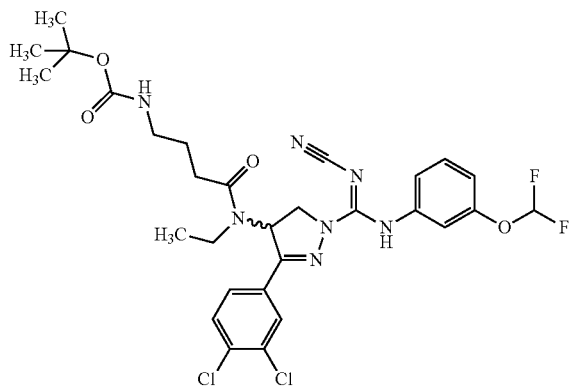 [SMILES: CCN(C(=O)CCCNC(=O)OC(C)(C)C)C1CN(/C(=N\C#N)Nc2cccc(OC(F)F)c2)N=C1c1ccc(Cl)c(Cl)c1]

To a cold (0° C.) stirred solution of 4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide (280 mg, 0.51 mmol) in dichloromethane (50 mL) was added N,N-diisopropylethylamine (0.265 mL, 1.5 mmol), followed by dropwise addition of di-tert-butyldicarbonate (0.116 mL, 0.51 mmol). The reaction was allowed to warm slowly to room temperature and stirred for 16 hours. After this time, water was added and the layers were separated. The aqueous phase was extracted with ethyl acetate and the combined organic phases were washed with brine, dried (MgSO$_4$) and evaporated to give the crude boc-protected amine. Purification of the crude material by silica gel chromatography gave tert-butyl (4-{[1-{N'-cyano-N-[3-(difluoromethoxy)phenyl]carbamimidoyl}-3-(3,4-dichlorophenyl)-4,5-dihydro-1H-pyrazol-4-yl](ethyl)amino}-4-oxobutyl)carbamate (280 mg, 79% yield) as a white solid.

$^1$H-NMR (400 MHz, DMSO-d$_6$): δ [ppm]=1.05 (br. s., 3H), 1.55 (br. s., 2H), 2.21-2.39 (m, 2H), 2.88 (br. d, 2H), 3.28 (br. s., 1H), 3.46 (br. s., 1H), 4.07-4.14 (m, 1H), 4.47 (t, 1H), 6.79 (br. t, 1H), 7.03 (dd, 1H), 7.21-7.29 (m, 3H), 7.41-7.46 (m, 1H), 7.52-7.68 (m, 2H), 7.76 (d, 1H), 8.12 (d, 1H), 9.86 (s, 1H).

LCMS (method 2): R$_t$=1.43 min

MS (ESI): [M+H]$^+$=652.3

Separation:

Separation of the racemic material by chiral preparative HPLC (conditions below) gave 105 mg (R$_t$=4.3-5.1 min) of one enantiomer and 108 mg (R$_t$=5.1-6.4 min) of the second enantiomer.

Step 2:

| System: | Agilent: Prep 1200, 2xPrep Pump, DLA, MWD, Gilson: Liquid Handler 215 |
|---|---|
| Column: | Chiralpak IE 5 μm 250 × 20 mm |
| Solvent: | Acetonitrile 100% + 0.1% Diethylamine |
| Flow: | 30 mL/min |
| Temperature: | RT |
| Detection: | UV 325 nm |

| Fraction | Rt in min |
|---|---|
| 1 | 4.3-5.1 |
| 2 | 5.1-6.4 |

Deprotection of the Boc-protected amines was carried out according to the following procedure: To a stirred solution of tert-butyl (4-{[1-{N'-cyano-N-[3-(difluoromethoxy)phenyl]carbamimidoyl}-3-(3,4-dichlorophenyl)-4,5-dihydro-1H-pyrazol-4-yl](ethyl)amino}-4-oxobutyl)carbamate (108 mg, 0.17 mmol) in 1,2-dichloroethane (10 mL) was added zinc bromide (75 mg, 0.33 mmol). The resulting mixture was stirred overnight at room temperature. After this time, the reaction mixture was diluted with dichloromethane, pH 10 buffer was added and the layers were separated. The aqueous phase was extracted with dichloromethane (3 times) and the combined organic phases were washed with brine, dried (MgSO$_4$) and evaporated to give the crude amine. Purification of the crude material by preparative HPLC gave 4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide (25 mg, 27% yield) as a white solid. Analytical data for both isomers can be found in below.

Example 10.1 (from Separation Fraction 2 Above)

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 1

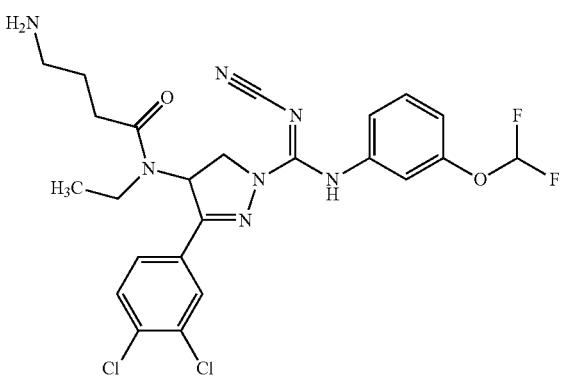 [SMILES: CCN(C(=O)CCCN)C1CN(/C(=N\C#N)Nc2cccc(OC(F)F)c2)N=C1c1ccc(Cl)c(Cl)c1]

[α]$_D$=−52.5° (c: 1.0, DMSO)

Example 10.2 (from Separation Fraction 1 Above)

4-amino-N-[1-{N'-cyano-N-[3-(difluoromethoxy) phenyl]carbamimidoyl}-3-(3,4-dichlorophenyl)-4,5-dihydro-1H-pyrazol-4-yl]-N-ethylbutanamide Isomer 2

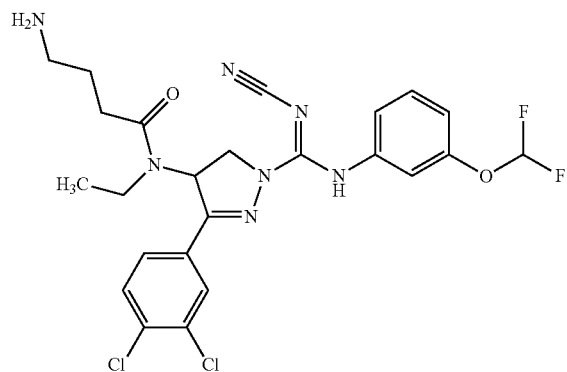 [SMILES: CCN(C(=O)CCCN)C1CN(/C(=N\C#N)Nc2cccc(OC(F)F)c2)N=C1c1ccc(Cl)c(Cl)c1]

$[\alpha]_D$=+59.6° (c: 1.0, DMSO)

Example 11

Rac-N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide

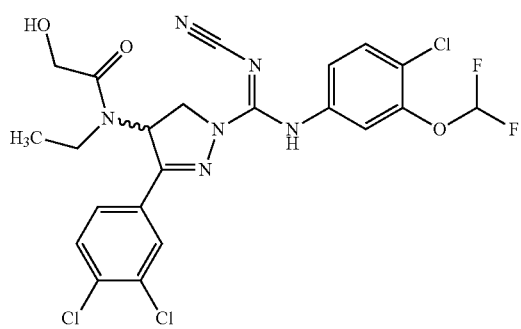 [SMILES: CCN(C(=O)CO)C1CN(/C(=N\C#N)Nc2ccc(Cl)c(OC(F)F)c2)N=C1c1ccc(Cl)c(Cl)c1]

Example 11 was prepared analogously to example 4 starting from intermediate 14 instead intermediate 12.

$^1$H-NMR (400 MHz, DMSO-d$_6$): δ [ppm]=0.81 (br. s., 1H), 0.99 (br. s., 3H), 2.92 (br. s., 0.4H), 3.01-3.29 (m, 3H), 3.94-4.33 (m, 6H), 4.40 (br. s., 0.4H), 4.72 (t, 1H), 5.13 (br. s., 0.3H), 5.73 (br. s., 0.4H), 5.94 (br. s., 1H), 6.93-7.42 (m, 6H), 7.52-7.72 (m, 3H), 7.86-7.96 (m, 1H).

LCMS (method 2): R$_t$=1.22 min
MS (ESI): [M+H]$^+$=559.2

Example 11 was separated into its diastereomers by chiral SFC:

| System: | Sepiatec: Prep SFC100 |
|---|---|
| Column: | Chiralpak IC 5 μm 250 × 20 mm |
| Solvent: | CO$_2$/Ethanol 70:30 |
| Flow: | 80 mL/min |
| Temperature: | 40° C. |
| Detection: | UV 254 nm |

| Example No | Rt in min |
|---|---|
| 11.1 | 4.75-5.60 |
| 11.2 | 6.25-7.50 |

Example 11.2 was further purified by chiral SFC:

| System: | Sepiatec: Prep SFC100 |
|---|---|
| Column: | Chiralpak IC 5 μm 250 × 20 mm |
| Solvent: | CO$_2$/Ethanol 70:30 |
| Flow: | 80 mL/min |
| Temperature: | 40° C. |
| Detection: | UV 254 nm |

| Example No | Rt in min |
|---|---|
| 11.2 | 4.50-5.60 |

Example 11.1

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 1

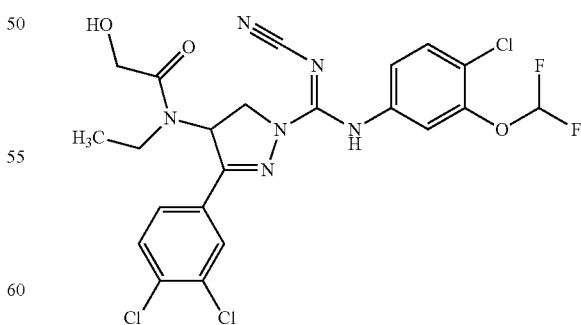

Chiralpak IC 5 μm 100×4.6 mm (CO$_2$/Ethanol, 70:30, 4.0 mL/min) R$_t$=2.99 min $[\alpha]_D$=−37.4° (c: 1.0, DMSO)

Example 11.2

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 2

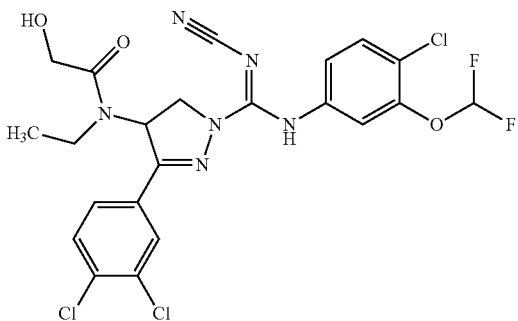 [SMILES: CCN(C(=O)CO)C1CN(/C(=N\C#N)Nc2ccc(Cl)c(OC(F)F)c2)N=C1c1ccc(Cl)c(Cl)c1]

Chiralpak IC 5 μm 100×4.6 mm (CO$_2$/Ethanol, 70:30, 4.0 mL/min) R$_t$=3.96 min
[α]$_D$=+41.2° (c: 1.0, DMSO)

Example 12

Rac-N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide

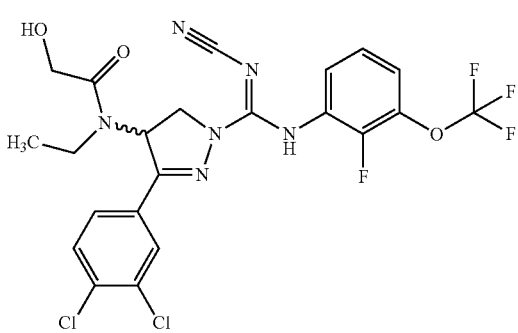 [SMILES: CCN(C(=O)CO)C1CN(/C(=N\C#N)Nc2cccc(OC(F)(F)F)c2F)N=C1c1ccc(Cl)c(Cl)c1]

Example 12 was prepared analogously to example 4 starting from intermediate 15 instead intermediate 12.

$^1$H-NMR (400 MHz, DMSO-d$_6$): δ [ppm]=1.09 (br. s., 3H), 4.00-4.14 (m, 3H), 4.44 (t, 1H), 4.77 (t, 1H), 7.34-7.40 (m, 1H), 7.47-7.59 (m, 2H), 7.63 (d, 1H), 7.76 (d, 1H), 8.13 (s, 1H), 9.95 (br. s., 1H).

LCMS (method 2): R$_t$=1.03 min
MS (ESI): [M+H]$^+$=561.0

Example 12 was separated into its diastereomers by chiral HPLC:

| System: | Agilent: Prep 1200, 2xPrep Pump, DLA, MWD, Prep FC |
|---|---|
| Column: | Chiralpak ID 5 μm 250 × 30 mm Nr. 018 |
| Solvent: | Hexan/Ethanol/Diethylamin 70:30:0.1 (v/v/v) |
| Flow: | 40 mL/min |
| Temperature: | RT |
| Detection: | UV 325 nm |

| Example No | Rt in min |
|---|---|
| 12.1 | 5.4-7.2 |
| 12.2 | 7.2-9.4 |

Example 12.1

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1

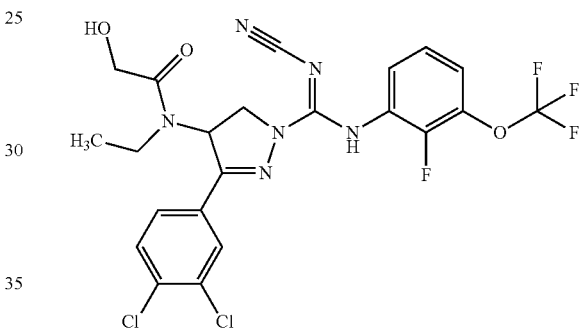

Chiralpak ID 3 μm 100×4.6 mm (Hexan/Ethanol/Diethylamine 70:30:0.1 (v/v/v), 1.0 mL/min) R$_t$=2.61 min
[α]$_D$=+27.4° (c: 1.0, DMSO)

Example 12.2

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2

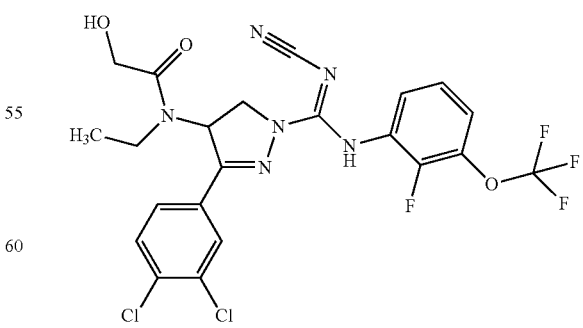

Chiralpak ID 3 μm 100×4.6 mm (Hexan/Ethanol/Diethylamine 70:30:0.1 (v/v/v), 1.0 mL/min) R$_t$=3.46 min
[α]$_D$=−22.9° (c: 1.0, DMSO)

Example 13

Rac-N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide

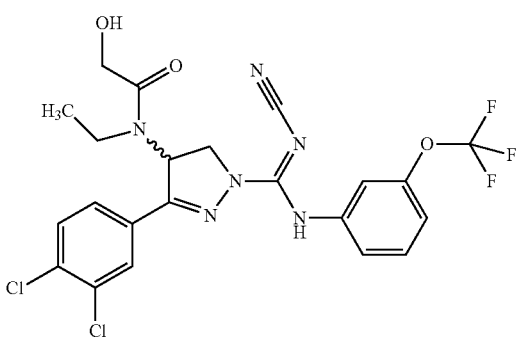 [SMILES: CCN(C(=O)CO)C1CN(/C(=N\C#N)Nc2cccc(OC(F)(F)F)c2)N=C1c1ccc(Cl)c(Cl)c1]

Example 13 was prepared analogously to example 4 starting from intermediate 16 instead intermediate 12.

$^1$H NMR (400 MHz, DMSO-$d_6$): δ [ppm]=1.03 (t, 3H), 3.3-3.5 (m, 2H), 3.9-4.1 (m, 3H), 4.4-4.5 (m, 1H), 4.7-4.8 (m, 1H), 7.15 (d, 1H), 7.3-7.8 (m, 6H), 8.09 (s, 1H), 9.88 (s, 1H)

LCMS (method 3): $R_t$=2.63

MS (ESI): [M+H]$^+$=542.92

Example 13 was separated into its enantiomers by chiral SFC:

| System: | Agilent: Prep 1200, 2 × Prep Pump, DLA, MWD, Gilson: Liquid Handler 215 |
|---|---|
| Column: | Chiralpak ID 5 μm 250 × 30 mm Nr.018 |
| Solvent: | Hexan/Ethanol 70:30 (v/v) |
| Flow: | 50 mL/min |
| Temperature: | RT |
| Detektion: | UV 254 nm |

| Example No | Rt in min |
|---|---|
| 13.1 | 10.8-13.8 |
| 13.2 | 16.8-21.4 |

Example 13.1

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1

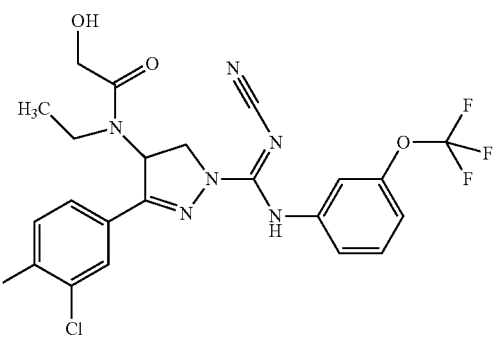

Chiralpak ID 3 m 100×4.6 mm (Hexan/Ethanol 70:30 (v/v); 1.0 mL/min) $R_t$=2.67 min

[α]$_D$=890 (C: 0.93, MeOH)

Example 13.2

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2

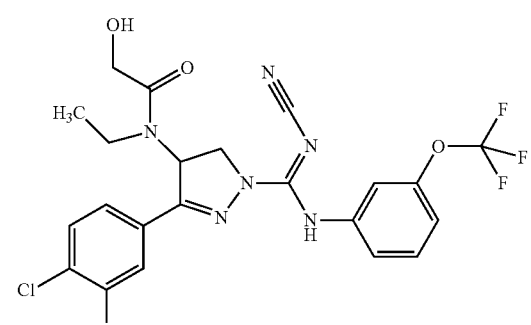

Chiralpak ID 3 μm 100×4.6 mm (Hexan/Ethanol 70:30 (v/v); 1.0 mL/min) $R_t$=3.66 min

[α]$_D$=−79° (c: 0.83, MeOH)

Example 14

Rac-N-[1-{N'-cyano-N-[4-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide

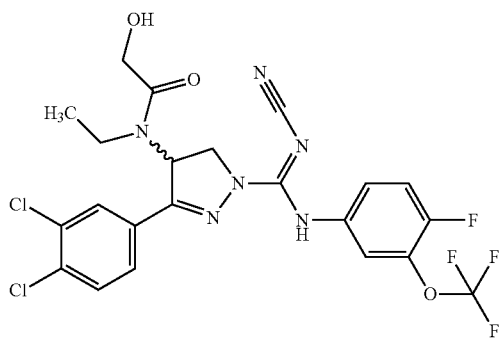 [SMILES: CCN(C(=O)CO)C1CN(/C(=N\C#N)Nc2ccc(F)c(OC(F)(F)F)c2)N=C1c1ccc(Cl)c(Cl)c1]

Example 14 was prepared analogously to example 4 starting from intermediate 17 instead intermediate 12.

$^1$H-NMR (400 MHz, DMSO-d$_6$): d [ppm]=1.06 (m, 3H), 3.16-3.30 (m, 2H, partially obscured by water signal), 3.98-4.20 (m, 3H), 4.37-4.52 (m, 1H), 4.76 (t, 1H), 5.83 (br. s., 1H), 7.34-7.60 (m, 3H), 7.60-7.68 (m, 1H), 7.73-7.77 (m, 1H), 8.10 (s, 1H), 9.87 (br. s., 1H).

LCMS (method 2): R$_t$=1.46

MS (ESI): [M+H]$^+$=561

Example 15

Rac-N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide

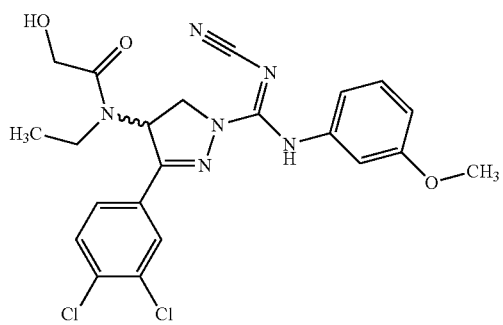 [SMILES: CCN(C(=O)CO)C1CN(/C(=N\C#N)Nc2cccc(OC)c2)N=C1c1ccc(Cl)c(Cl)c1]

Example 15 was prepared analogously to example 4 starting from intermediate 18 instead intermediate 12.

$^1$H-NMR (400 MHz, DMSO-d$_6$): δ [ppm]=1.04 (br. s., 3H), 3.14-3.27 (m, 1H), 3.74 (s, 3H), 3.99-4.14 (m, 4H), 4.38 (t, 1H), 4.69-4.75 (m, 1H), 5.85 (br. s., 1H), 6.84 (br. s., 4H), 7.20 (t, 1H), 7.51-7.64 (m, 2H), 7.69-7.73 (m, 1H), 8.07 (br. s., 1H), 9.75 (br. s., 1H).

LCMS (method 2): R$_t$=1.20 min

MS (ESI): [M+H]$^+$=489.2

Example 15 was separated into its diastereomers by chiral HPLC:

| System: | Agilent: Prep 1200, 2 × Prep Pump, DLA, MWD, Prep FC |
|---|---|
| Column: | Chiralpak IC 5 μm 250 × 20 mm Nr. 009 |
| Solvent: | Methanol/Ethanol/Diethylamin 50:50:0.1 (v/v/v) |
| Flow: | 20 mL/min |
| Temperature: | RT |
| Detection: | UV 325 nm |

| Example No | Rt in min |
|---|---|
| 15.1 | 6.75-8.0 |
| 15.2 | 5.0-6.0 |

Example 15.1

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 1

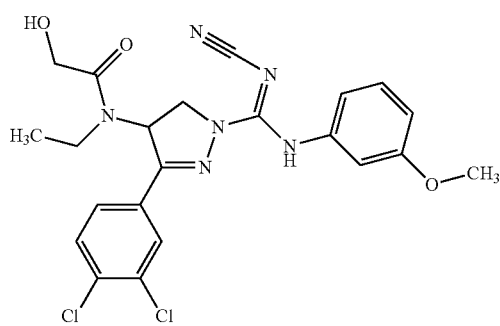 [SMILES: CCN(C(=O)CO)C1CN(/C(=N\C#N)Nc2cccc(OC)c2)N=C1c1ccc(Cl)c(Cl)c1]

Chiralpak IC 5 μm 150×4.6 mm (Methanol/Ethanol/Diethylamine 50:50:0.1 (v/v/v), 1.0 mL/min) R$_t$=3.47 min

[α]$_D$=+105.0° (c: 1.0, MeOH)

Example 15.2

N-{1-[N'-cyano-N-(3-methoxyphenyl)carbamimidoyl]-3-(3,4-dichlorophenyl)-4,5-dihydro-1H-pyrazol-4-yl]-N-ethyl-2-hydroxyacetamide Isomer 2

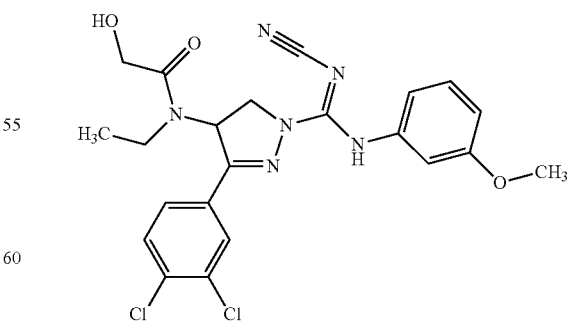

Chiralpak IC 5 μm 150×4.6 mm (Methanol/Ethanol/Diethylamine 50:50:0.1 (v/v/v), 1.0 mL/min) R$_t$=2.65 min

[α]$_D$=−88.1° (c: 1.0, MeOH)

Example 16

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide

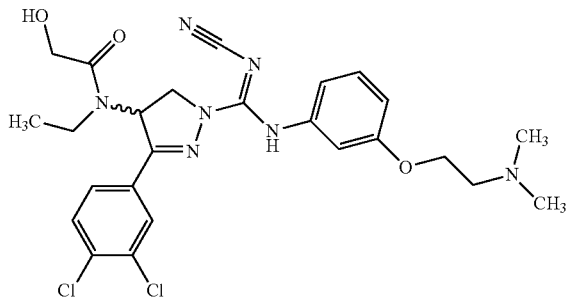 [SMILES: CCN(C(=O)CO)C1CN(/C(=N\C#N)Nc2cccc(OCCN(C)C)c2)N=C1c1ccc(Cl)c(Cl)c1]

Example 16 was prepared analogously to example 4 starting from intermediate 19 instead intermediate 12.

$^1$H-NMR (300 MHz, DMSO-$d_6$): δ [ppm]=1.02 (br. s., 3H), 2.19 (s, 6H), 2.60 (t, 2H), 3.94-4.45 (m, 8H), 5.84 (br. s., 1H), 6.46-6.85 (m, 4H), 7.16 (t, 1H), 7.50-7.75 (m, 7H), 8.02 (s, 1H).

LCMS (method 2): $R_t$=1.20 min
MS (ESI): [M+H]$^+$=546.24

Example 16 was separated into its diastereomers by chiral HPLC:

| | |
|---|---|
| System: | Agilent: Prep 1200, 2 × Prep Pump, DLA, MWD, Prep FC |
| Column: | Chiralpak IA 5 µm 250 × 20 mm |
| Solvent: | Methanol/Ethanol/Diethylamine 50:50:0.1 (v/v/v) |
| Flow: | 20 mL/min |
| Temperature: | RT |
| Detection: | UV 325 nm |

| Example No | Rt in min |
|---|---|
| 16.1 | 8.1-9.7 |
| 16.2 | 6.5-7.7 |

Example 16.1

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 1

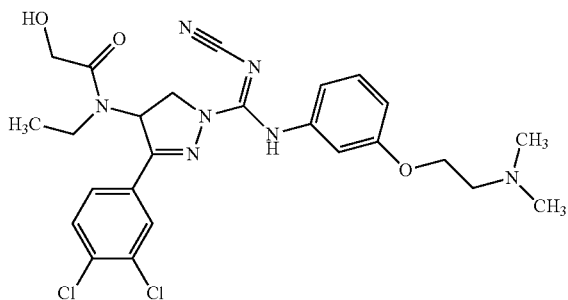 [SMILES: CCN(C(=O)CO)C1CN(/C(=N\C#N)Nc2cccc(OCCN(C)C)c2)N=C1c1ccc(Cl)c(Cl)c1]

Chiralpak IC 5 µm 150×4.6 mm (Methanol/Ethanol/Diethylamine 50:50:0.1 (v/v/v), 1.0 mL/min) $R_t$=4.51 min
[α]$_D$=+39.2° (c: 1.0, DMSO)

Example 16.2

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 2

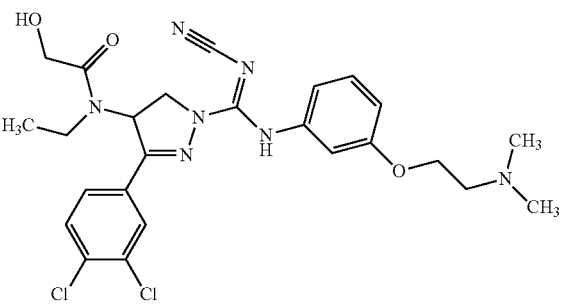 [SMILES: CCN(C(=O)CO)C1CN(/C(=N\C#N)Nc2cccc(OCCN(C)C)c2)N=C1c1ccc(Cl)c(Cl)c1]

Chiralpak IC 5 µm 150×4.6 mm (Methanol/Ethanol/Diethylamine 50:50:0.1 (v/v/v), 1.0 mL/min) $R_t$=3.53 min
[α]$_D$=−35.6° (c: 1.0, DMSO)

Example 17

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethylglycinamide

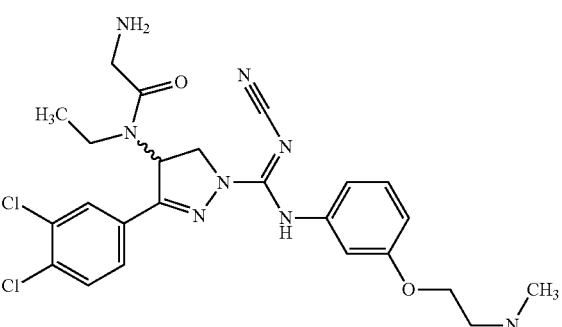

Example 17 was prepared analogously to example 3 starting from intermediate 19 instead intermediate 12.

$^1$H-NMR (400 MHz, METHANOL-$D_3$): d [ppm]=1.05-1.27 (m, 3H), 2.35 (s, 6H), 2.80 (t, 2H), 3.35 (m, 1H), 3.42-3.54 (m, 2H), 4.14 (t, 2H), 4.21 (dd, 1H), 4.40-4.50 (m, 1H), 6.87 (m, 1H), 6.98 (dd, 1H), 7.00-7.04 (m, 1H), 7.30 (t, 1H), 7.59 (d, 1H), 7.65 (dd, 1H), 8.11 (d, 1H); two hydrogens obscured by solvent or water signal.

LCMS (method 7): $R_t$=1.84
MS (ESI): [M]$^+$=545.18

Example 18

Rac-N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide

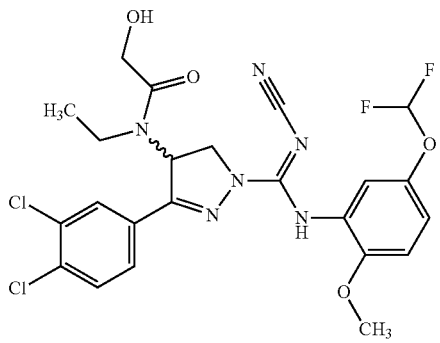 [SMILES: CCN(C(=O)CO)C1CN(/C(=N\C#N)Nc2cc(OC(F)F)ccc2OC)N=C1c1ccc(Cl)c(Cl)c1]

Example 18 was prepared analogously to example 4 starting from intermediate 30 instead intermediate 12.
LCMS (method 7): $R_t$=2.49
MS (ESI): [M+H]$^+$=555.2
Example 18 was separated into its enantiomers by chiral SFC:

| System: | Sepiatec: Prep SFC100, |
| --- | --- |
| Column: | Chiralpak ID 5 µm 250 × 20 mm |
| Solvent: | CO2/2-propanol 64/36 |
| Flow: | 80 mL/min |
| Temperature: | 40° C. |
| Detection: | UV 254 nm |
| Example No | Rt in min |
| 18.1 | 5.0-7.0 |
| 18.2 | 8.0-11.0 |

Example 18.1

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 1

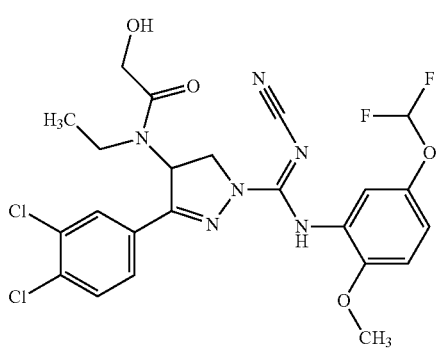 [SMILES: CCN(C(=O)CO)C1CN(/C(=N\C#N)Nc2cc(OC(F)F)ccc2OC)N=C1c1ccc(Cl)c(Cl)c1]

Chiralpak ID 5 µm 100×4.6 mm (CO2/2-Propanol 64/36, 4.0 mL/min) $R_t$=2.32 min
[α]$_D$=+52.5° (c: 0.3, DMSO)

Example 18.2

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 2

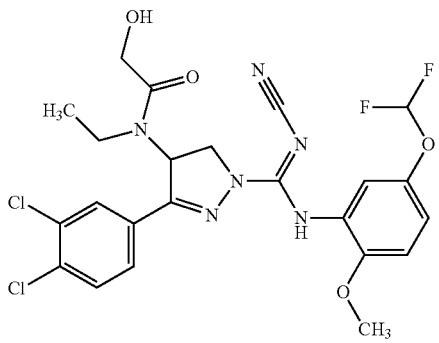 [SMILES: CCN(C(=O)CO)C1CN(/C(=N\C#N)Nc2cc(OC(F)F)ccc2OC)N=C1c1ccc(Cl)c(Cl)c1]

Chiralpak ID 5 m 100×4.6 mm (CO2/2-Propanol 64/36, 4.0 mL/min) $R_t$=3.93 min
[α]$_D$=−58.4° (c: 0.22, DMSO)

Example 19

Rac-N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide

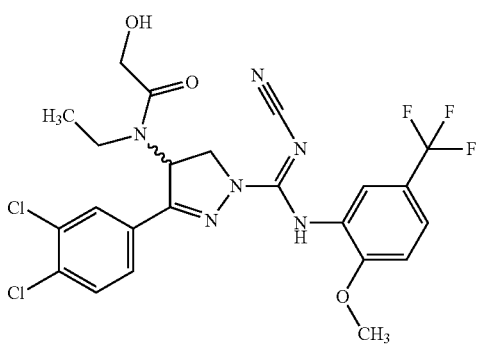

Example 19 was prepared analogously to example 4 starting from intermediate 31 instead intermediate 12.
$^1$H-NMR (400 MHz, DMSO-d$_6$): d [ppm]=1.06 (br. s., 3H), 3.91 (s, 3H), 3.96-4.16 (m, 3H), 4.37 (t, 1H), 4.78 (t, 1H), 7.29 (d, 1H), 7.61 (d, 1H), 7.64-7.72 (m, 2H), 7.75 (d, 1H), 8.13 (br. s., 1H), 9.68 (br. s., 1H). (2H obscured by water signal)

LCMS (method 6): $R_t$=0.84
MS (ESI): [M+H]$^+$=557.2

Example 19 was separated into its enantiomers by chiral SFC:

| System: | Sepiatec: Prep SFC100, |
|---|---|
| Column: | Chiralpak ID 5 μm 250 × 20 mm |
| Solvent: | CO2/2-propanol 65/35 |
| Flow: | 80 mL/min |
| Temperature: | 40° C. |
| Detection: | UV 254 nm |
| Example No | Rt in min |
| 19.1 | 4.0-5.5 |
| 19.2 | 6.5-8.0 |

Example 19.1

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1

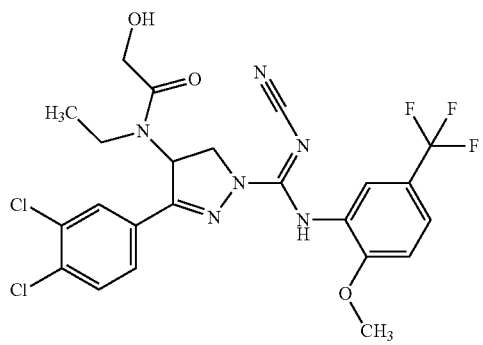 [SMILES: CCN(C(=O)CO)C1CN(/C(=N\C#N)Nc2cc(C(F)(F)F)ccc2OC)N=C1c1ccc(Cl)c(Cl)c1]

Chiralpak ID 5 μm 100×4.6 mm (CO2/2-Propanol 65/35, 4.0 mL/min) $R_t$=1.90 min
$[\alpha]_D$=+90.7° (c: 0.31, MeOH)

Example 19.2

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 2

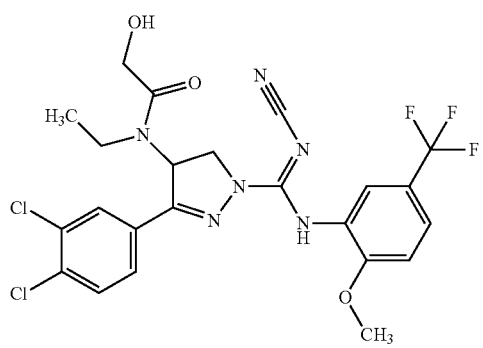 [SMILES: CCN(C(=O)CO)C1CN(/C(=N\C#N)Nc2cc(C(F)(F)F)ccc2OC)N=C1c1ccc(Cl)c(Cl)c1]

Chiralpak ID 5 m 100×4.6 mm (CO2/2-Propanol 65/35, 4.0 mL/min) $R_t$=3.28 min
$[\alpha]_D$=−91.2° (c: 0.37, MeOH)

Example 20

Rac-N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide

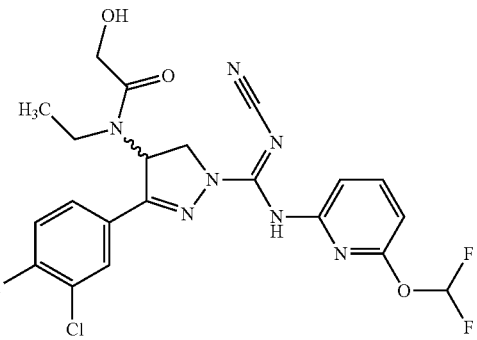

Example 20 was prepared analogously to example 4 starting from intermediate 20 instead intermediate 12.
LCMS (method 6): $R_t$=0.87
MS (ESI): [M+H]$^+$=526.14

Example 20 was separated into its enantiomers by chiral SFC:

| System: | Sepiatec: Prep SFC100, |
|---|---|
| Column: | Chiralpak ID 5 μm 250 × 20 mm |
| Solvent: | CO2/2-Propanol 71/29 |
| Flow: | 80 mL/min |
| Temperature: | 40° C. |
| Detection: | UV 254 nm |
| Example No | Rt in min |
| 20.1 | 3.5-5.0 |
| 20.2 | 5.0-7.0 |

Example 20.1

N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide Isomer 1

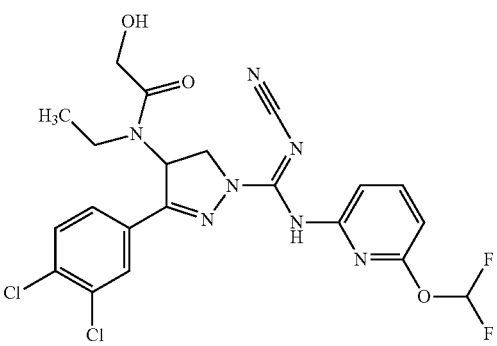 [SMILES: CCN(C(=O)CO)C1CN(/C(=N\C#N)Nc2cccc(OC(F)F)n2)N=C1c1ccc(Cl)c(Cl)c1]

Chiralpak ID 5 m 100×4.6 mm (CO2/2-Propanol 71/29, 4.0 mL/min) R$_t$=2.74 min

[α]$_D$=+69.7° (c: 0.29, DMSO)

Example 20.2

N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide Isomer 2

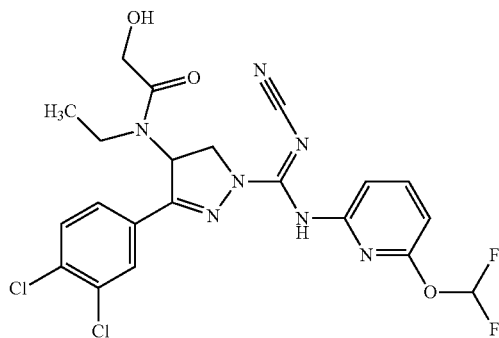 [SMILES: CCN(C(=O)CO)C1CN(/C(=N\C#N)Nc2cccc(OC(F)F)n2)N=C1c1ccc(Cl)c(Cl)c1]

Chiralpak ID 5 μm 100×4.6 mm (CO2/2-Propanol 71/29, 4.0 mL/min) R$_t$=3.82 min

[α]$_D$=−56.2° (c: 0.53, MeOH)

Example 21

Rac-N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide

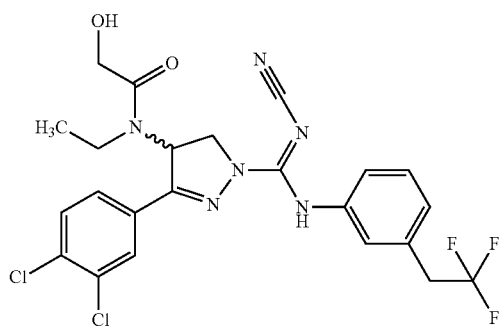 [SMILES: CCN(C(=O)CO)C1CN(/C(=N\C#N)Nc2cccc(CC(F)(F)F)c2)N=C1c1ccc(Cl)c(Cl)c1]

Example 21 was prepared analogously to example 4 starting from intermediate 21 instead intermediate 12.

MS (ESI): [M+H]$^+$=541

Example 21 was separated into its enantiomers by chiral SFC:

| System: | Sepiatec: Prep SFC100, |
|---|---|
| Column: | Chiralpak IC 5 μm 250 × 30 mm |
| Solvent: | CO2/Methanol 66/34 |
| Flow: | 100 mL/min |
| Temperature: | 40° C. |
| Detection: | UV 254 nm |

| Example No | Rt in min |
|---|---|
| 21.1 | 6.25-7.75 |
| 21.2 | 8.30-9.55 |

Example 21.1

N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide Isomer 1

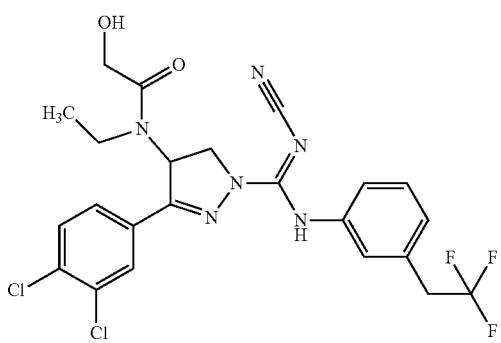 [SMILES: CCN(C(=O)CO)C1CN(/C(=N\C#N)Nc2cccc(CC(F)(F)F)c2)N=C1c1ccc(Cl)c(Cl)c1]

Chiralpak IC 5 μm 100×4.6 mm (CO2/Methanol 66/34, 4.0 mL/min) R$_t$=2.42 min

Example 21.2

N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide Isomer 2

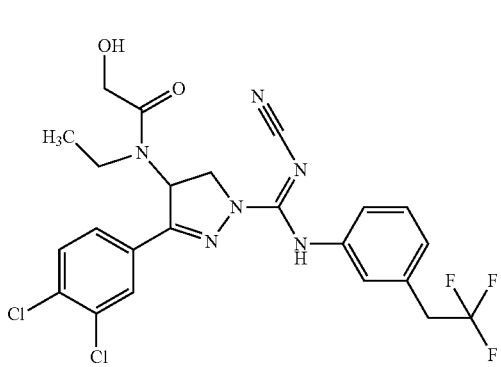 [SMILES: CCN(C(=O)CO)C1CN(/C(=N\C#N)Nc2cccc(CC(F)(F)F)c2)N=C1c1ccc(Cl)c(Cl)c1]

Chiralpak IC 5 μm 100×4.6 mm (CO2/Methanol 66/34, 4.0 mL/min) R$_t$=3.04 min

Example 22

Rac-N-[1-{N'-cyano-N-[3-(difluoromethoxy)-4-fluorophenyl]carbamimidoyl}-3-(3,4-dichlorophenyl)-4,5-dihydro-1H-pyrazol-4-yl]-N-ethyl-2-hydroxyacetamide

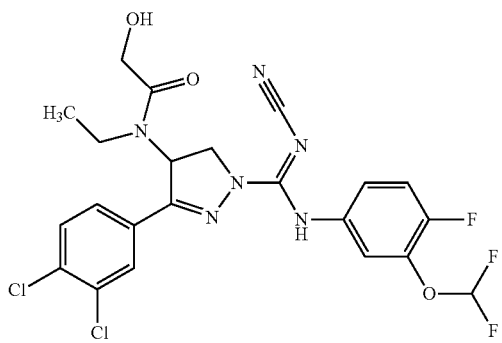 [SMILES: CCN(C(=O)CO)C1CN(/C(=N\C#N)Nc2ccc(F)c(OC(F)F)c2)N=C1c1ccc(Cl)c(Cl)c1]

Example 22 was prepared analogously to example 4 starting from intermediate 22 instead intermediate 12.

$^1$H-NMR (400 MHz, DMSO-$d_6$): d [ppm]=1.05 (m, 3H), 3.94-4.23 (m, 3H), 4.23-4.52 (m, 1H), 4.75 (m, 1H), 5.86 (br. s., 1H), 7.01-7.49 (m, 4H), 7.63 (d, 1H), 7.74 (d, 1H), 8.09 (br. s., 1H), 9.86 (br. s., 1H), two hydrogens obscured by solvent or water signal.

MS (ESI): [M+H]$^+$=543

Example 23

Rac-N-[1-{N'-cyano-N-[3-(difluoromethoxy)-2-fluorophenyl]carbamimidoyl}-3-(3,4-dichlorophenyl)-4,5-dihydro-1H-pyrazol-4-yl]-N-ethyl-2-hydroxyacetamide

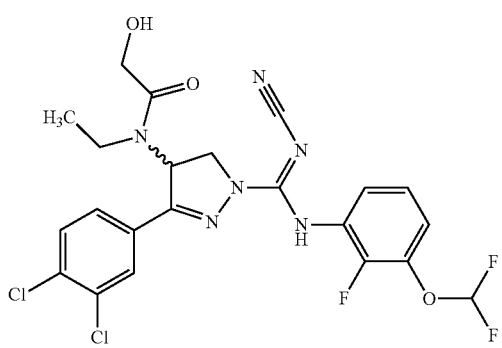 [SMILES: CCN(C(=O)CO)C1CN(/C(=N\C#N)Nc2cccc(OC(F)F)c2F)N=C1c1ccc(Cl)c(Cl)c1]

Example 23 was prepared analogously to example 4 starting from intermediate 36 instead intermediate 12.

$^1$H-NMR (400 MHz, DMSO-$d_6$): d [ppm]=1.07 (m, 3H), 3.89-4.18 (m, 3H), 4.32-4.48 (m, 1H), 4.74 (t, 1H), 5.79 (br. s., 1H), 7.15-7.36 (m, 4H), 7.61 (d, 1H), 7.74 (d, 1H), 8.10 (br. s., 1H). 9.82 (br. s., 1H)

MS (ESI): [M+H]$^+$=543

Example 24

Rac-N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide

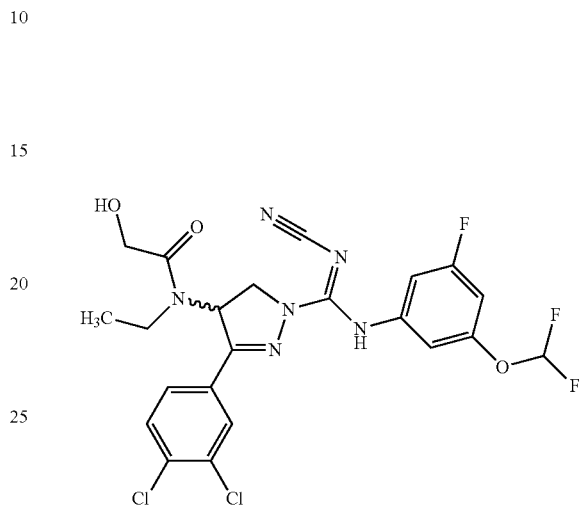

Example 24 was prepared analogously to example 4 starting from intermediate 23 instead intermediate 12.

$^1$H-NMR (400 MHz, DMSO-$d_6$): δ [ppm]=1.08 (br. s., 3H), 3.41 (br. s., 1H), 3.99-4.17 (m, 3H), 4.50 (t, 1H), 4.77 (t, 1H), 6.95 (d, 1H), 7.09 (br. s., 1H), 7.13 (s, 0.25H), 7.19 (d, 1H), 7.31 (s, 0.5H), 7.49 (s, 0.25H), 7.66 (d, 1H), 7.77 (d, 1H), 8.11 (s, 1H), 9.94 (br. s., 1H).

LCMS (method 2): $R_t$=1.06 min

MS (ESI): [M+H]$^+$=543.2

Example 24 was separated into its diastereomers by chiral HPLC:

| | |
|---|---|
| System: | Agilent: Prep 1200, 2 × Prep Pump, DLA, MWD, Prep FC |
| Column: | Chiralpak ID 5 µm 250 × 30 mm Nr. 018 |
| Solvent: | Hexane/Ethanol/Diethylamine 70:30:0.1 (v/v/v) |
| Flow: | 40 mL/min |
| Temperature: | RT |
| Detection: | UV 325 nm |

| Example No | Rt in min |
|---|---|
| 24.1 | 8.1-9.7 |
| 24.2 | 6.5-7.7 |

Example 24.1

N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide Isomer 1

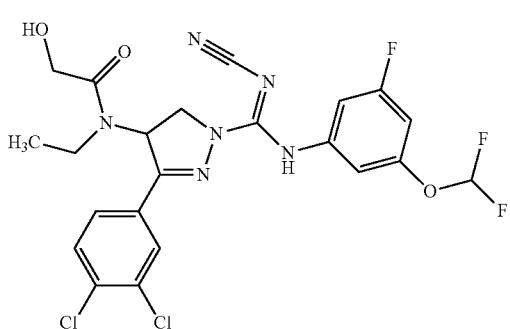 [SMILES: CCN(C(=O)CO)C1CN(/C(=N\C#N)Nc2cc(F)cc(OC(F)F)c2)N=C1c1ccc(Cl)c(Cl)c1]

Chiralpak ID 3 μm 100×4.6 mm (Hexan/Ethanol/Diethylamine 70:30:0.1 (v/v/v), 1.0 mL/min) $R_t$=2.68 min $[\alpha]_D$=+38.2° (c: 1.0, DMSO)

Example 24.2

N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide Isomer 2

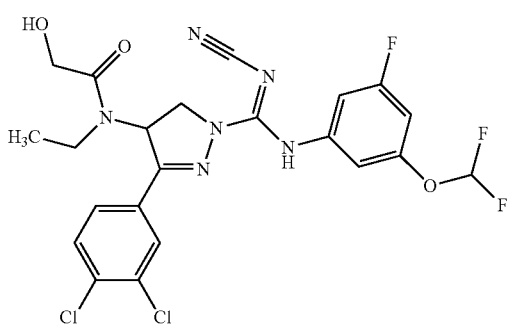 [SMILES: CCN(C(=O)CO)C1CN(/C(=N\C#N)Nc2cc(F)cc(OC(F)F)c2)N=C1c1ccc(Cl)c(Cl)c1]

Chiralpak ID 3 μm 100×4.6 mm (Hexan/Ethanol/Diethylamine 70:30:0.1 (v/v/v), 1.0 mL/min) $R_t$=3.81 min $[\alpha]_D$=−38.1° (c: 1.0, DMSO)

Example 25

Rac-N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Example 25 was prepared analogously to example 4 starting from intermediate 24 instead intermediate 12.

$^1$H-NMR (400 MHz, DMSO-$d_6$): δ [ppm]=0.79 (br. s., 1H), 0.99 (br. s., 3H), 2.99-3.21 (m, 1H), 3.96-4.16 (m, 3H), 4.18-4.44 (m, 2H), 4.70 (t, 1H), 5.12 (br. s., 1H), 5.80 (d, 1H), 6.59-6.88 (m, 1H), 6.92-7.12 (m, 2H), 7.52-7.64 (m, 1H), 7.68 (d, 1H), 7.86-7.95 (m, 1H).

LCMS (method 2): $R_t$=1.14 min

MS (ESI): $[M+H]^+$=561.3

Example 25 was separated into its diastereomers by chiral HPLC:

| | |
|---|---|
| System: | Agilent: Prep 1200, 2 × Prep Pump, DLA, MWD, Prep FC |
| Column: | Chiralpak IC 5 μm 250 × 30 mm Nr. 009 |
| Solvent: | Hexane/Ethanol/Diethylamine 70:30:0.1 (v/v/v) |
| Flow: | 40 mL/min |
| Temperature: | RT |
| Detection: | UV 325 nm |

| Example No | Rt in min |
|---|---|
| 25.1 | 11.4-13.4 |
| 25.2 | 20.9-23.6 |

111

Example 25.1

N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1

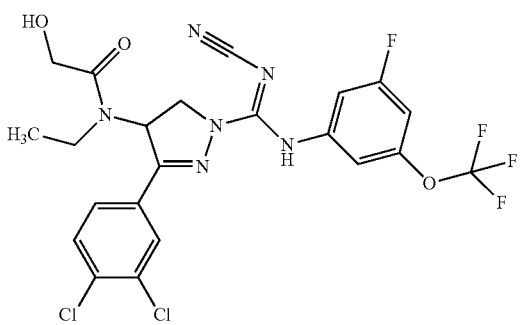 [SMILES: CCN(C(=O)CO)C1CN(/C(=N\C#N)Nc2cc(F)cc(OC(F)(F)F)c2)N=C1c1ccc(Cl)c(Cl)c1]

Chiralpak IC 3 µm 100×4.6 mm (Hexan/Ethanol/Diethylamine 70:30:0.1 (v/v/v), 1 mL/min) $R_t$=4.09 min $[\alpha]_D$=−35.8° (c: 1.0, DMSO)

Example 25.2

N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2

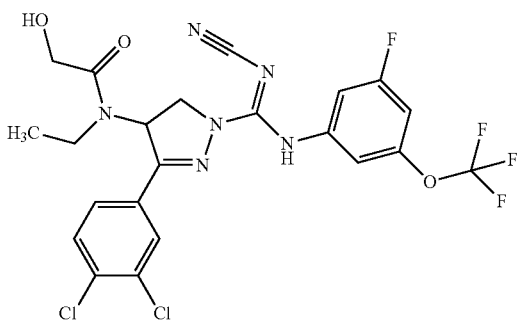 [SMILES: CCN(C(=O)CO)C1CN(/C(=N\C#N)Nc2cc(F)cc(OC(F)(F)F)c2)N=C1c1ccc(Cl)c(Cl)c1]

Chiralpak IC 3 µm 100×4.6 mm (Hexan/Ethanol/Diethylamine 70:30:0.1 (v/v/v), 1 mL/min) $R_t$=7.66 min $[\alpha]_D$=+32.7° (c: 1.0, DMSO)

112

Example 26

Rac-N-[1-{N'-cyano-N-[2-methoxy-5-(trifluoromethoxy)phenyl]carbamimidoyl}-3-(3,4-dichlorophenyl)-4,5-dihydro-1H-pyrazol-4-yl]-N-ethyl-2-hydroxyacetamide

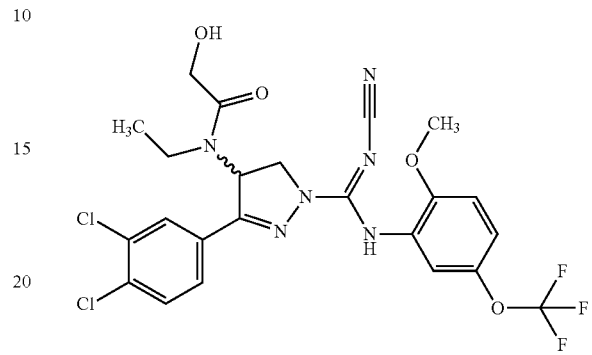

Example 26 was prepared analogously to example 4 starting from intermediate 37 instead intermediate 12.

$^1$H-NMR (400 MHz, DMSO-$d_6$): d [ppm]=1.07 (m, 3H), 3.17-3.47 (m, 2H, overlain by water signal), 3.85 (s, 3H), 3.94-4.16 (m, 3H), 4.38 (t, 1H), 4.75 (t, 1H), 5.79 (br. s., 1H), 7.15-7.21 (m, 1H), 7.29-7.35 (m, 1H), 7.37 (br. s., 1H), 7.61 (d, 1H), 7.75 (d, 1H), 8.12 (s, 1H), 9.61 (br. s., 1H).

MS (ESI): [M+H]$^+$=573

Example 27

Rac-N-[1-{N'-cyano-N-[2-(pyrrolidin-1-ylmethyl)-5-(trifluoromethyl)phenyl]carbamimidoy}-3-(3,4-dichlorophenyl)-4,5-dihydro-1H-pyrazol-4-yl]-N-ethyl-2-hydroxyacetamide

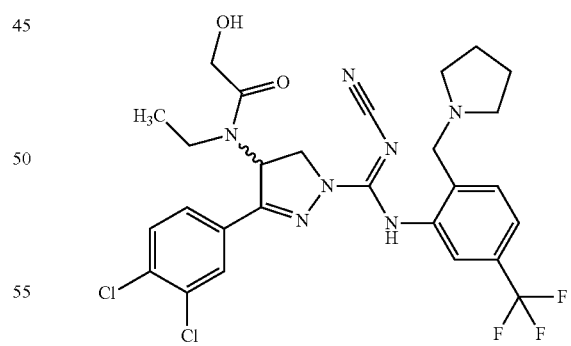

Example 27 was prepared analogously to example 4 starting from intermediate 25 instead intermediate 12.

$^1$H-NMR (300 MHz, DMSO-$d_6$): d [ppm]=1.09 (m, 3H), 1.68 (m, 4H), 3.16-3.55 (m, 3H), 3.78 (s, 2H), 3.95-4.26 (m, 3H), 4.52 (t, 1H), 5.83 (br. s., 1H), 7.39-7.65 (m, 3H), 7.78 (d, 1H), 7.91 (d, 2H); 10.95 (br. s., 1H); four hydrogens obscured by solvent or water signals.

MS (ESI): [M+H]$^+$=610

Example 27 was separated into its enantiomers by chiral SFC:

| System: | Sepiatec: Prep SFC100, |
| --- | --- |
| Column: | Chiralpak IC 5 µm 250 × 20 mm |
| Solvent: | CO2/Ethanol 63/37 |
| Flow: | 80 mL/min |
| Temperature: | 40° C. |
| Detection: | UV 254 nm |
| Example No | Rt in min |
| 27.1 | 3.10-3.85 |
| 27.2 | 4.25-5.20 |

Example 27.1

N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1

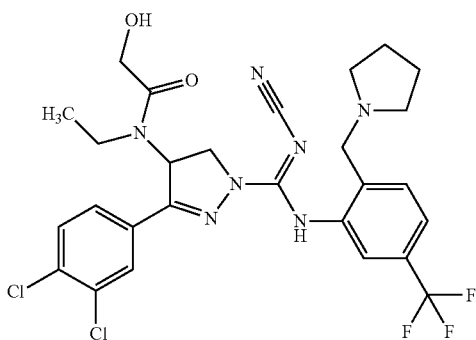 [SMILES: CCN(C(=O)CO)C1CN(/C(=N\C#N)Nc2cc(C(F)(F)F)ccc2CN2CCCC2)N=C1c1ccc(Cl)c(Cl)c1]

Chiralpak IC 5 µm 100×4.6 mm (CO2/Ethanol 63:37, 4.0 mL/min) $R_t$=3.69 min

Example 27.2

N-[1-{N'-cyano-N-[2-(pyrrolidin-1-Ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 2

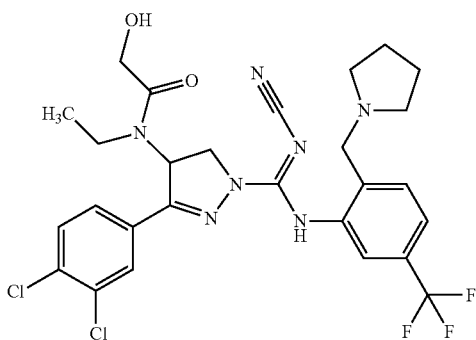 [SMILES: CCN(C(=O)CO)C1CN(/C(=N\C#N)Nc2cc(C(F)(F)F)ccc2CN2CCCC2)N=C1c1ccc(Cl)c(Cl)c1]

Chiralpak IC 5 µm 100×4.6 mm (CO2/Ethanol 63:37, 4.0 mL/min) $R_t$=5.62 min

Example 28

Rac-N-[1-{N'-cyano-N-[2-(trifluoromethoxy)-5-(trifluoromethyl)phenyl]carbamimidoyl}-3-(3,4-dichlorophenyl)-4,5-dihydro-1H-pyrazol-4-yl]-N-ethyl-2-hydroxyacetamide

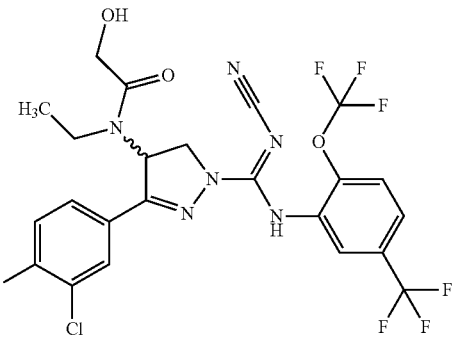

Example 28 was prepared analogously to example 4 starting from intermediate 26 instead intermediate 12.

LCMS (method 2): $R_t$=1.07

MS (ESI): [M+H]$^+$=610.7

Example 29

Rac-N-[1-(N'-cyano-N-{5-(difluoromethoxy)-2-[3-(dimethylamino)propoxy]phenyl}-carbamimidoyl)-3-(3,4-dichlorophenyl)-4,5-dihydro-1H-pyrazol-4-yl]-N-ethyl-2-hydroxyacetamide

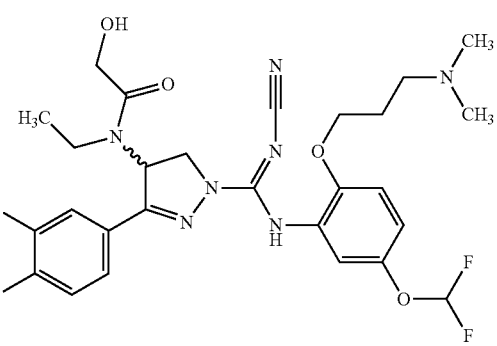

Example 29 was prepared analogously to example 4 starting from intermediate 38 instead intermediate 12.

LCMS (method 2): $R_t$=1.31

MS (ESI): [M+H]$^+$=626

Example 30

Rac-N-[r-(N'-cyano-N-[2-[2-(pyrrolidin-1-yl)ethoxy]-5-(trifluormethyl)phenyl]carbamimidoyl)-3-(3,4-dichlorophenyl)-4,5-dihydro-1H-pyrazol-4-yl]-N-ethyl-2-hydroxyacetamide

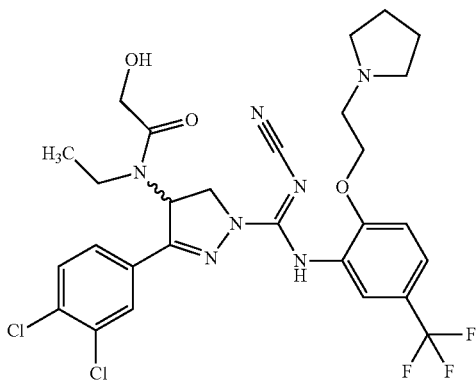 [SMILES: CCN(C(=O)CO)C1CN(/C(=N\C#N)Nc2cc(C(F)(F)F)ccc2OCCN2CCCC2)N=C1c1ccc(Cl)c(Cl)c1]

Example 30 was prepared analogously to example 4 starting from intermediate 27 instead intermediate 12.
LCMS (method): $R_t$=1.34
MS (ESI): [M+H]$^+$=640.3

Example 31

Rac-N-[1-(N'-cyano-N-{2-[(1-methylpiperidin-4-yl)oxy]-5-(trifluoromethyl)phenyl}-carbamimidoyl)-3-(3,4-dichlorophenyl)-4,5-dihydro-1H-pyrazol-4-yl]-N-ethyl-2-hydroxyacetamide

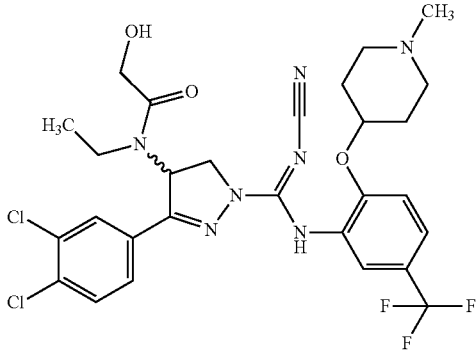 [SMILES: CCN(C(=O)CO)C1CN(/C(=N\C#N)Nc2cc(C(F)(F)F)ccc2OC2CCN(C)CC2)N=C1c1ccc(Cl)c(Cl)c1]

Example 31 was prepared analogously to example 4 starting from intermediate 39 instead intermediate 12.
LCMS (method 2): $R_t$=1.27
MS (ESI): [M+H]$^+$=640.4

Example 32

Rac-N-[1-(N'-cyano-N-{2-[(1-methylpiperidin-4-yl)oxy]-5-(trifluoromethyl)phenyl}-carbamimidoyl)-3-(3,4-dichlorophenyl)-4,5-dihydro-1H-pyrazol-4-yl]-N-ethyl-2-hydroxyacetamide

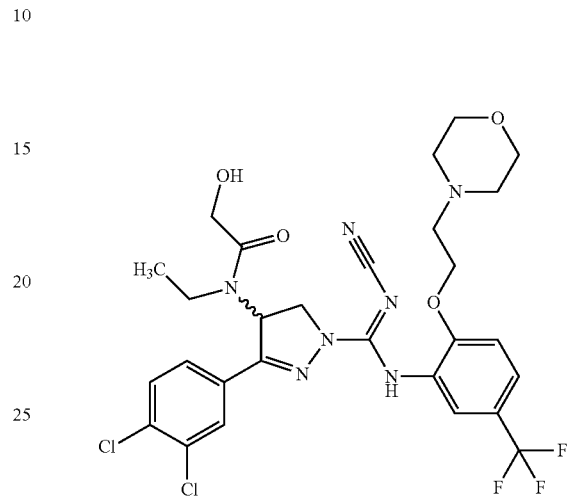

Example 32 was prepared analogously to example 4 starting from intermediate 28 instead intermediate 12.
LCMS (method 2): $R_t$=1.25
MS (ESI): [M+H]$^+$=656.3

Example 33

Rac-N-[3-(4-chloro-3-methylphenyl)-1-{N'-cyano-N-[3-(difluoromethoxy)phenyl]-carbamimidoyl}-4,5-dihydro-1H-pyrazol-4-yl]-N-ethyl-2-hydroxyacetamide

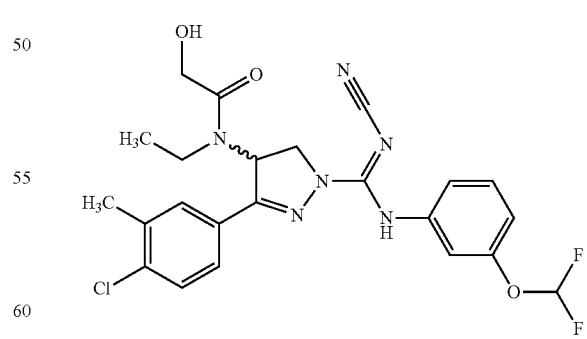

Example 33 was prepared analogously to example 4 starting from intermediate 13 instead intermediate 12.
LCMS (method 7): $R_t$=2.59
MS (ESI): [M+H]$^+$=505.0

Example 33 was separated into its enantiomers by chiral HPLC:

| System: | Agilent: Prep 1200, 2 × Prep Pump, DLA, MWD, Gilson: Liquid Handler 215 |
|---|---|
| Column: | Chiralpak ID 5 µm 250 × 30 mm Nr.: 018 |
| Solvent: | Hexan/Ethanol 70:30 (v/v) |
| Flow: | 50 mL/min |
| Temperature: | RT |
| Detection: | UV 280 nm |

| Example No | Rt in min |
|---|---|
| 33.1 | 7.2-9.0 |
| 33.2 | 10.9-12.9 |

Example 33.1

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-2-hydroxyacetamide Isomer 1

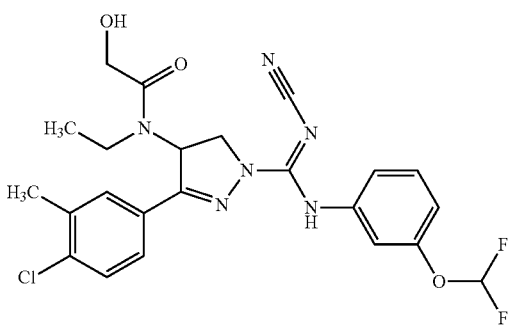 [SMILES: CCN(C(=O)CO)C1CN(/C(=N\C#N)Nc2cccc(OC(F)F)c2)N=C1c1ccc(Cl)c(C)c1]

Chiralpak ID 3 µm 100×4.6 mm (Hexan/Ethanol 70:30 (v/v), 1.0 mL/min) $R_t$=4.00 min
$[\alpha]_D$=+97.7° (c: 0.82, MeOH)

Example 33.2

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-2-hydroxyacetamide Isomer 2

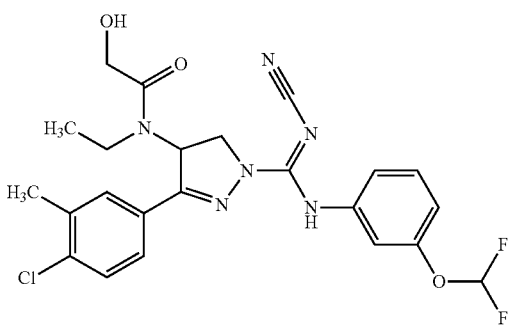 [SMILES: CCN(C(=O)CO)C1CN(/C(=N\C#N)Nc2cccc(OC(F)F)c2)N=C1c1ccc(Cl)c(C)c1]

Chiralpak ID 3 µm 100×4.6 mm (Hexan/Ethanol 70:30 (v/v), 1.0 mL/min) $R_t$=6.22 min
$[\alpha]_D$=−96.8° (c: 0.88, MeOH)

Example 34

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide (1:1 Mixture of Diastereomers)

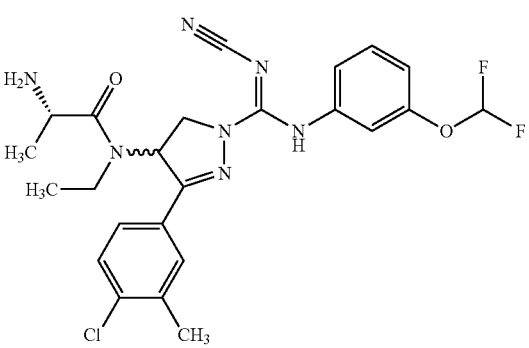 [SMILES: CCN(C(=O)[C@H](C)N)C1CN(/C(=N\C#N)Nc2cccc(OC(F)F)c2)N=C1c1ccc(Cl)c(C)c1]

Example 34 was prepared analogously to example 3 starting from intermediate 13 instead intermediate 12 and using Fmoc-L-alanine instead Fmoc-glycine for the amide coupling.

LCMS (method 2): $R_t$=0.94 and 0.96 (two diastereomers)
MS (ESI): $[M+H]^+$=518.1

Example 34 was separated into its diastereomers by chiral SFC:

| System: | Sepiatec: Prep SFC100, |
|---|---|
| Column: | Chiralpak IB 5 µm 250 × 30 mm |
| Solvent: | CO2/ethanol + 0.4% DEA 8/2 |
| Flow: | 100 mL/min |
| Temperature: | 40° C. |
| Detection: | UV 254 nm |

| Example No | Rt in min |
|---|---|
| 34.1 | 2.0-2.5 |
| 34.2 | 4.0-5.0 |

Example 34.1

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide Isomer 1

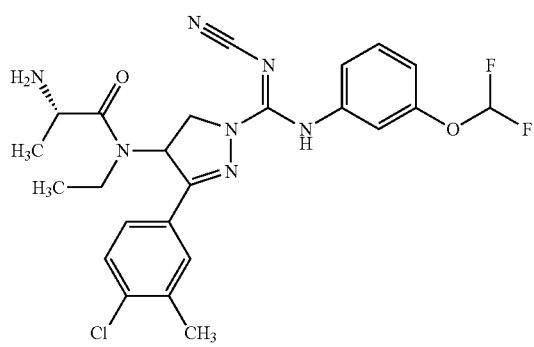 [SMILES: CCN(C(=O)[C@H](C)N)C1CN(/C(=N\C#N)Nc2cccc(OC(F)F)c2)N=C1c1ccc(Cl)c(C)c1]

Chiralpak IB 5 μm 100×4.6 mm (CO2/Ethanol+0.2% DEA, 4.0 mL/min) $R_t$=2.33 min

Example 34.2

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide Isomer 2

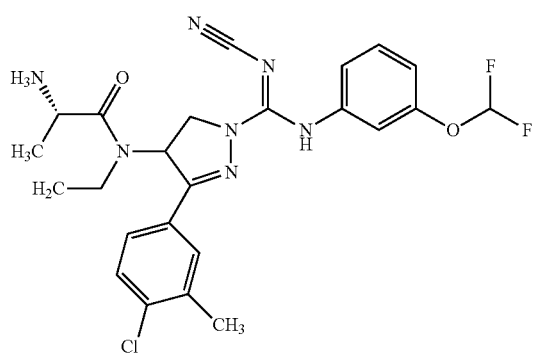 [SMILES: CCN(C(=O)[C@H](C)N)C1CN(/C(=N\C#N)Nc2cccc(OC(F)F)c2)N=C1c1ccc(Cl)c(C)c1]

Chiralpak TB 5 μm 100×4.6 mm (CO2/Ethanol+0.2% DEA, 4.0 mL/min) $R_t$=3.24 min

Example 35

Rac-N-[3-(4-chloro-3-fluorophenyl)-1-{N'-cyano-N-[3-(trifluoromethoxy)phenyl]-carbamimidoyl}-4,5-dihydro-1H-pyrazol-4-yl]-N-ethyl-2-hydroxyacetamide

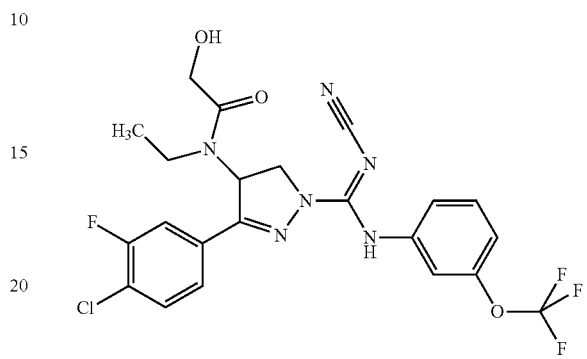

Example 35 was prepared analogously to example 4 starting from intermediate 29 instead intermediate 12.

LCMS (method 2): $R_t$=1.18

MS (ESI): [M+H]$^+$=526.8

Further, the compounds of formula (I) of the present invention can be converted to any salt as described herein, by any method which is known to the person skilled in the art. Similarly, any salt of a compound of formula (I) of the present invention can be converted into the free compound, by any method which is known to the person skilled in the art.

Example 36 rac-N-[3-(4-Chloro-3-methylphenyl)-1-{N'-cyano-N-[3-(difluoromethoxy)phenyl]carbamimidoyl}-4,5-dihydro-1H-pyrazol-4-yl]-N-ethyl-N$^2$-methylglycinamide

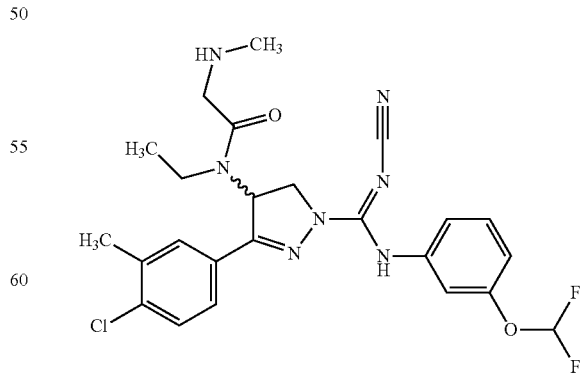

Example 36 was prepared starting from intermediate 13 according to the following scheme:

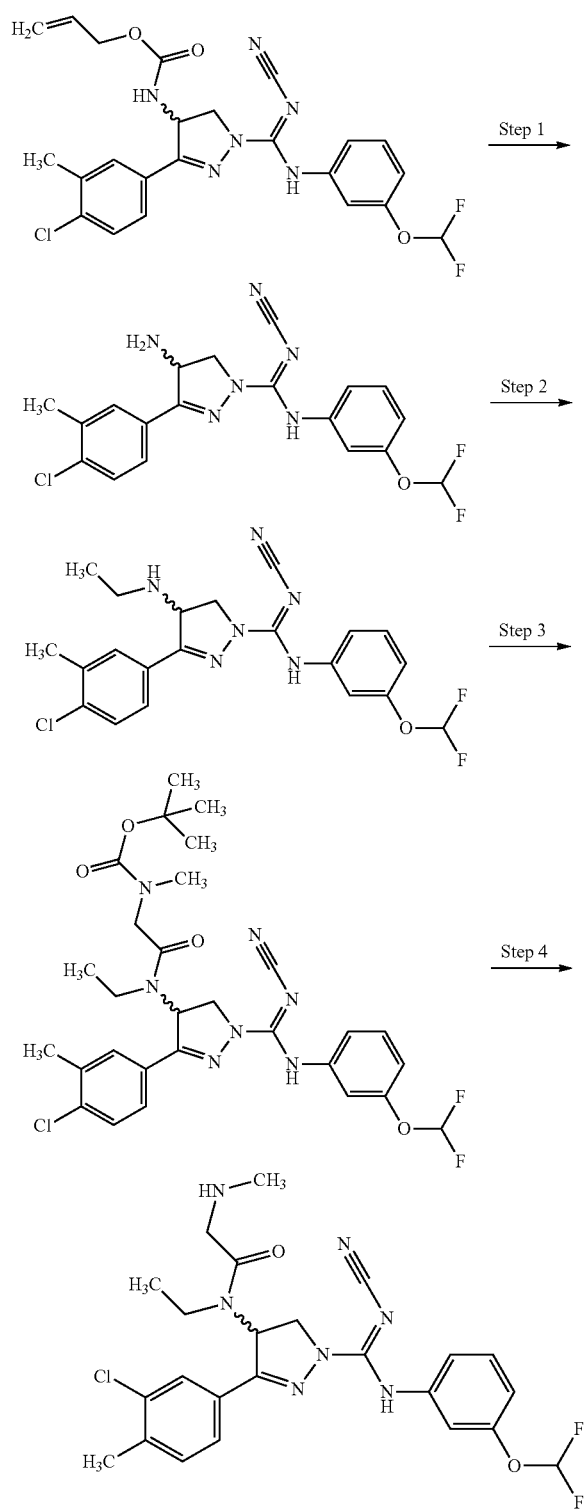

Step 1:

Step 1 was carried out analogously to step 1 described for example 3, starting from intermediate 13 to yield rac-4-amino-3-(4-chloro-3-methylphenyl)-N'-cyano-N-[3-(difluoromethoxy)phenyl]-4,5-dihydro-1H-pyrazole-1-caboximidamide.

$^1$H NMR (400 MHz, CDCl$_3$): δ [ppm]=2.43 (s, 3H), 4.37 (dd, 1H), 4.46 (dd, 1H), 4.87 (dd, 1H), 6.55 (t, 1H), 6.96 (dd, 1H), 7.22-7.29 (m, 2H), 7.29-7.56 (m, 3H), 7.60-7.69 (m, 2H), 7.75 (d, 1H), 8.17 (br s, 1H).

LCMS (method 3): R$_t$=1.63 min

MS (ESI): [M+H]$^+$=419.1

Step 2:

Step 1 was carried out analogously to step 2 described for example 3, to obtain rac-3-(4-chloro-3-methylphenyl)-N'-cyano-N-[3-(difluoromethoxy)phenyl]-4-(ethylamino)-4,5-dihydro-1H-pyrazole-1-carboximidamide.

$^1$H NMR (400 MHz, CDCl$_3$): δ [ppm]=1.11 (t, 3H), 2.43 (s, 3H), 2.61-2.71 (m, 2H), 4.32 (dd, 1H), 4.54 (dd, 1H), 4.81 (dd, 1H), 6.56 (t, 1H), 6.97 (dd, 1H), 7.21-7.43 (m, 4H), 7.67 (dd, 1H), 7.77 (d, 1H), 8.12 (br s, 1H).

LCMS (method 3): R$_t$=1.79 min

MS (ESI): [M+H]$^+$=445.1

Step 3:

To a solution of N-(tert-butoxycarbonyl)-N-methylglycine in DMF (3.0 mL) were added 1-[Bis-(dimethylamino)methylene]-1H-1,2,3-triazolo [4,5-b]pyridinium-3-oxid hexafluorophosphate (HATU), 255 mg (671 μmol) and 4-methylmorpholine (148 μL). After stirring for 30 min at room temperature was added rac-3-(4-chloro-3-methylphenyl)-N'-cyano-N-[3-(difluoromethoxy)phenyl]-4-(ethylamino)-4,5-dihydro-1H-pyrazole-1-carboximidamide (150 mg, 366 μmol). The reaction mixture stirred overnight at room temperature and was then purified by preparative HPLC (Waters XBrigde C18 5 μm 100×30 mm, 0.2% aqueous ammonia, acetonitrile) to give rac-tert-butyl-(2-{[(4S)-3-(4-chloro-3-methylphenyl)-1-{N'-cyano-N-[3-(difluoromethoxy)phenyl]carbamimidoyl}-4,5-dihydro-1H-pyrazol-4-yl](ethyl)amino}-2-oxoethyl)methylcarbamate, 120 mg (56%) as a white solid.

UPLC-MS (method 2): R$_t$=1.43 min

MS (ESI): [M+H]$^+$=618.4

Step 4:

To a solution of tert-butyl (2-{[(4S)-3-(4-chloro-3-methylphenyl)-1-{N'-cyano-N-[3-(difluoro-methoxy)phenyl]carbamimidoyl}-4,5-dihydro-1H-pyrazol-4-yl](ethyl)amino}-2-oxoethyl)methylcarbamate, 120 mg (194 μmol) in 1,2-dichloroethane (6 mL) was added zinc bromide, 87 mg (389 μmol). The reaction mixture stirred 3 h at 60° C. and was then diluted with an aqueous pH 10 buffer and dichloromethane. The organic layer was washed with brine, dried and concentrated under reduced pressure. The residue was purified by preparative HPLC (Waters XBrigde C18 5 μm 100×30 mm, 0.2% aqueous ammonia, acetonitrile) to give rac-N-[3-(4-Chloro-3-methylphenyl)-1-{N'-cyano-N-[3-(difluoromethoxy)phenyl]carbamimidoyl}-4,5-dihydro-1H-pyrazol-4-yl]-N-ethyl-N2-methylglycinamide, 40 mg (41%) as a white solid.

$^1$H-NMR (400 MHz, DMSO-d6) δ[ppm]: 0.756 (0.47), 0.775 (0.84), 0.793 (0.52), 1.052 (2.76), 1.329 (0.54), 2.128 (0.59), 2.168 (6.94), 2.323 (1.06), 2.327 (1.46), 2.331 (1.53), 2.347 (16.00), 2.361 (7.49), 2.363 (6.97), 2.523 (7.80), 2.539 (2.63), 2.665 (0.71), 2.669 (0.93), 2.674 (0.65), 3.219 (1.68), 3.260 (3.74), 3.362 (2.99), 3.464 (0.71), 3.502 (0.55), 4.082 (0.84), 4.094 (1.02), 4.113 (1.15), 4.125 (1.20), 4.431 (1.08), 4.460 (2.18), 4.490 (1.01), 6.980 (1.85), 6.987 (2.32), 7.001 (2.22), 7.008 (2.55), 7.056 (2.89), 7.205 (3.28), 7.210 (4.64), 7.216 (2.92), 7.241 (6.99), 7.250 (2.58), 7.265 (2.80), 7.267 (2.92), 7.392 (2.95), 7.412 (4.90), 7.426 (3.50), 7.433 (2.89), 7.452 (0.89), 7.497 (2.27), 7.518 (3.70), 7.560 (0.79), 7.578 (2.39), 7.580 (2.59), 7.583 (2.56), 7.599 (1.46), 7.604 (1.50), 7.774 (3.16), 7.776 (3.36), 7.780 (3.00), 7.923 (0.93), 7.925 (0.95).

UPLC-MS (method 2): R$_t$=1.20 min

MS (ESI): [M+H]$^+$=518.3

Example 36 was separated into its isomers by chiral preparative HPLC:

| System: | Agilent: Prep 1200, 2 × Prep Pump, DLA, MWD, Preparative FC, |
|---|---|
| Column: | Chiralpak IE 5 μm 250 × 20 mm |
| Solvent: | acetonitrile/ethanol 90:10 + 0.1% diethylamine |
| Flow: | 15 mL/min |
| Temperature: | room temperature |
| Detection: | UV 254 nm |
| solution injection | 36 mg/1.5 mL dichloromethane/methanol 1:1 8 × 0.2 mL |

| Example No | $R_t$ in min |
|---|---|
| 36.1 | 8.0-9.2 |
| 36.2 | 10.4-12.5 |

Analytical chiral HPLC method: Instrument: Agilent 1260/Agilent 1290; column: Chiralpak IE 3 μm 100×4.6 mm; eluent: acetonitrile/ethanol 90:10+0.1% diethylamine; flow 1.0 mL/min; temperature: 25° C.; solution: 1.0 mg/mL ethanol/methanol 1:1; injection: 5 μL; detection: DAD 254 nm.

Example 36.1

N-[3-(4-Chloro-3-methylphenyl)-1-{N'-cyano-N-[3-(difluoromethoxy)phenyl]carbamimidoyl}-4,5-dihydro-1H-pyrazol-4-yl]-N-ethyl-N2-methylglycinamide Isomer 2

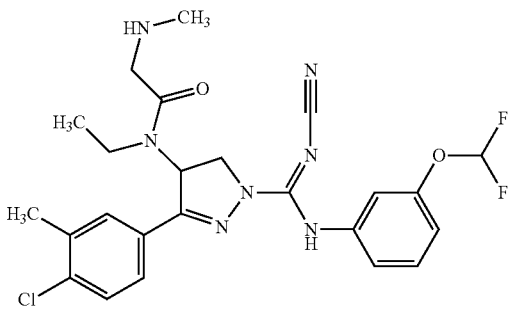 [SMILES: CCN(C(=O)CNC)C1CN(/C(=N\C#N)Nc2cccc(OC(F)F)c2)N=C1c1ccc(Cl)c(C)c1]

Analytical chiral HPLC: $R_t$=2.72 min
$[\alpha]_D^{20}$=+61.6° (c: 0.33 DMSO)

Example 36.2

N-[3-(4-Chloro-3-methylphenyl)-1-{N'-cyano-N-[3-(difluoromethoxy)phenyl]carbamimidoyl}-4,5-dihydro-1H-pyrazol-4-yl]-N-ethyl-N2-methylglycinamide Isomer 1

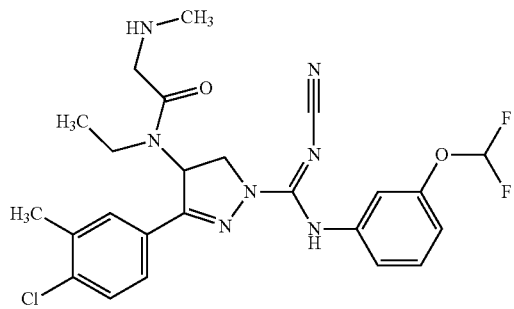 [SMILES: CCN(C(=O)CNC)C1CN(/C(=N\C#N)Nc2cccc(OC(F)F)c2)N=C1c1ccc(Cl)c(C)c1]

Analytical chiral HPLC: $R_t$=3.55 min
$[\alpha]_D^{20}$=−64.0° (c: 0.37, DMSO)

Example 37

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-N2-methyl-D-alaninamide

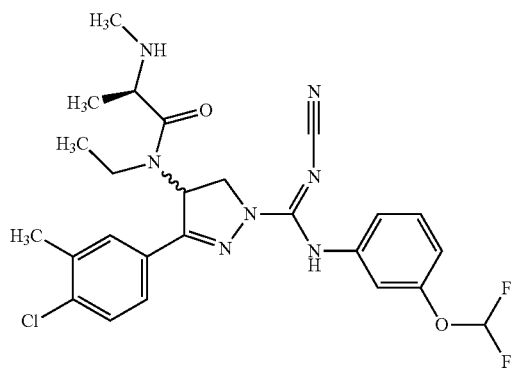 [SMILES: CCN(C(=O)[C@@H](C)NC)C1CN(/C(=N\C#N)Nc2cccc(OC(F)F)c2)N=C1c1ccc(Cl)c(C)c1]

Example 37 was prepared analogously to example 3 starting from intermediate 13 instead intermediate 12 and using N-[(9H-fluoren-9-ylmethoxy)carbonyl]-D-alanine instead N-[(9H-fluoren-9-ylmethoxy)carbonyl]glycine for the amide coupling.

$^1$H-NMR (400 MHz, DMSO-d6) δ[ppm]: 0.754 (0.43), 0.772 (0.83), 0.790 (0.54), 0.811 (0.41), 0.863 (0.45), 0.970 (1.08), 1.014 (5.72), 1.020 (3.18), 1.030 (5.97), 1.036 (2.95), 1.110 (4.87), 1.128 (1.62), 1.147 (1.15), 1.160 (1.19), 1.176 (1.01), 1.197 (0.47), 1.235 (1.10), 1.278 (0.43), 1.292 (0.52), 1.295 (0.52), 1.775 (0.47), 1.808 (0.47), 1.907 (0.70), 1.919 (0.79), 1.951 (0.74), 2.045 (0.41), 2.131 (11.88), 2.140 (3.90), 2.145 (1.42), 2.162 (2.77), 2.264 (0.56), 2.322 (2.95), 2.336 (16.00), 2.355 (3.81), 2.358 (3.99), 2.417 (0.52), 2.523 (4.33), 2.660 (0.50), 2.664 (0.99), 2.669 (1.44), 2.674 (1.06), 2.679 (0.61), 2.693 (0.45), 2.938 (1.08), 2.956 (1.10), 3.090 (1.31), 3.103 (1.22), 3.204 (0.52), 3.386 (0.99), 3.405 (1.60), 3.422 (1.78), 3.437 (1.60), 3.453 (1.24), 3.474 (0.59), 3.975 (0.47), 4.163 (0.41), 4.471 (0.95), 4.501 (1.60), 4.529 (0.72), 5.371 (0.77), 5.435 (0.77), 6.991 (1.71), 6.998 (2.37), 7.012 (2.25), 7.019 (2.61), 7.053 (4.21), 7.214 (3.49), 7.220 (6.35), 7.226 (3.90), 7.238 (8.65), 7.254 (2.79), 7.255 (3.27), 7.261 (2.43), 7.274 (3.43), 7.279 (3.70), 7.281 (3.15), 7.300 (1.13), 7.303 (1.10), 7.319 (0.79), 7.322 (0.74), 7.355 (0.61), 7.370 (0.86), 7.389 (0.47), 7.400 (3.47), 7.420 (6.11), 7.423 (7.35), 7.441 (2.70), 7.493 (2.93), 7.514 (4.15), 7.551 (0.41), 7.572 (0.56), 7.581 (1.44), 7.587 (1.55), 7.602 (1.04), 7.608 (1.10), 7.623 (1.22), 7.644 (0.88), 7.696 (0.99), 7.716 (1.98), 7.718 (2.05), 7.723 (1.76), 7.756 (1.87), 7.762 (1.78), 7.843 (1.15), 7.860 (1.15), 7.891 (0.61), 7.893 (0.59).
UPLC-MS (method 2): $R_t$=1.20 min
MS (ESI): [M+H]$^+$=518.3

Example 38

N-[1-{N'-cyano-N-[3-(difluoromethoxy)phenyl]carbamimidoyl}-3-(3,4-dichlorophenyl)-4,5-dihydro-1H-pyrazol-4-yl]-3-methyl-D-isovalinamide

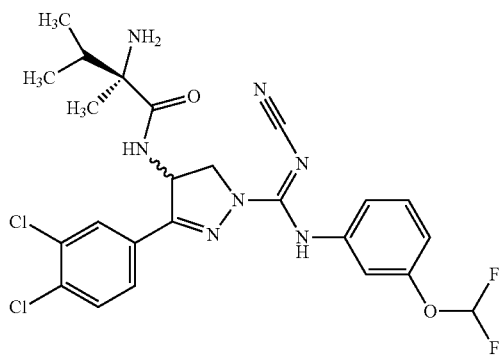 [SMILES: CC(C)[C@@](C)(N)C(=O)NC1CN(/C(=N\C#N)Nc2cccc(OC(F)F)c2)N=C1c1ccc(Cl)c(Cl)c1]

Example 38 was prepared analogously to example 3, omitting step 2 and using N-[(9H-fluoren-9-yl-methoxy)carbonyl]-3-methyl-D-isovaline instead of N-[(9H-fluoren-9-ylmethoxy)carbonyl]glycine to give N-[1-{N'-cyano-N-[3-(difluoromethoxy)phenyl]carbamimidoyl}-3-(3,4-dichlorophenyl)-4,5-dihydro-1H-pyrazol-4-yl]-3-methyl-D-isovalinamid as a white solid.

$^1$H-NMR (400 MHz, DMSO-d6) δ[ppm]: 0.564 (6.16), 0.581 (6.49), 0.600 (5.47), 0.617 (5.57), 0.718 (6.76), 0.727 (6.51), 0.735 (7.61), 0.744 (6.04), 1.021 (16.00), 1.025 (13.30), 1.109 (2.48), 1.251 (0.56), 1.852 (0.51), 1.870 (1.30), 1.887 (1.99), 1.905 (1.88), 1.923 (1.13), 1.940 (0.42), 2.073 (1.02), 2.523 (2.19), 2.532 (0.97), 2.537 (0.78), 4.016 (1.00), 4.030 (1.07), 4.044 (1.23), 4.054 (1.25), 4.058 (1.40), 4.066 (0.99), 4.082 (0.98), 4.095 (0.95), 4.429 (0.93), 4.436 (1.10), 4.457 (2.15), 4.464 (2.53), 4.486 (0.93), 4.493 (1.05), 5.741 (0.85), 5.754 (1.01), 5.763 (1.07), 5.769 (1.27), 5.777 (1.17), 5.783 (1.06), 5.792 (0.92), 5.805 (0.73), 6.998 (1.90), 7.000 (1.97), 7.003 (1.98), 7.005 (2.05), 7.019 (2.22), 7.025 (2.26), 7.061 (3.00), 7.202 (1.94), 7.208 (4.12), 7.213 (3.97), 7.219 (1.68), 7.246 (6.08), 7.255 (1.67), 7.261 (2.25), 7.275 (1.89), 7.280 (2.78), 7.407 (3.32), 7.427 (6.05), 7.448 (2.37), 7.733 (3.16), 7.736 (3.51), 7.754 (3.93), 7.758 (4.69), 7.846 (2.32), 7.851 (2.26), 7.868 (1.72), 7.872 (1.87), 7.876 (2.09), 7.881 (1.84), 7.897 (1.36), 7.902 (1.38), 8.142 (3.27), 8.147 (3.19), 8.154 (2.89), 8.159 (2.69).
LC-MS (method 9): $R_t$=1.05 min
MS (ESI): [M+H]$^+$=552.0

Example 38 was separated into its isomers by chiral SFC:

| System: | Sepiatec: Prep SFC100, |
|---|---|
| Column: | Chiralpak ID 5 μm 250 × 30 mm |
| Solvent: | carbon dioxide/2-propnaol + 0.2% diethylamine 70/30 |
| Flow: | 100 mL/min |
| Temperature: | 40° C. |
| Detection: | UV 254 nm |
| Pressure | 150 bar |
| solution | 240 mg/4 mL methanol/DMSO 3:1 |
| injection | 8 × 0.5 mL |

| Example No | $R_t$ in min |
|---|---|
| 38.1 | 6.5-9.0 |
| 38.2 | 14.0-18.0 |

Analytical chiral HPLC method: Instrument: Agilent: 1260 AS, MWD, Aurora SFC-Modul; column: Chiralpak IC 5 μm 100×4.6 mm; eluent: carbon dioxide/2-propnaol+0.2% diethylamine 70:30; flow 4.0 mL/min; temperature: 37.5° C.; solution: 1.0 mg/mL ethanol/methanol 1:1; injection: 10 μL; detection: DAD 254 nm.

Example 38.1

N-[1-{N'-cyano-N-[3-(difluoromethoxy)phenyl]carbamimidoyl}-3-(3,4-dichlorophenyl)-4,5-dihydro-1H-pyrazol-4-yl]-3-methyl-D-isovalinamide Isomer 2

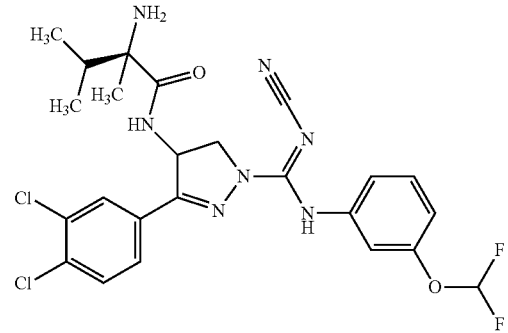 [SMILES: CC(C)[C@@](C)(N)C(=O)NC1CN(/C(=N\C#N)Nc2cccc(OC(F)F)c2)N=C1c1ccc(Cl)c(Cl)c1]

Analytical chiral HPLC: $R_t$=3.78 min
[α]$_D^{20}$=+34.0° (c: 0.22, DMSO)

Example 38.2

N-[1-{N'-Cyano-N-[3-(difluoromethoxy)phenyl]carbamimidoyl}-3-(3,4-dichlorophenyl)-4,5-dihydro-1H-pyrazol-4-yl]-3-methyl-D-isovalinamide
Isomer 1

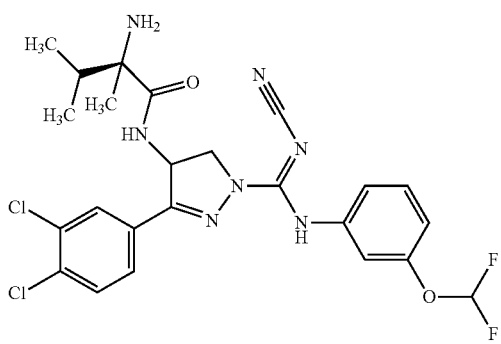 [SMILES: CC(C)[C@@](C)(N)C(=O)NC1CN(/C(=N\C#N)Nc2cccc(OC(F)F)c2)N=C1c1ccc(Cl)c(Cl)c1]

Analytical chiral HPLC: $R_t$=7.41 min
$[\alpha]_D^{20}$=+16.6° (c: 0.28, DMSO)

Example 39

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-D-leucinamide

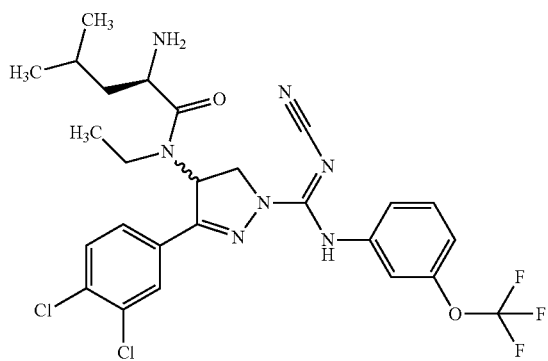 [SMILES: CCN(C(=O)[C@H](N)CC(C)C)C1CN(/C(=N\C#N)Nc2cccc(OC(F)(F)F)c2)N=C1c1ccc(Cl)c(Cl)c1]

Example 38 was prepared analogously to example 3, starting from intermediate 16 using N-[(9H-fluoren-9-ylmethoxy)carbonyl]-D-leucine instead of N-[(9H-fluoren-9-ylmethoxy)carbonyl]glycine to give N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-D-leucinamide.

UPLC-MS (method 2): $R_t$=1.41 min
MS (ESI): [M+H]$^+$=598.3

Example 40

N-[1-{N'-Cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-D-valinamide

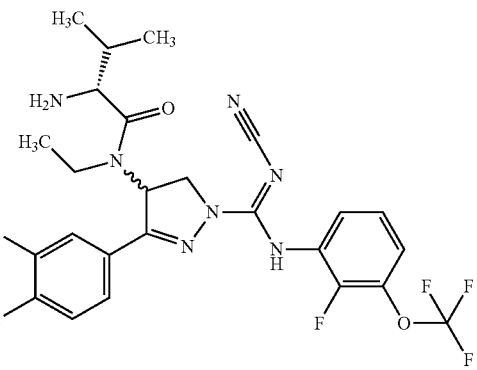

Example 40 was prepared analogously to example 3, starting from intermediate 15 and using N-[(9H-fluoren-9-ylmethoxy)carbonyl]-D-valine instead of N-[(9H-fluoren-9-ylmethoxy)carbonyl]glycine to give N-[1-{N'-Cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-D-valinamide.

$^1$H-NMR (400 MHz, CHLOROFORM-d) δ [ppm]: 0.658 (0.58), 0.675 (0.57), 0.895 (5.94), 0.912 (6.12), 0.952 (0.73), 0.974 (5.65), 0.991 (5.61), 1.193 (1.44), 1.212 (2.63), 1.229 (1.45), 1.261 (1.37), 1.825 (0.69), 1.842 (1.06), 1.859 (0.99), 1.875 (0.61), 2.015 (16.00), 3.259 (2.00), 3.275 (2.07), 3.299 (0.61), 3.319 (0.50), 3.328 (0.40), 4.531 (0.41), 4.615 (0.53), 7.192 (0.90), 7.207 (3.10), 7.216 (0.88), 7.223 (1.52), 7.226 (1.52), 7.247 (0.49), 7.502 (2.22), 7.523 (3.68), 7.577 (1.52), 7.582 (1.55), 7.597 (0.90), 7.603 (0.96), 7.813 (2.55), 7.818 (2.48), 7.920 (0.74), 7.925 (0.61), 7.938 (0.80), 7.943 (0.86), 7.945 (0.87), 7.954 (0.46), 7.962 (0.43).

UPLC-MS (method 2): $R_t$=1.06
MS (ESI): [M+H]$^+$=602.3

Example 41

N-[1-{N'-Cyano-N-[3-(difluoromethoxy)phenyl]carbamimidoyl}-3-(3,4-dichlorophenyl)-4,5-dihydro-1H-pyrazol-4-yl]-N-ethyl-D-valinamide

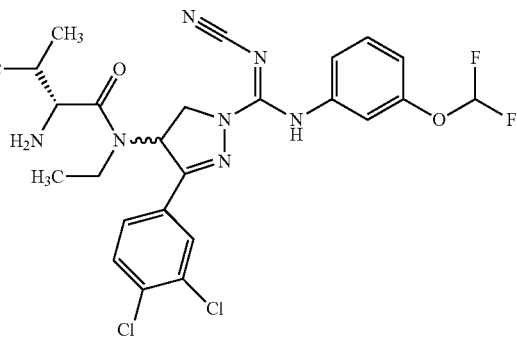

Example 41 was prepared analogously to example 3 using N-[(9H-fluoren-9-ylmethoxy)carbonyl]-D-valine instead of N-[(9H-fluoren-9-ylmethoxy)carbonyl]glycine to give N-[1-{N'-Cyano-N-[3-(difluoromethoxy)phenyl]carbamimidoyl}-3-(3,4-dichlorophenyl)-4,5-dihydro-1H-pyrazol-4-yl]-N-ethyl-D-valinamide.

$^1$H-NMR (400 MHz, DMSO-d6) δ[ppm]: 0.466 (3.32), 0.528 (0.67), 0.545 (0.58), 0.629 (0.44), 0.682 (4.75), 0.699 (4.81), 0.770 (0.70), 0.793 (0.64), 0.811 (0.52), 0.868 (1.08), 0.886 (2.10), 0.903 (1.52), 0.920 (3.18), 0.932 (13.29), 0.940 (15.80), 0.949 (14.43), 0.958 (14.05), 1.036 (0.99), 1.054 (1.54), 1.071 (3.91), 1.088 (7.72), 1.109 (4.93), 1.126 (1.17), 1.140 (0.96), 1.157 (0.79), 1.210 (2.30), 1.229 (4.23), 1.246 (2.91), 1.754 (0.85), 2.034 (1.17), 2.051 (1.81), 2.066 (1.75), 2.071 (2.56), 2.084 (1.25), 2.101 (0.55), 2.322 (1.19), 2.327 (1.72), 2.332 (1.22), 2.336 (0.61), 2.523 (5.60), 2.665 (1.17), 2.669 (1.72), 2.674 (1.14), 2.679 (0.58), 3.355 (1.14), 3.373 (1.31), 3.395 (1.11), 3.412 (0.79), 3.727 (0.96), 3.745 (1.14), 3.769 (0.99), 3.787 (0.73), 4.100 (2.74), 4.114 (3.35), 4.137 (3.96), 4.152 (2.94), 4.166 (2.68), 4.181 (2.71), 4.239 (1.84), 4.268 (2.21), 4.301 (1.31), 4.469 (2.68), 4.498 (4.49), 4.528 (2.42), 4.571 (1.95), 4.600 (3.44), 4.629 (1.98), 6.991 (0.55), 7.019 (2.56), 7.026 (2.80), 7.034 (3.03), 7.041 (5.74), 7.046 (3.85), 7.055 (3.38), 7.060 (8.66), 7.063 (9.59), 7.149 (0.41), 7.177 (0.50), 7.189 (3.35), 7.195 (6.18), 7.201 (3.67), 7.228 (4.26), 7.233 (6.91), 7.238 (5.07), 7.245 (15.07), 7.248 (16.00), 7.257 (1.63), 7.265 (3.64), 7.271 (6.35), 7.276 (3.44), 7.290 (3.67), 7.296 (3.50), 7.415 (5.01), 7.425 (5.80), 7.430 (6.38), 7.432 (7.87), 7.436 (8.54), 7.446 (8.28), 7.456 (3.93), 7.466 (3.64), 7.473 (0.79), 7.581 (0.44), 7.586 (0.52), 7.602 (0.70), 7.607 (0.64), 7.700 (3.61), 7.706 (2.65), 7.712 (3.82), 7.717 (4.08), 7.721 (6.99), 7.726 (6.59), 7.733 (5.62), 7.738 (6.12), 7.747 (11.77), 7.769 (4.43), 7.784 (0.70), 7.798 (9.62), 7.819 (5.89), 7.990 (4.26), 8.021 (6.82), 8.026 (6.64), 8.064 (0.70), 8.127 (7.46), 8.132 (7.69), 8.168 (4.23), 8.254 (1.60), 8.259 (1.84), 8.278 (0.85), 9.832 (3.32), 9.951 (4.02), 10.040 (1.02).

LC-MS (method 5): $R_t$=1.02 and 1.04 min (2 diastereomers)

MS (ESI): [M+H]$^+$=566.1

Comparison Example

To show superiority of the inventive compounds over the closest state of the art compounds that have been disclosed in WO 2006/072350, the following comparison example has been done:

| Example No. | Structure | IC$_{50}$ [mol/l] (SPA Assay) |
|---|---|---|
| 4.1 of the instant invention | (structure shown with 3,4-dichlorophenyl and 3-difluoromethoxyphenyl groups) | 2.82E-8 |
| WO 2006/072350 Example 67 more active isomer | (structure shown with 4-chlorophenyl and 3-difluoromethoxyphenyl groups) | 5.48E-7 |

Purification, Crystallization and Crystal Structure Determination of Human SMYD2 in Complex with SAM and Example 4.1

Purification of Human SMYD2

Recombinant human SMYD2 (Uniprot Q9NRG4; amino acids 2-433) was expressed in insect cells (Sf9) containing a N-terminal TEV-cleavable 6×His-tag. Cell pellets were re-suspended in lysis buffer (40 mM Tris, pH8; 500 mM NaCl; 0.1% IGEPAL; 5 mM imidazole; 1 mM DTT) supplemented with complete EDTA-free protease inhibitor tablets and 50 U/mL benzonase. The cell lysate was loaded onto a Ni-NTA column, eluted with imidazole and concentrated using an ultra centrifugal filter unit. Subsequently SMYD2 was gel filtrated on a Superdex S200 column equilibrated in 20 mM Tris (pH 8), 100 mM NaCl, 5% glycerol, 1 mM DTT. The 6×His-tag was cleaved with TEV protease in solution overnight at 6° C. Uncleaved SMYD2 and TEV protease were separated from the cleaved product by applying a second Ni-NTA affinity step. The cleaved SMYD2 protein was further purified by a second gel filtration step using a Superdex 200 equilibrated in 20 mM Tris (pH 8), 150 mM NaCl, 5% glycerol, 1 mM TCEP. The protein was concentrated to 15.5 mg/mL (313 μM) (UV-Vis) using an ultra centrifugal filter unit and shock frozen in liquid nitrogen.

Crystallization of Human SMYD2

For crystallization, the co-factor S-adenosyl methionine (SAM) was added to a final concentration of 3.8 mM as follows: 1.2 μl of a SAM stock solution (100 mM in DMSO) were added to 30 μl of concentrated SMYD2 solution and incubated for 2 hours at 4° C. Crystals grew within 3 days at 20° C. using the hanging drop method. Drops were made from 1 μl SMYD2:SAM solution and 0.8 μl reservoir solution (20-24% (w/v) PEG 3350, 100 mM HEPES pH 7.0). 30 min after drop set-up, 0.2 μl of a seed solution were added. The seed solution was made from SMYD2:SAM crystals (obtained with same reservoir conditions in a previous experiment) which were crashed manually (using Seed Beads, Hampton Research), diluted in reservoir solution, shock frozen and stored at −80° C.

Complex Formation of Human SMYD2:SAM and Example 4.1 in the Crystal

For complex formation, a crystal was transferred into a new drop of 1.5 yl reservoir solution. A stock solution of Example 4.1 (100 mM in DMSO) was 10-fold diluted with reservoir solution. Over the course of 2 hours, 1.5 μl of this diluted stock solution were added in three steps of 0.5 μl to the drop containing the SMYD2:SAM crystal, resulting in a final concentration of 5 mM Example 4.1 in the soaking drop. The crystal was soaked in this drop for 4 days at 20° C.

Data Collection and Processing

The soaked crystal was briefly immersed in cryo buffer (0.1 M HEPES pH 7.0, 22% PEG 3350, 20% glycerol and 2 mM Example 4.1) and shock frozen in liquid nitrogen. A diffraction data set was collected at beamline 14.1 at Helmholtz-Zentrum Berlin at 100 K using a wavelength of 0.91841 Å and a PILATUS detector. The diffraction images were processed using the program XDS. The crystal diffracted to a resolution of 2.0 Å and belonged to space group $P2_12_12_1$ with unit cell dimensions of a=52.3 Å and b=69.6 Å, c=131.1 Å with one molecule per asymmetric unit.

Structure Determination and Refinement

The crystal form described here was first solved for a SMYD2:SAM crystal in the absence of an inhibitor, using the Molecular Replacement method with the program PHASER from the CCP4 program suite and 3TG5 (PDB entry code) as search model. The data set for SMYD2:SAM: Example 4.1 was then solved by rigid body refinement using the SMYD2:SAM structure as starting model and the program REFMAC as part of the CCP4 program suite. A 3D model for Example 4.1 was generated using the program Discovery Studio and parameter files for crystallographic refinement and model building were generated using software PRODRG. Example 4.1 was manually built into the electron density maps using the program COOT, followed by several cycles of refinement (using program REFMAC) and rebuilding in COOT. The final co-complex structure features a R(work) of 23.0% and R(free) of 27.3%. The statistics of the data collection and refinement are summarized in Table 1.

TABLE 1

Data collection and refinement statistics for human SMYD2 in complex with SAM and Example 4.1

| | SMYD2:SAM:Example 4.1 |
|---|---|
| Data Collection: | |
| Source | BL 14.1 (Helmholtz-Zentrum Berlin) |
| Wavelength [Å] | 0.9841 |
| Space group (no.) | P2(1)2(1)2(1) (19) |
| Unit cell parameters, a, b, c [Å] | 52.3, 69.6, 131.1 |
| Resolution limit [Å] | 48.61-1.99 (2.11-1.99) |
| No. of reflections | 221439 |
| No. of uniques | 33656 |
| Multiplicity | 6.58 |
| I/sigI | 14.39 (2.41) |
| R_meas [%] | 10.1 (81.5) |
| Completeness [%] | 99.9 (99.5) |
| B (Wilson) [Å$^2$] | 35.09 |
| Mosaicity [deg] | 0.129 |
| Refinement | |
| Resolution limit [Å] | 1.99-47.72 (1.99-2.04) |
| Completeness [%] | 99.9 (99.0) |
| No. of reflections | 31972 |
| R (work)/R (free) [%] | 23.0/27.3 (33.2/38.1) |
| Mean B value [Å$^2$] | 55.5 |
| RMSD bond length [Å] | 0.017 |
| RMSD bond angles [deg] | 2.03 |

Values in brackets refer to the highest resolution shell.

Absolute Configuration of Example 4.1 in Human SMYD2

The complex of human SMYD2, SAM and Example 4.1 (FIG. 3) crystallizes with one molecule in the asymmetric unit. The stereo chemistry of Example 4.1 is unambiguously defined by the knowledge of the stereo chemistry of the protein human SMYD2. Example 4.1 unambiguously features the S configuration on carbon atom C1. (FIG. 3). (Wang Ll, Li L, Zhang H, Luo X, Dai J, Zhou S, Gu J, Zhu J, Atadja P, Lu C, Li E, Zhao K. Structure of human SMYD2 protein reveals the basis of p53 tumor suppressor methylation.)

References for the crystallographic software tools CCP4: M. D. Winn et al. Acta. Cryst. D67, 235-242 (2011)

"Overview of the CCP4 suite and current developments" Phaser: *J. Appl. Cryst.* (2007). 40, 658-674.

Phaser crystallographic software. McCoy, A. J., Grosse-Kunstleve, R. W., Adams, P. D., Winn, M. D., Storoni, L. C., & Read, R. J.

Refmac: "Refinement of Macromolecular Structures by the Maximum-Likelihood method" G. N. Murshudov, A. A. Vagin and E. J. Dodson, (1997) in Acta Cryst. D53, 240-255.

ProDrg: A. W. Schüttelkopf and D. M. F. van Aalten (2004). "PRODRG: a tool for high-throughput crystallography of protein-ligand complexes", *Acta Crystallogr* D60, 1355-1363.

COOT: Paul Emsley, Bernhard Lohkamp, William G. Scott, Kevin Cowtan, "Features and Development of Coot", (2010) Acta Cryst. D66:486-501

Pharmaceutical Compositions of the Compounds

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised powder for IV administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

In accordance with another aspect therefore, the present invention covers a compound of general formula (I), or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned above.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol.

Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Another particular aspect of the present invention is therefore the use of a compound of general formula (I), described above, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula (I) described above for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by the Wnt pathway, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

DESCRIPTION OF THE FIGURES

FIG. 1 shows the sequence of human SMYD2 with N-terminal His tag before cleavage by TEV protease (SEQ ID NO: 1).

FIG. 2 shows the sequence of human SMYD2 after cleavage by TEV protease (SEQ ID NO: 2).

FIG. 3 shows the Example 4.1 in complex with human SMYD2 and SAM. Hydrogen atoms, SMYD2 and SAM are not shown. Carbon atom C1 unambiguously features S configuration.

Biological Activity of the Compounds According to the Invention

The following assays can be used to illustrate the commercial utility of the compounds according to the present invention.

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

1. Assays

The in vitro pharmacological properties of the compounds can be determined according to the following assays:

1.1 Scintillation Proximity Assay (SPA) for Detection of SMYD2 Enzymatic Inhibition SMYD2 inhibitory activities of the compounds described in the present invention were quantified using a scintillation proximity assay (SPA) which measures methylation by the enzyme of the synthetic, biotinylated peptide Btn-Ahx—GSRAHSSHLKSKKGQSTSRH (SEQ ID NO: 3)—Amid x TFA (Biosyntan) derived from p53 and referred to from here on as "p53 Peptide". The SMYD2 full length enzyme was produced in-house by expression (with an N-terminal 6×His tag) in $E.\ coli$ and purification by affinity chromatography on a Ni-NTA Sepharose column followed by a size exclusion chromatography step on a Superdex 200 16/60 column (GE Healthcare).

In a typical assay 11 different concentrations of each compound (0.1 nM, 0.33 nM, 1.1 nM, 3.8 nM, 13 nM, 44 nM, 0.15 µM, 0.51 µM, 1.7 µM, 5.9 µM and 20 µM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One), from which 50 nl of compound solutions were transferred into a white low volume test microtiter plate from the same supplier. Subsequently, 2.5 µl SMYD2 in aqueous assay buffer [50 mM Tris/HCl pH 9.0 (AppliChem), 1 mM dithiothreitol (DTT, Sigma), 0.01% (w/v) bovine serum albumine (BSA, Sigma), 0.0022% (v/v) Pluronic (Sigma)] were added to the compounds in the test plate to a final enzyme concentration of—typically—3 nM (this parameter was adjusted depending on the activity of the enzyme lot in order to be within the linear dynamic range of the assay). The samples were then incubated for 15 min at 22° C. to allow pre-equilibration of the putative enzyme-inhibitor complexes before the start of the methylation reaction, which was initiated by the addition of 2.5 µl 2-fold concentrated solution (in assay buffer) of titrated S-Adenosyl-L-Methionine (3H-SAM, Perkin Elmer, final concentration: 60 nM) and p53 Peptide substrate (final concentration: 1.0 µM). The resulting mixture (5 µl final volume) was shortly centrifuged (2 min., 1500 rpm) and incubated at 22° C. during 30 min. Thereupon the reaction was stopped by adding 3 µl of Streptavidin PS SPA imaging beads (Perkin Elmer, final concentration of 3.12 µg/µl) and "cold" SAM (AK Scientific, 25 µM final concentration) for non-specific binding reduction. Plates containing the stopped reaction were sealed with transparent adhesive foil (Perkin Elmer), centrifuged (2 min., 1500 rpm), and further incubated for—at least—1 h at RT (or overnight at 4° C.) in order to allow the SPA signals to develop. Subsequently, the amount of product was evaluated by measuring the energy transfer from the β-particles emitted by the 3H-labeled substrate to the Europium scintillator co-polymerized in the polystyrene matrix of the PS imaging beads, using the standard settings for this purpose of a Viewlux (Perkin-Elmer) CCD plate imaging device (emission filter 613/55 (IFP). The resulting scintillation counts were taken as indicator for the amount of methylated peptide per well. The data were normalised using two sets of control wells (typically 16 each) for high- (=enzyme reaction with DMSO instead of test compound=0%=Minimum inhibition) and low- (=all assay components without enzyme=100%=Maximum inhibition) SMYD2 activity. $IC_{50}$ values were calculated by fitting the normalized inhibition data to a 4-parameter logistic equation using the "Screener" analysis software from Genedata.

1.2 Cell-Based Assay for Detection of SMYD2 Methylation Activity

For the detection of SMYD2 cellular methylation activity an In Cell Western (ICW) assay was established. This assay allows rapid processing of multiple samples for SMYD2 methylation derived immunofluorescence signals, with normalization to cell number via the use of the nucleic acid dye DRAQ5. KYSE-150 cells (human esophageal carcinoma cell line; DSMZ-German Collection of Microorganisms and Cell Cultures; No: ACC 375) have been stably transfected with a construct expressing wild-type SMYD2 (NCBI Reference Sequence: NP_064582.2). To detect SMYD2-mediated methylation signals in cells, a customized antibody directed against mono-methylated lysine 370 on protein p53 (p53K370me1) was used. The polyclonal antibody was generated (Eurogentec) against a p53 peptide containing the mono-methylated K370 epitope as described elsewhere (Huang et al., Nature, 2006, 444(7119):629-32).

For conducting the ICW assay 5000 SMYD2 overexpressing KYSE-150 cells/well were seeded in 96-well plates (SIGMA) and cultivated for 24 h. As a control for maximal inhibition of ectopic methylation activity, non-transfected KYSE-150 cells were used. Cells were grown in 49% RPMI 1640 with 49% Ham's F12 media supplemented with 2% heat inactivated fetal calf serum (FCS). For determination of SMYD2 inhibitory activity, cells were treated for 72 h in the presence of compounds or with DMSO. Cells were treated with compounds to be tested at a final concentration range varying from $3.9 \times 10^{-8}$ to $5 \times 10^{-6}$ M. Media was removed and 3.7% (w/v) formaldehyde in PBS was added for 20 min. After two washes with phosphate buffered saline (PBS), 0.25% (v/v) Triton X100 in PBS was added for 15 minutes of permeabilization. After one washing step with PBS, cells were blocked for 1 h with 5% (w/v) non-fat dry milk in PBS. Fixed cells were exposed to primary p53K270me1 antibody in 5% non-fat dry milk in PBS for 24 h. One row of cells on each plate was not exposed to p53K370me1 antibody and was reserved for background control measurements. The wells were washed three times with PBS, then secondary IR800 conjugated antibody (LI-COR) and DNA-intercalating dye, 5 μM DRAQ5 (LI-COR) were added for 3 h. After 5 washes with PBS, the fluorescence in each well was measured on an Odyssey (LI-COR) scanner at 800 nm (p53K370me1 signal; 764 nm excitation) and 700 nm (DRAQ5 signal; 683 nm excitation). Fluorescence intensity was quantified and normalized to background and DRAQ5 signals. $IC_{50}$ values were calculated by fitting the normalized inhibition data to a 4-parameter logistic equation (Minimum, Maximum, $IC_{50}$, Hill; Y=Max+(Min−Max)/(1+(X/$IC_{50}$)Hill)) for each tested compound. For $IC_{50}$ determination C0 (=no inhibition) was defined as the signal measured for DMSO treated controls. Ci (maximal inhibition) was defined as the signal measured for non SMYD2 overexpressing KYSE150 cells.

Measurement of the Inhibitory Activity of Selected Compounds on the SMYD2 Methylation Activity

TABLE 2

| Example No | $IC_{50}$ [mol/l] (SPA Assay) | $IC_{50}$ [mol/l] (ICW assay) |
|---|---|---|
| 1 | 5.18E−07 | |
| 2 | 8.33E−08 | |
| 3 | 1.50E−08 | 1.01E−07 |
| 4 | 8.25E−08 | 1.76E−07 |
| 4.1 | 2.82E−08 | 4.67E−08 |
| 4.2 | 1.32E−06 | 1.39E−06 |
| 5 | 7.85E−07 | 4.14E−06 |
| 5.1 | >2.00E−05 | |
| 5.2 | 2.96E−07 | |
| 6 | 2.86E−07 | |
| 7.1 | 1.35E−08 | 1.32E−08 |
| 7.2 | 1.05E−06 | |
| 8 | 9.01E−08 | |
| 9 | 1.30E−08 | 2.64E−09 |

TABLE 2-continued

| Example No | $IC_{50}$ [mol/l] (SPA Assay) | $IC_{50}$ [mol/l] (ICW assay) |
|---|---|---|
| 10 | 4.66E−07 | 8.00E−06 |
| 10.1 | 1.99E−07 | |
| 10.2 | 3.83E−06 | |
| 11 | 1.44E−07 | 3.76E−07 |
| 11.1 | 4.41E−08 | |
| 11.2 | 2.98E−06 | |
| 12 | 1.38E−07 | |
| 12.1 | 2.66E−06 | |
| 12.2 | 5.41E−08 | |
| 13 | 8.67E−08 | 1.96E−07 |
| 13 | 2.54E−07 | |
| 13.1 | 4.61E−06 | |
| 13.2 | 5.00E−08 | 2.58E−07 |
| 14 | 1.47E−07 | |
| 15 | 1.21E−07 | |
| 15.1 | 1.76E−05 | |
| 15.2 | 7.10E−08 | 9.96E−08 |
| 16 | 3.58E−07 | |
| 16.1 | 4.79E−06 | |
| 16.2 | 1.59E−07 | 2.58E−06 |
| 17 | 5.95E−08 | |
| 18 | 1.25E−08 | 2.77E−08 |
| 18.1 | >2.00E−5 | |
| 18.2 | 3.00E−08 | 2.87E−08 |
| 19 | 9.98E−09 | 2.13E−08 |
| 19.1 | 7.68E−07 | |
| 19.2 | 6.65E−09 | 2.36E−08 |
| 20 | 2.47E−07 | 4.03E−07 |
| 20.1 | 1.74E−05 | |
| 20.2 | 1.19E−07 | |
| 21 | 1.07E−06 | |
| 21.1 | 5.30E−08 | |
| 21.2 | 7.63E−07 | |
| 22 | 6.48E−08 | |
| 23 | 6.74E−08 | |
| 24 | 6.31E−08 | |
| 24.1 | 2.51E−06 | |
| 24.2 | 1.92E−08 | |
| 25 | 1.08E−07 | |
| 25.1 | 2.06E−07 | |
| 25.2 | 1.03E−05 | |
| 26 | 3.06E−08 | |
| 27 | 3.55E−07 | 9.59E−08 |
| 27.1 | 7.32E−08 | |
| 27.2 | 1.62E−06 | |
| 28 | 1.40E−07 | |
| 29 | 5.55E−09 | 2.14E−07 |
| 30 | 1.58E−08 | |
| 31 | 9.09E−09 | 1.26E−07 |
| 32 | 2.61E−08 | |
| 33 | 8.45E−08 | |
| 33.1 | 1.84E−05 | |
| 33.2 | 3.76E−08 | 9.64E−08 |
| 34.1 | 1.54E−05 | |
| 34.2 | 4.88E−07 | |
| 35 | 1.57E−07 | |
| 36 | 4.07E−8 | 1.66E−7 |
| 36.1 | 7.54E−7 | |
| 36.2 | 2.29E−8 | |
| 37 | 2.31E−7 | |
| 38 | 3.20E−8 | 3.72E−8 |
| 38.1 | 1.35E−5 | |
| 38.2 | 3.75E−8 | 3.56E−8 |
| 39 | 2.40E−6 | |
| 40 | 4.18E−7 | |
| 41 | 7.35E−8 | |

What is claimed is:
1. A compound of formula (I)

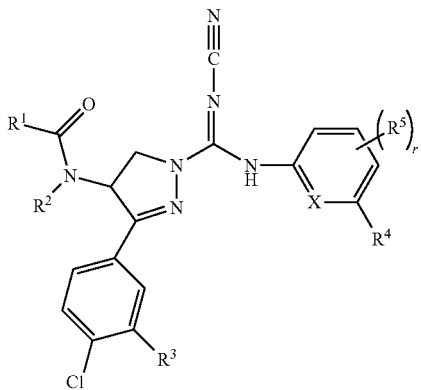

wherein:
R¹ is a $C_1$-$C_6$-alkyl group, which is substituted with one substituent selected from —OH, —NH₂ or —NHCH₃;
R² is a hydrogen atom, a methyl or an ethyl group;
R³ is a fluorine or a chlorine atom or a methyl group;
R⁴ is a group selected from: —CF₃, —CH₂CF₃, —OCH₃, —OCHF₂, —OCF₃, —OCH₂CF₃ or —OCH₂CH₂N(CH₃)₂;
R⁵ is a fluorine or a chlorine atom or a group selected from: —OCH₃, —OCF₃,

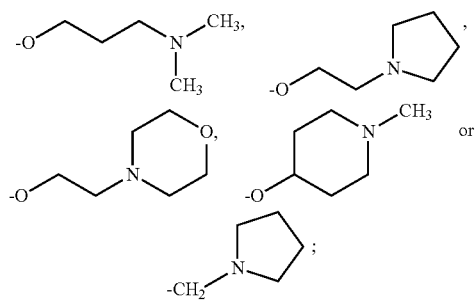

X is CH or N; and
r is 0 or 1,
or a polymorph, an enantiomer, a diastereomer, a racemate, an E/Z-isomer, a tautomer, a solvate, a physiologically acceptable salt, or a solvate of a physiologically acceptable salt thereof.

2. The compound of formula (I) according to claim 1 wherein:
R¹ is the group —CH₂—OH, —CH(OH)—CH₃, —C(CH₃)₂—OH, —CH₂—NH₂, —CH₂—NH—CH₃, —CH(CH₃)—NH₂, —CH₂—CH₂—NH₂, —CH₂—CH₂—CH₂—NH₂, —CH(NH—CH₃)—CH₃, —CH(CH(CH₃)₂)—NH₂, —C(CH₃)(CH(CH₃)₂)—NH₂ or —CH—(CH₂—CH(CH₃)₂)—NH₂;
R² is a hydrogen atom, a methyl or an ethyl group;
R³ is a fluorine or a chlorine atom or a methyl group;
R⁴ is a group selected from: —CF₃, —CH₂CF₃, —OCH₃, —OCHF₂, —OCF₃, —OCH₂CF₃ or —OCH₂CH₂N(CH₃)₂;
R⁵ is a fluorine or a chlorine atom or a group selected from: —OCH₃, —OCF₃,

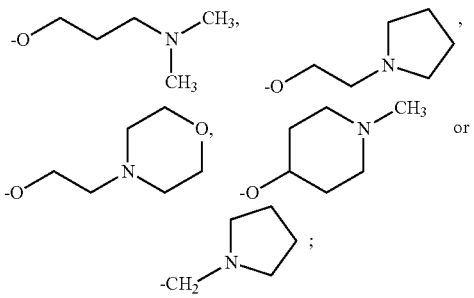

X is CH or N; and
r is 0 or 1,
or a polymorph, an enantiomer, a diastereomer, a racemate, an E/Z-isomer, a tautomer, a solvate, a physiologically acceptable salt, or a solvate of a physiologically acceptable salt thereof.

3. The compound of formula (I) according to claim 1, which is selected from the group consisting of:
(2S)—N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxypropanamide (1:1 mixture of diastereomers);
Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-N-methylacetamide;
Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylglycinamide;
Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide;
N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 1;
N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxyacetamide Isomer 2;
Rac-N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide;
N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 1;
N-[1-{N'-cyano-N-[3-(difluoromethoxy)phenyl]carbamimidoyl}-3-(3,4-dichlorophenyl)-4,5-dihydro-1H-pyrazol-4-yl]-2-hydroxy-2-methylpropanamide Isomer 2;
Rac-N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-beta-alaninamide;
N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide (1:1 mixture of diastereomers);
N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 1;
N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-D-alaninamide Isomer 2;

(2S)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 mixture of diastereomers);

(2R)—N-[1-{N'-cyano-N-[3-(difluoromethoxy)phenyl]carbamimidoyl}-3-(3,4-dichlorophenyl)-4,5-dihydro-1H-pyrazol-4-yl]-N-ethyl-2-hydroxypropanamide (1:1 mixture of diastereomers);

Rac-4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide;

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 1;

4-amino-N-[1-{N'-cyano-N-[3-(difluoromethoxy)phenyl]carbamimidoyl}-3-(3,4-dichlorophenyl)-4,5-dihydro-1H-pyrazol-4-yl]-N-ethylbutanamide Isomer 2;

Rac-N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide;

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 1;

N-[1-{N-[4-chloro-3-(difluoromethoxy)phenyl]-N'-cyanocarbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[4-fluoro-3-(trifluoromethoxy)phenyl]carbamimidoyl}-3-(3,4-dichlorophenyl)-4,5-dihydro-1H-pyrazol-4-yl]-N-ethyl-2-hydroxyacetamide;

Rac-N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide;

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 1;

N-{1-[N'-cyano-N-(3-methoxyphenyl)carbamimidoyl]-3-(3,4-dichlorophenyl)-4,5-dihydro-1H-pyrazol-4-yl}-N-ethyl-2-hydroxyacetamide Isomer 2;

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide;

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 1;

N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethyl-2-hydroxyacetamide Isomer 2;

Rac-N-[1-(N'-cyano-N-{3-[2-(dimethylamino)ethoxy]phenyl}carbamimidoyl)-3-(3,4-dichlorophenyl)-4,5-dihydro-1H-pyrazol-4-yl]-N-ethylglycinamide;

Rac-N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[5-(difluoromethoxy)-2-methoxyphenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-methoxy-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide;

N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[6-(difluoromethoxy)pyridin-2-yl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(2,2,2-trifluoroethyl)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-(difluoromethoxy)-4-fluorophenyl]carbamimidoyl}-3-(3,4-dichlorophenyl)-4,5-dihydro-1H-pyrazol-4-yl]-N-ethyl-2-hydroxyacetamide;

Rac-N-[1-{N'-cyano-N-[3-(difluoromethoxy)-2-fluorophenyl]carbamimidoyl}-3-(3,4-dichlorophenyl)-4,5-dihydro-1H-pyrazol-4-yl]-N-ethyl-2-hydroxyacetamide;

Rac-N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-(difluoromethoxy)-5-fluorophenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[3-fluoro-5-(trifluoromethoxy)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-methoxy-5-(trifluoromethoxy)phenyl]carbamimidoyl}-3-(3,4-dichlorophenyl)-4,5-dihydro-1H-pyrazol-4-yl]-N-ethyl-2-hydroxyacetamide;

Rac-N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide;

N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 1;

N-[1-{N'-cyano-N-[2-(pyrrolidin-1-ylmethyl)-5-(trifluoromethyl)phenyl]carbamimidoyl}-3-(3,4-dichlorophenyl)-4,5-dihydro-1H-pyrazol-4-yl]-N-ethyl-2-hydroxyacetamide Isomer 2;

Rac-N-[1-{N'-cyano-N-[2-(trifluoromethoxy)-5-(trifluoromethyl)phenyl]carbamimidoyl}-3-(3,4-dichlorophenyl)-4,5-dihydro-1H-pyrazol-4-yl]-N-ethyl-2-hydroxyacetamide;

Rac-N-[1-(N'-cyano-N-{5-(difluoromethoxy)-2-[3-(dimethylamino)propoxy]phenyl}-carbamimidoyl)-3-(3,4-dichlorophenyl)-4,5-dihydro-1H-pyrazol-4-yl]-N-ethyl-2-hydroxyacetamide;

Rac-N-[1-(N'-cyano-N-{2-[2-(pyrrolidin-1-yl)ethoxy]-5-(trifluoromethyl)phenyl}carbamimidoyl)-3-(3,4-dichlorophenyl)-4,5-dihydro-1H-pyrazol-4-yl]-N-ethyl-2-hydroxyacetamide;

Rac-N-[1-(N'-cyano-N-{2-[(1-methylpiperidin-4-yl)oxy]-5-(trifluoromethyl)phenyl}-carbamimidoyl)-3-(3,4-dichlorophenyl)-4,5-dihydro-1H-pyrazol-4-yl]-N-ethyl-2-hydroxyacetamide;

Rac-N-[1-(N'-cyano-N-{2-[(1-methylpiperidin-4-yl)oxy]-5-(trifluoromethyl)phenyl}-carbamimidoyl)-3-(3,4-dichlorophenyl)-4,5-dihydro-1H-pyrazol-4-yl]-N-ethyl-2-hydroxyacetamide;

Rac-N-[3-(4-chloro-3-methylphenyl)-1-{N'-cyano-N-[3-(difluoromethoxy)phenyl]-carbamimidoyl}-4,5-dihydro-1H-pyrazol-4-yl]-N-ethyl-2-hydroxyacetamide;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-2-hydroxyacetamide Isomer 1;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-2-hydroxyacetamide Isomer 2;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide (1:1 mixture of diastereomers);

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide Isomer 1;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-L-alaninamide Isomer 2;

Rac-N-[3-(4-chloro-3-fluorophenyl)-1-{N'-cyano-N-[3-(trifluoromethoxy)phenyl]-carbamimidoyl}-4,5-dihydro-1H-pyrazol-4-yl]-N-ethyl-2-hydroxyacetamide;

Rac-N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-$N^2$-methylglycinamide;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-$N^2$-methylglycinamide Isomer 1;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-$N^2$-methylglycinamide Isomer 2;

N-[3-(4-chloro-3-methylphenyl)-1-{N'-cyano-N-[3-(difluoromethoxy)phenyl]carbamimidoyl}-4,5-dihydro-1H-pyrazol-4-yl]-N-ethyl-$N^2$-methyl-D-alaninamide;

Rac-N-[1-{N'-cyano-N-[3-(difluoromethoxy)phenyl]carbamimidoyl}-3-(3,4-dichlorophenyl)-4,5-dihydro-1H-pyrazol-4-yl]-3-methyl-D-isovalinamide;

N-[1-{N'-Cyano-N-[3-(difluoromethoxy)phenyl]carbamimidoyl}-3-(3,4-dichlorophenyl)-4,5-dihydro-1H-pyrazol-4-yl]-3-methyl-D-isovalinamide Isomer 1;

N-[1-{N'-Cyano-N-[3-(difluoromethoxy)phenyl]carbamimidoyl}-3-(3,4-dichlorophenyl)-4,5-dihydro-1H-pyrazol-4-yl]-3-methyl-D-isovalinamide Isomer 2;

N-[1-{N'-cyano-N-[3-(trifluoromethoxy)phenyl]carbamimidoyl}-3-(3,4-dichlorophenyl)-4,5-dihydro-1H-pyrazol-4-yl]-N-ethyl-D-leucinamide;

N-[1-{N'-Cyano-N-[2-fluoro-3-(trifluoromethoxy)phenyl]carbamimidoyl}-3-(3,4-dichlorophenyl)-4,5-dihydro-1H-pyrazol-4-yl]-N-ethyl-D-valinamide; and N-[1-{N'-Cyano-N-[3-(difluoromethoxy)phenyl]carbamimidoyl}-3-(3,4-dichlorophenyl)-4,5-dihydro-1H-pyrazol-4-yl]-N-ethyl-D-valinamide, or a polymorph, an enantiomer, a diastereomer, a racemate, an E/Z-isomer, a tautomer, a solvate, a physiologically acceptable salt, or a solvate of a physiologically acceptable salt thereof.

4. A method for treatment of hyperproliferative disorders responsive to inhibition of SMYD2 methylation, comprising administering to a patient in need thereof a pharmaceutically effective amount of the compound according to claim 1, or a polymorph, an enantiomer, a diastereomer, a racemate, an E/Z-isomer, a tautomer, a solvate, a physiologically acceptable salt, or a solvate of a physiologically acceptable salt thereof.

5. A method for treatment of cancer responsive to inhibition of SMYD2 methylation, comprising administering to a patient in need thereof a pharmaceutically effective amount of the compound according to claim 1, or a polymorph, an enantiomer, a diastereomer, a racemate, an E/Z-isomer, a tautomer, a solvate, a physiologically acceptable salt, or a solvate of a physiologically acceptable salt thereof.

6. A pharmaceutical combination comprising the compound of formula (I) according to claim 1, or a polymorph, an enantiomer, a diastereomer, a racemate, an E/Z-isomer, a tautomer, a solvate, a physiologically acceptable salt, or a solvate of a physiologically acceptable salt thereof, in combination together with and one or more additional pharmaceutically pharmaceutical active compounds.

7. A pharmaceutical formulation comprising the compound of general formula (I) according to claim 1, or a polymorph, an enantiomer, a diastereomer, a racemate, an E/Z-isomer, a tautomer, a solvate, a physiologically acceptable salt, or a solvate of a physiologically acceptable salt thereof.

8. The method according to claim 5, wherein the cancer is esophageal cancer.

9. The compound according to claim 1 or a physiologically acceptable salt thereof.

10. The method according to claim 4, comprising administering the compound of formula (I) or a physiologically acceptable salt thereof.

11. The method according to claim 5, comprising administering the compound of formula (I) or a physiologically acceptable salt thereof.

12. The pharmaceutical combination according to claim 6, comprising the compound of formula (I) or a physiologically acceptable salt thereof.

13. The pharmaceutical formulation according to claim 7, comprising the compound of formula (I) or a physiologically acceptable salt thereof.

14. The compound according to claim 3 or a physiologically acceptable salt thereof.

* * * * *